US012655088B2

(12) United States Patent
Wang et al.

(10) Patent No.: US 12,655,088 B2
(45) Date of Patent: Jun. 16, 2026

(54) COMPOUND FOR TREATING ALZHEIMER'S DISEASE

(71) Applicants: XIAMEN UNIVERSITY, Xiamen (CN); EAST CHINA UNIVERSITY OF SCIENCE AND TECHNOLOGY, Shanghai (CN)

(72) Inventors: Xin Wang, Xiamen (CN); Lei Ma, Shanghai (CN); Jianjun Fu, Shanghai (CN); Qiuyang Zheng, Xiamen (CN); Licheng Zhou, Shanghai (CN); Qingfang Deng, Xiamen (CN); Ximeng Shi, Shanghai (CN); Guilin Li, Xiamen (CN); Shihua Wang, Xiamen (CN); Anjie Di, Xiamen (CN)

(73) Assignees: XIAMEN UNIVERSITY, Xiamen (CN); EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 912 days.

(21) Appl. No.: 17/759,264

(22) PCT Filed: Jan. 21, 2021

(86) PCT No.: PCT/CN2021/073164

§ 371 (c)(1),
(2) Date: Jul. 21, 2022

(87) PCT Pub. No.: WO2021/147971

PCT Pub. Date: Jul. 29, 2021

(65) Prior Publication Data

US 2023/0104617 A1 Apr. 6, 2023

(30) Foreign Application Priority Data

Jan. 21, 2020 (CN) ........................ 202010071143.7

(51) Int. Cl.

| | |
|---|---|
| ***A61K 38/17*** | (2006.01) |
| ***A61P 25/28*** | (2006.01) |
| ***A61P 43/00*** | (2006.01) |
| ***C07C 43/295*** | (2006.01) |
| ***C07C 47/575*** | (2006.01) |
| ***C07C 217/58*** | (2006.01) |
| ***C07D 209/14*** | (2006.01) |
| ***C07D 211/26*** | (2006.01) |
| ***C07D 213/74*** | (2006.01) |
| ***C07D 217/20*** | (2006.01) |
| ***C07D 295/096*** | (2006.01) |

(52) U.S. Cl.
CPC ............ *C07C 217/58* (2013.01); *A61P 25/28* (2018.01); *A61P 43/00* (2018.01); *C07C 43/295* (2013.01); *C07C 47/575* (2013.01); *C07D 209/14* (2013.01); *C07D 211/26* (2013.01); *C07D 213/74* (2013.01); *C07D 217/20* (2013.01); *C07D 295/096* (2013.01)

(58) Field of Classification Search
CPC ................................ A61P 25/28; A61K 38/17
See application file for complete search history.

(56) References Cited

FOREIGN PATENT DOCUMENTS

| | | | |
|---|---|---|---|
| CN | 105408325 | A | 3/2016 |
| CN | 109071561 | A | 12/2018 |
| CN | 109206503 | A | 1/2019 |
| CN | 109646668 | A | 4/2019 |
| JP | 2016135778 | A | 7/2016 |
| WO | 2016108045 | A2 | 7/2016 |

OTHER PUBLICATIONS

Wrigley et al., "Identification and Characterization of Dual Inhibitors of the USP25/28 Deubiquitinating Enzyme Subfamily", ACS Chemical biology, No. 12, Nov. 13, 2017,cited in ISR.
Guilin Li, The role of ubiquitin specific protease 25 in pathogenesis of Alzheimer's disease, with English translation for Abstract, May 2018, 64 pages, cited in ISR.
International Search Report and Written Opinion issued in PCT/CN2021/073164, dated Apr. 26, 2021, with English translation, 19 pages.

*Primary Examiner* — Bruck Kifle
(74) *Attorney, Agent, or Firm* — HSML P.C.

(57) ABSTRACT

Provided in the present invention are a compound as shown in formula I, various crystal forms thereof, a hydrate, a solvate or a pharmaceutically acceptable salt thereof, and a pharmaceutical composition. The compound of the present invention can effectively treat Alzheimer's disease or Down's syndrome, especially cognitive function impairment caused by Alzheimer's disease or Down's syndrome. Also disclosed in the present invention is use of a ubiquitin specific protease USP25 encoded and expressed by chromosome 21 for preventing, treating or ameliorating Alzheimer's disease or Down's syndrome.

I

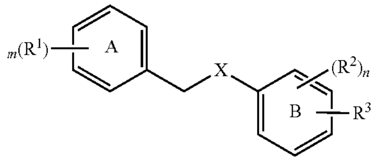

8 Claims, 11 Drawing Sheets

COMPOUND FOR TREATING ALZHEIMER'S DISEASE

TECHNICAL FIELD

The present invention relates to the field of medicine. In particular, the present invention relates to a small molecule compound for treating Alzheimer's disease or Down's syndrome and applications thereof.

BACKGROUND

Alzheimer's disease (AD) is one of the most common degenerative diseases of the central nervous system that occurs in the elderly. It is clinically characterized by progressive memory, cognitive impairment and abnormal behavior. Typical pathological manifestations are: Amyloid plaques (Amyloid plaques), neurofibrillary tangles (NFT). With the aging of the social population, the prevalence of Alzheimer's disease is gradually increasing: in the population aged 65-74, the incidence of AD is about 5%, while in the population over 85 years old, the incidence of AD is about 50%. AD has become a global public health problem.

It is estimated that by 2020, there will be more than 40 million dementia patients in the world, and AD patients account for about 50% to 60% of them. AD will bring great harm and economic burden to the patients themselves and their families, and bring huge social pressure, and, therefore, attract more and more attention from medical and scientific researchers.

Two prominent pathological features in the brain of AD patients are amyloid plaques formed by amyloid (β-amyloid, Aβ) and neurofibrillary tangles formed by the aggregation of hyperphosphorylated tau protein, and neuronal loss with glue cell proliferation, etc. However, the pathogenesis of AD is still unclear, and there is no effective treatment so far. According to the research on the pathogenesis of Alzheimer's disease in recent years, the occurrence of chronic inflammatory response in the brain of AD patients also means that AD may be a chronic inflammatory response of the central nervous system. Activation of astrocytes and microglia is also an important hallmark of AD neuroinflammation. In the early stage of AD disease, microglia, as the main immune cells in the brain, play a key role in clearing Aβ amyloid plaques, limiting the formation and spread of Aβ oligomers, and spreading pathological tau proteins, suggesting that microglia-mediated innate immunity plays an important role in the development of AD pathology. Abnormally activated microglia induce neurotoxicity by releasing inflammatory factors. In addition, abnormally activated microglia also lead to synapse loss and synaptic dysfunction, indicating that abnormal microglial function is a key factor in the development of AD.

In addition, there are great differences in the mechanism between specific neurodegenerative diseases. At present, there are very few drugs for treating neurodegenerative diseases, and there are no effective drugs for some neurodegenerative diseases. For example, the main affected brain areas of AD are the cortex and hippocampus, which are responsible for learning and memory. Two prominent pathological features in the brain of patients are amyloid plaques formed by amyloid Aβ and neurofibrillary tangles formed by the aggregation of hyperphosphorylated tau protein, and neuronal loss with glue cell proliferation. Parkinson's disease (PD) is another common neurodegenerative disease that is more common in the elderly, with an average age of onset around 60 years old. The main affected brain area of PD is the midbrain, main pathological changes of which are the degeneration and death of dopaminergic neurons in the substantia nigra, resulting in a significant decrease in striatal DA content and causing disease. The main function of the current PD treatment drug, levodopa is to supplement the dopamine content in the brain. Huntington's disease (HD), also known as chorea, is an autosomal dominant neurodegenerative disease, the main cause of which is the mutation of the HTT gene on the fourth chromosome of the patient, resulting in the mutated protein. There are many repeats of glutamine in the abnormal HTT protein in Huntington's disease patients, the abnormal huntingtin protein is prone to aggregation, has cytotoxicity and can cause nerve cell death, and there is currently no treatment for the disease. Main pathological manifestations of amyotrophic lateral sclerosis (ALS) are motor neuron damage and death, which gradually lead to muscle weakness and atrophy including the muscles innervated by the medulla, limbs, trunk, chest, and abdomen, and eventually lead to the death of the patient. There is currently no treatment for the disease. Therefore, Alzheimer's disease is significantly different from other common neurodegenerative diseases in both intrinsic mechanism and extrinsic symptoms.

Drugs routinely used in other neurodegenerative diseases, such as Parkinson's disease, are ineffective against Alzheimer's disease. Therefore, at present, there is a lack of drugs that can treat, prevent or relieve Alzheimer's disease.

Therefore, there is an urgent need in the art for technical means capable of treating, preventing and improving Alzheimer's disease and clinical symptoms thereof.

The abnormal accumulation of neurotoxic proteins was found in the brains of AD patients, suggesting that the dysfunction of the ubiquitin-proteasome system (UPS) may be involved in the occurrence and development of neurodegenerative diseases. The ubiquitination pathway, like the phosphorylation pathway, is also a reversible process. There are also some specific deubiquitinated proteases in cells for negative regulation. USP25 gene is located on chromosome 21 q11.2 and belongs to the deubiquitinating protease family, containing a protein deubiquitinase activity region. In situ hybridization showed that USP25 was highly expressed in the brain, and also highly expressed in neurons, microglia and astrocytes. Down's syndrome (DS) is the most common genetic disorder of intellectual disability, and patients with Down's syndrome carry a third complete or partial chromosome 21. In Down syndrome cells, there is one extra copy of USP25 gene, and the increased expression of USP25 affects the ubiquitination level and protein homeostasis of its substrates. As one of the most important genetic risk factors for early-onset AD, 100% of Down syndrome patients over the age of 40 will have AD pathological features, which provides a theoretical basis for studying the role of USP25 in the pathogenesis of DS and AD. In addition, some articles reported that USP25 is involved in autoimmune regulation and inflammatory response. Our study found that USP25 is involved in the occurrence and development of AD and DS, and USP25 inhibitors may be used as therapeutic drugs for AD and DS neuroinflammation and cognitive impairment.

SUMMARY OF THE INVENTION

The purpose of the present invention is to provide a small molecule compound that can effectively treat Alzheimer's disease and its related diseases Down's syndrome, especially cognitive impairment caused by Alzheimer's disease and Down's syndrome.

In the first aspect, the present inventors discovered and clarified for the first time that the ubiquitin-specific protease USP25 restores the homeostasis of microglial cells in the AD brain by inhibiting the neuroinflammatory response and synaptic phagocytosis of microglial cells, thereby reversing the Synaptic function and cognitive impairment of model mice 5×FAD of Alzheimer's disease; and knockout of Usp25 can improve microglial homeostasis and reverse synaptic and cognitive deficits in 5×FAD mice. In addition, knockout of Usp25 also ameliorated the synaptic and cognitive deficits in Down's mice Dp16. The present invention provided a potential drug target for clinical treatment of Alzheimer's disease and Down's syndrome.

In the second aspect, the present invention provides the use of a compound of formula I, various crystal forms, hydrates, solvates or pharmaceutically acceptable salts thereof in the preparation of a drug for preventing, treating or improving Alzheimer's disease or Down's syndrome,

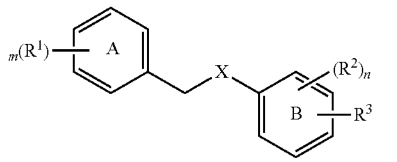

I

Wherein,

X is independently selected from O or NH;

each A ring and B ring is independently a benzene ring;

$R^1$ is independently selected from a hydrogen, deuterium, halogen, cyano, substituted or unsubstituted ($C_1$-$C_6$) alkyl, or substituted or unsubstituted ($C_1$-$C_6$) alkoxy;

m is 0, 1, 2, 3, 4 or 5;

$R^2$ is independently selected from a hydrogen, halogen, substituted or unsubstituted ($C_1$-$C_6$)alkyl, substituted or unsubstituted ($C_2$-$C_6$)alkenyl, substituted or unsubstituted ($C_2$-$C_6$)alkynyl, or substituted or unsubstituted ($C_1$-$C_6$)alkoxy;

n is 1 or 2;

$R^3$ is a substituted or unsubstituted ($C_1$-$C_6$) aldehyde group,

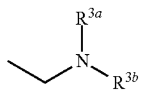 or 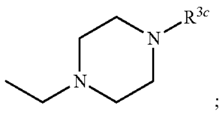;

Wherein each $R^{3a}$, $R^{3b}$, $R^{3c}$ is independently selected from a hydrogen, substituted or unsubstituted ($C_1$-$C_6$)alkyl, substituted or unsubstituted ($C_2$-$C_6$)alkenyl, substituted or unsubstituted ($C_2$-$C_6$)alkynyl, or

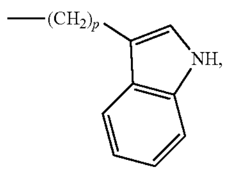

and p is an integer of 1-3 (preferably, p is 2).

In a specific embodiment, the substitution position of $R^3$ on the benzene ring is the ortho position or the meta position; preferably, the ortho position.

In a preferred embodiment, $R^1$ is independently selected from a hydrogen, fluorine, chlorine, bromine or iodine (preferably fluorine), cyano, substituted or unsubstituted ($C_1$-$C_4$)alkyl, or substituted or unsubstituted ($C_1$-$C_4$)alkoxy.

In a preferred embodiment, each $R^1$ is independently selected from a fluorine, trifluoromethyl, or trifluoromethoxy.

In a preferred embodiment, $R^2$ is independently selected from a hydrogen, fluorine, chlorine, bromine or iodine (preferably bromine), substituted or unsubstituted ($C_1$-$C_4$) alkyl, substituted or unsubstituted ($C_2$-$C_4$)alkenyl, substituted or unsubstituted ($C_2$-$C_4$)alkynyl, or substituted or unsubstituted ($C_1$-$C_4$)alkoxy.

In a preferred embodiment, $R^2$ is independently selected from a hydrogen, fluorine, chlorine, bromine, methyl, ethyl, n-propyl, allyl, propargyl, $-OCH_2CH_2CH_3$, $-OCH_2CH_3$, $-OCH_3$, $-CHF_2$, $-CF_3$, $-OCHF_2$, or $-OCF_3$.

In a preferred embodiment, each $R^{3a}$, $R^{3b}$, $R^{3c}$ is independently selected from a hydrogen, substituted or unsubstituted ($C_1$-$C_4$)alkyl, substituted or unsubstituted ($C_2$-$C_4$) alkenyl, or substituted or unsubstituted ($C_2$-$C_4$)alkynyl.

In a preferred embodiment, the substituted ($C_1$-$C_4$)alkyl is independently selected from a hydroxyl($C_1$-$C_4$)alkyl, $R^{4a}R^{4b}$ amino($C_1$-$C_4$)alkyl or sulfhydryl($C_1$-$C_4$)alkyl, and the $R^{4a}$ and $R^{4b}$ are independently a substituted or unsubstituted ($C_1$-$C_3$)alkyl; preferably a hydroxyl($C_1$-$C_4$)alkyl, or $R^{4a}R^{4b}$ amino($C_1$-$C_4$)alkyl.

In a preferred embodiment, the term "substituted" is halo, preferably fluoro.

In a specific embodiment, $R^1$ is independently selected from a hydrogen, fluorine, chlorine, bromine, ($C_1$-$C_3$)alkyl, halo($C_1$-$C_3$)alkyl, or halo($C_1$-$C_3$)alkoxy;

m is 0, 1, 2, or 3;

$R^2$ is independently selected from a hydrogen, or halogen;

n is 1 or 2;

$R^3$ is

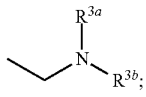;

Wherein each $R^{3a}$, $R^{3b}$ is independently selected from a hydrogen, hydroxyl-substituted ($C_1$-$C_4$)alkyl, or

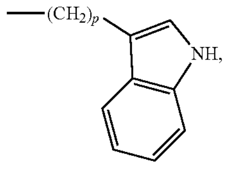

and p is an integer of 1-3 (preferably, p is 2).

In a specific embodiment, the compound of formula I is selected from the following compounds:

AZ1
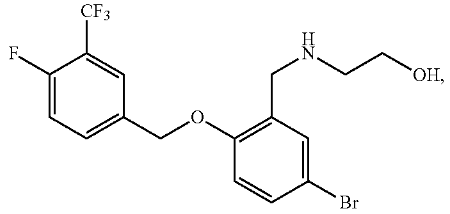
AZ2
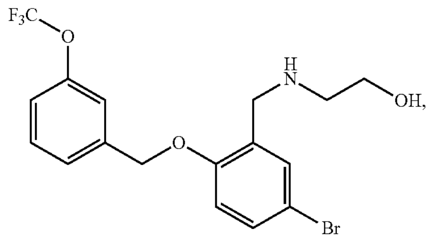
XMU1
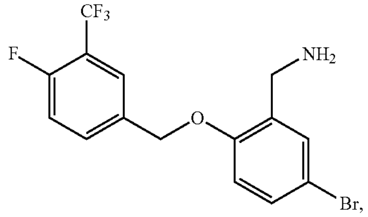
MZ39
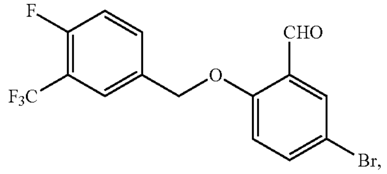
(1) MZ3
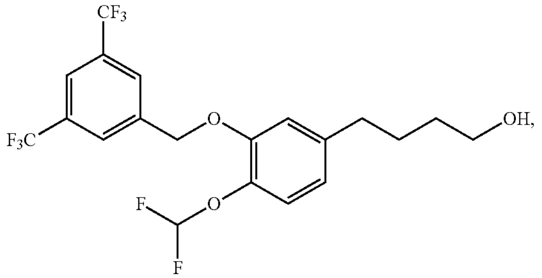
(2) MZ23
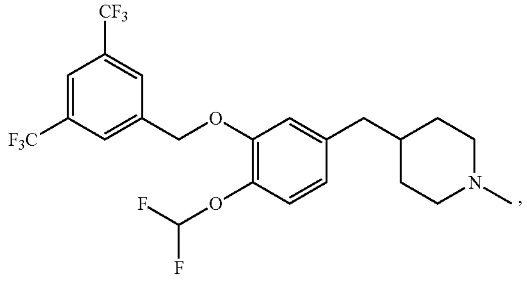
-continued
(3) MZ25
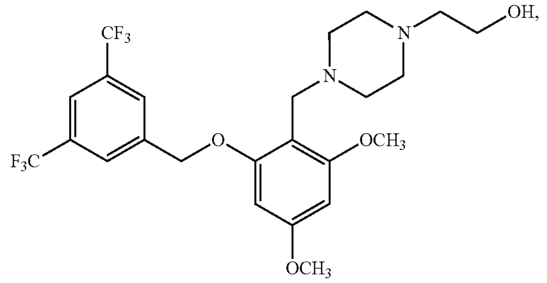
(4) MZ28
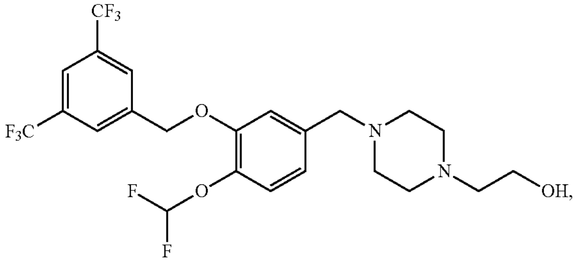
(5) MZ29
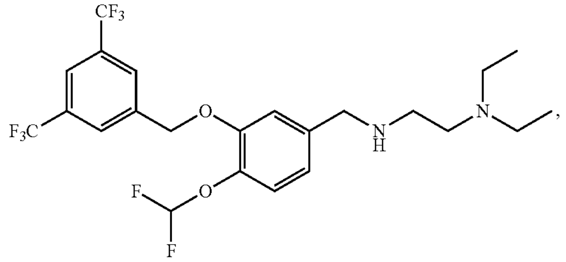
(6) MX24
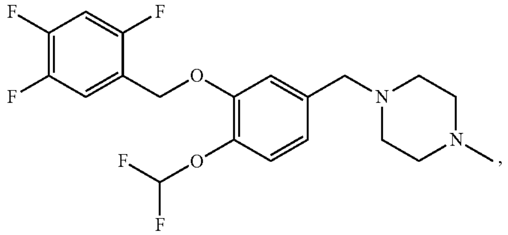
(7) MZ26
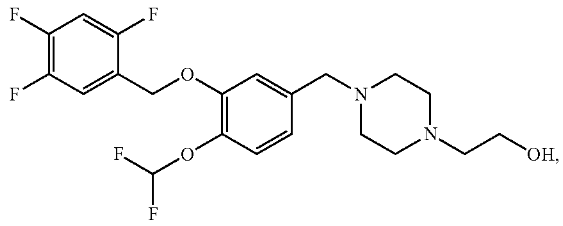
(8) MZ34
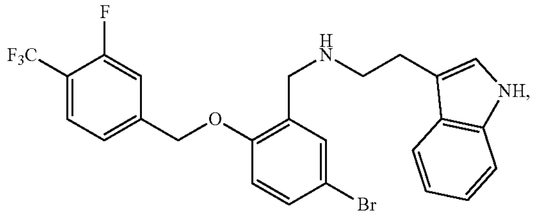

-continued
(9) MZ31
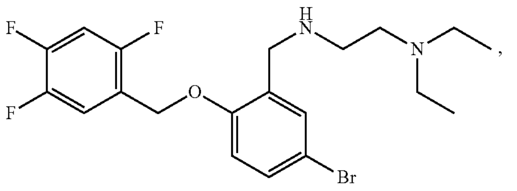
(10) MZ75
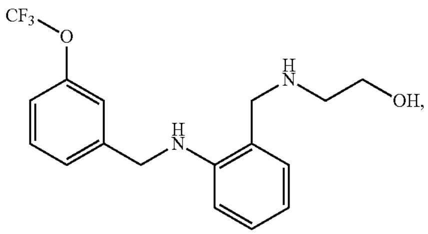
(11) MZ76
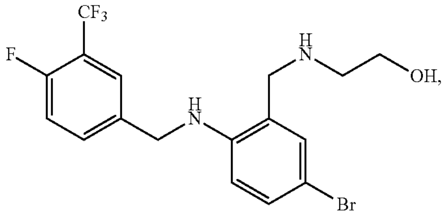
(12) MZ77
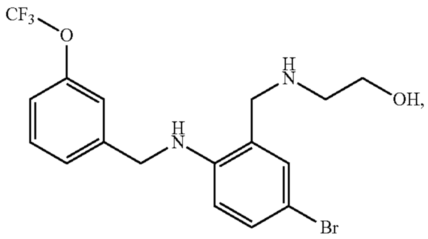
(13) MZ1
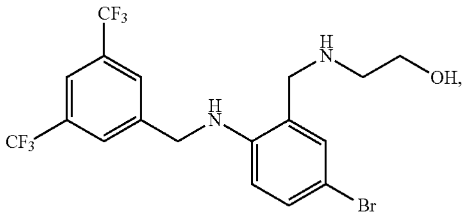
(14) MZ30
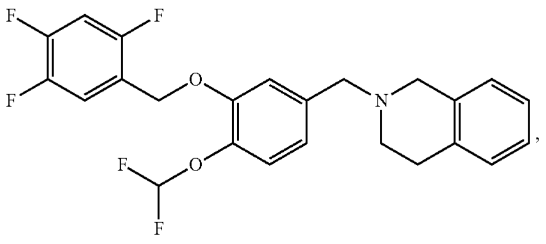
-continued
(15) MZ32
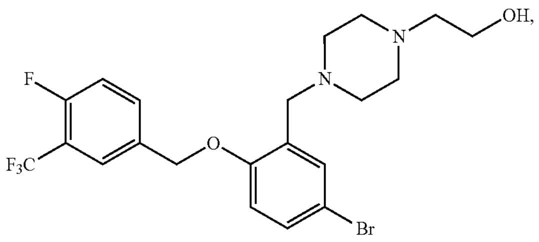
(16) MZ67
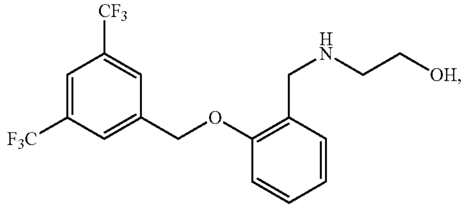
(17) MZ66
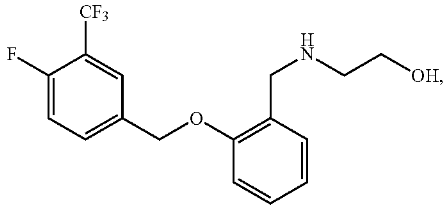
(18) MZ5
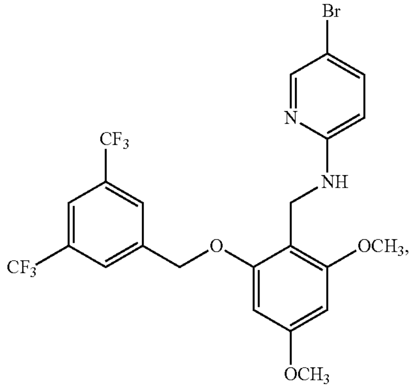
(19) MZ71
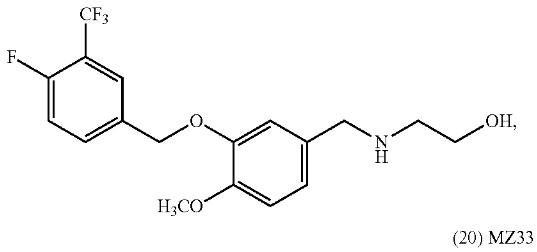
(20) MZ33
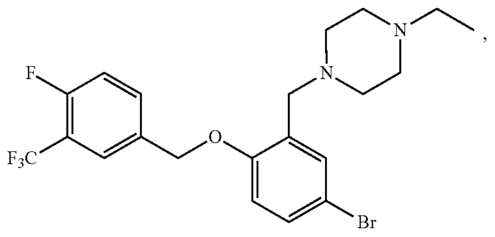

-continued
(21) MZ74
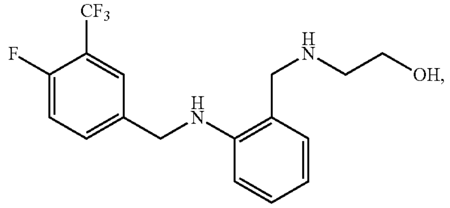
(22) MZ68
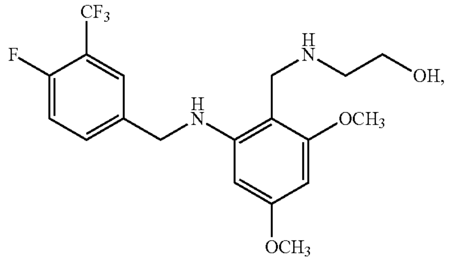
(23) MZ72
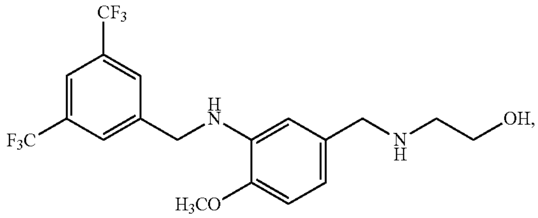
(24) MZ41
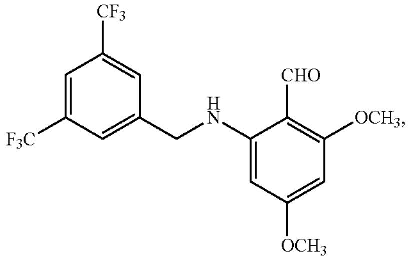
(25) MZ43
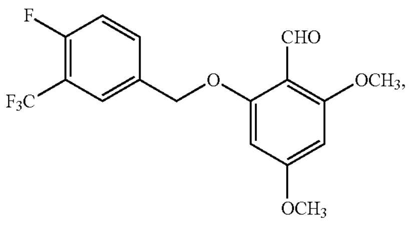
(26) MZ38
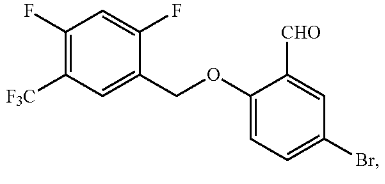
-continued
(27) MZ40
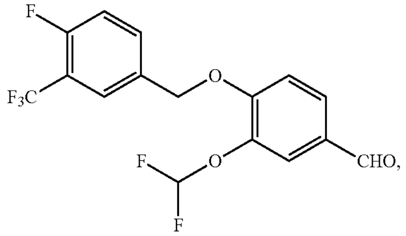
(28) MZ69
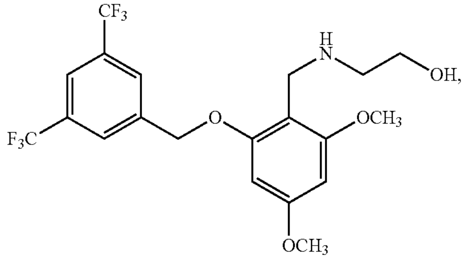
(29) MZ42
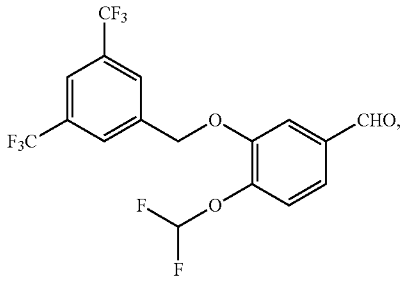
(30) MZ35
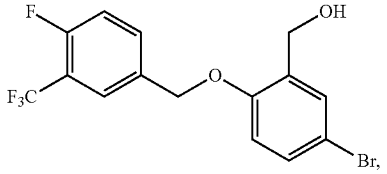
(31) MZ36
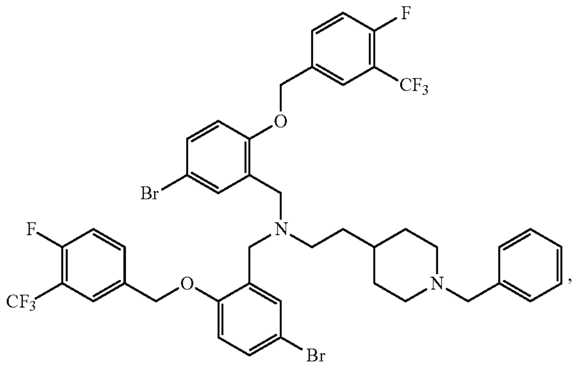
(32) MZ37
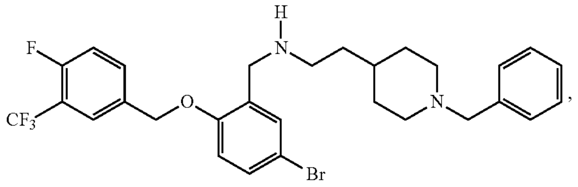

-continued

(33) MZ27

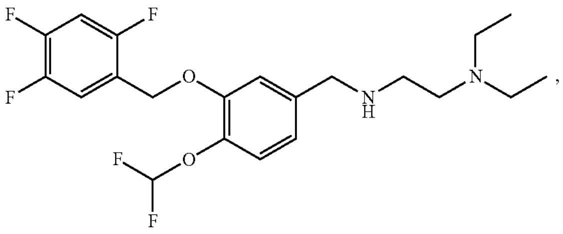

(34) MZ4

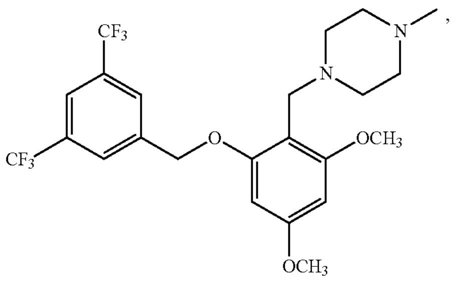

(35) MZ70

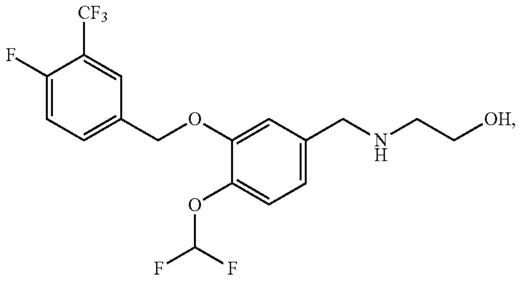

(36) MZ22

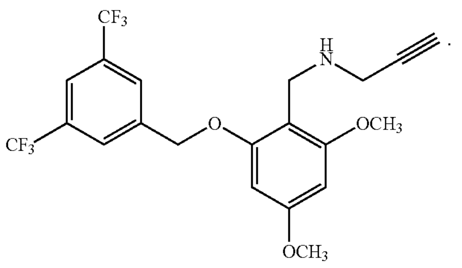

In a specific embodiment, the compound of formula I is AZ1, AZ2, MZ77, MZ76, MZ1, MZ30, MZ32, MZ67, MZ66, MZ75, MZ31, MZ34, MZ74, MZ68, MZ29, MZ72, MZ38 or MZ24.

In a specific embodiment, the expression "preventing, treating or improving Alzheimer's disease or Down's syndrome" refers to the prevention, treatment or improvement of cognitive impairment caused by Alzheimer's disease or Down's syndrome.

In a third aspect, the present invention provides a compound of formula I, various crystal forms, hydrates, solvates or pharmaceutically acceptable salts thereof,

I

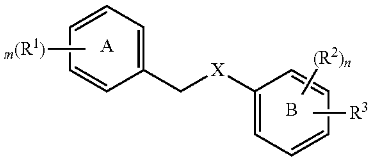

Wherein:

each A ring and B ring is independently a benzene ring;

$R^1$ is independently selected from a hydrogen, deuterium, halogen, cyano, substituted or unsubstituted $(C_1-C_6)$ alkyl, or substituted or unsubstituted $(C_1-C_6)$ alkoxy;

m is 0, 1, 2, 3, 4 or 5;

$R^2$ is independently selected from a hydrogen, halogen, substituted or unsubstituted $(C_1-C_6)$alkyl, substituted or unsubstituted $(C_2-C_6)$alkenyl, substituted or unsubstituted $(C_2-C_6)$alkynyl, or substituted or unsubstituted $(C_1-C_6)$alkoxy;

n is 1 or 2;

$R^3$ is a substituted or unsubstituted $(C_1-C_6)$ aldehyde group,

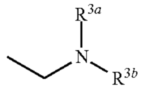

or

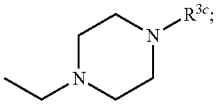

Wherein each $R^{3a}$, $R^{3b}$, $R^{3c}$ is independently selected from a hydrogen, substituted or unsubstituted $(C_1-C_6)$alkyl, substituted or unsubstituted $(C_2-C_6)$alkenyl, substituted or unsubstituted $(C_2-C_6)$alkynyl,

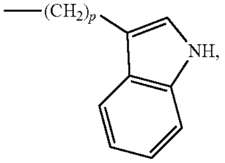

or and p is an integer of 1-3 (preferably, p is 2);

Wherein the compound of formula I does not include

AZ1

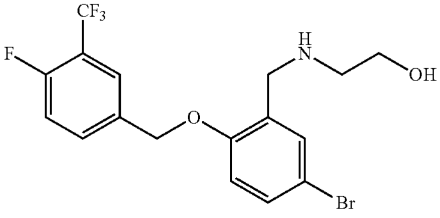

and

-continued

AZ2

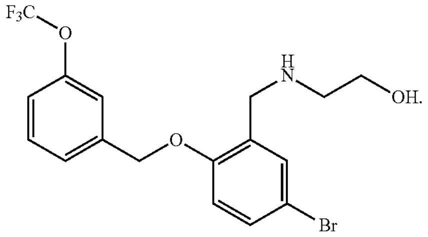

In a specific embodiment, the substitution position of $R^3$ on the benzene ring is the ortho position or the meta position; preferably, the ortho position.

In a preferred embodiment, $R^1$ is independently selected from a hydrogen, fluorine, chlorine, bromine or iodine (preferably fluorine), cyano, substituted or unsubstituted $(C_1\text{-}C_4)$alkyl, or substituted or unsubstituted $(C_1\text{-}C_4)$alkoxy.

In a preferred embodiment, each $R^1$ is independently selected from a fluorine, trifluoromethyl, or trifluoromethoxy.

In a preferred embodiment, $R^2$ is independently selected from a hydrogen, fluorine, chlorine, bromine or iodine (preferably bromine), substituted or unsubstituted $(C_1\text{-}C_4)$ alkyl, substituted or unsubstituted $(C_2\text{-}C_4)$alkenyl, substituted or unsubstituted $(C_2\text{-}C_4)$alkynyl, substituted or unsubstituted $(C_1\text{-}C_4)$alkoxy.

In a preferred embodiment, $R^2$ is independently selected from a hydrogen, fluorine, chlorine, bromine, methyl, ethyl, n-propyl, allyl, propargyl, $—OCH_2CH_2CH_3$, $—OCH_2CH_3$, $—OCH_3$, $—CHF_2$, $—CF_3$, $—OCHF_2$, or $—OCF_3$.

In a preferred embodiment, each $R^{3a}$, $R^{3b}$, $R^{3c}$ is independently selected from a hydrogen, substituted or unsubstituted $(C_1\text{-}C_4)$alkyl, substituted or unsubstituted $(C_2\text{-}C_4)$ alkenyl, substituted or unsubstituted $(C_2\text{-}C_4)$alkynyl.

In a preferred embodiment, the substituted $(C_1\text{-}C_4)$alkyl is independently selected from a hydroxyl$(C_1\text{-}C_4)$alkyl, $R^{4a}R^{4b}$ amino$(C_1\text{-}C_4)$alkyl or sulfhydryl$(C_1\text{-}C_4)$alkyl, and the $R^{4a}$ and Rob are independently a substituted or unsubstituted $(C_1\text{-}C_3)$alkyl; preferably a hydroxyl$(C_1\text{-}C_4)$alkyl, or $R^{4a}R^{4b}$ amino$(C_1\text{-}C_4)$alkyl.

In a preferred embodiment, the term "substituted" is halo, preferably fluoro.

In a specific embodiment, the compound of formula I is selected from the following compounds:

XMU1

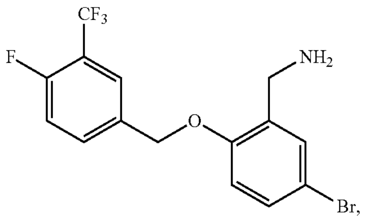

MZ39

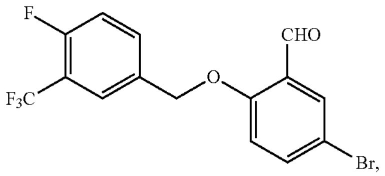

-continued (1) MZ3

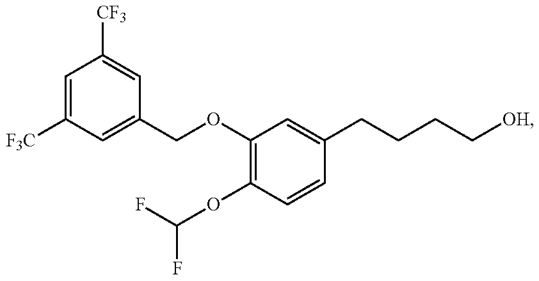

(2) MZ23

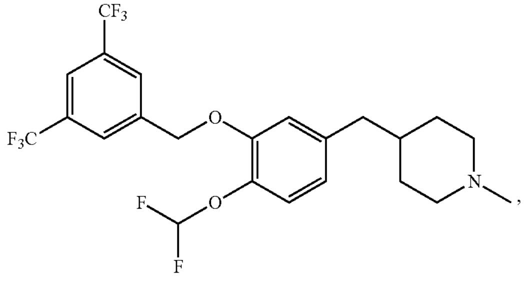

(3) MZ25

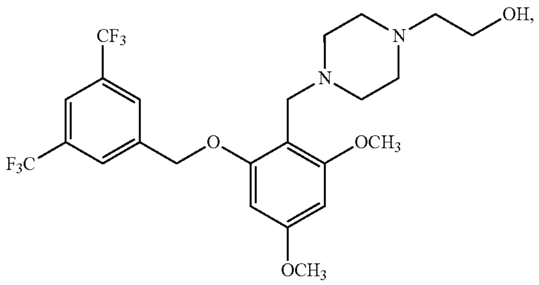

(4) MZ28

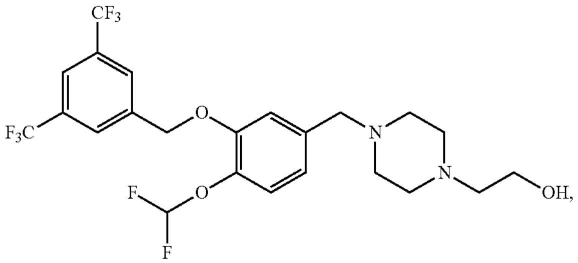

(5) MZ29

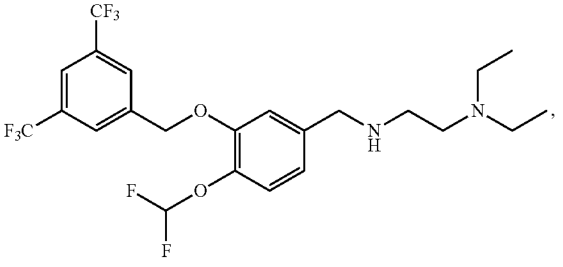

-continued
(6) MX24
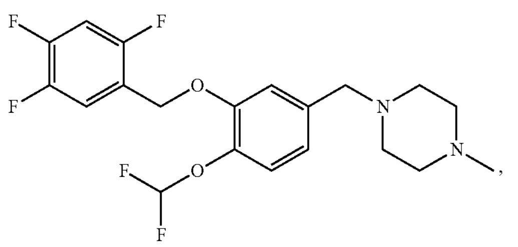
(7) MZ26
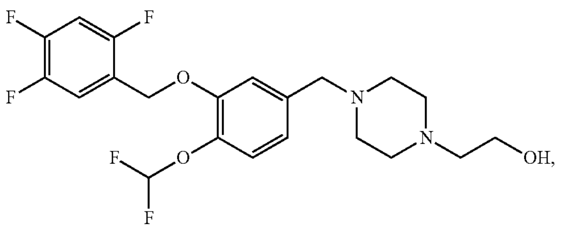
(8) MZ34
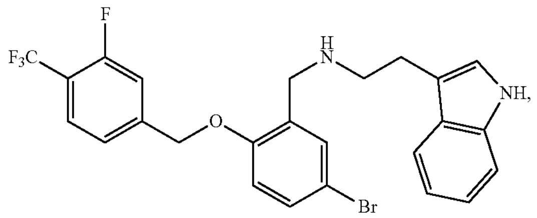
(9) MZ31
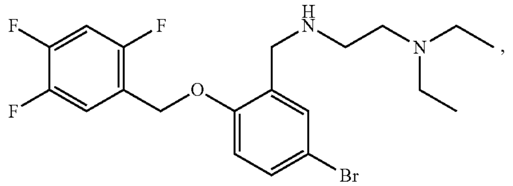
(10) MZ75
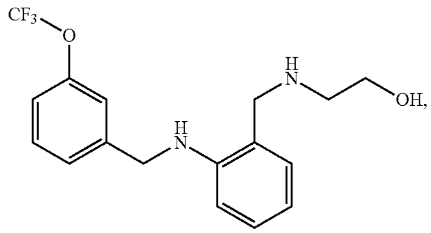
(11) MZ76
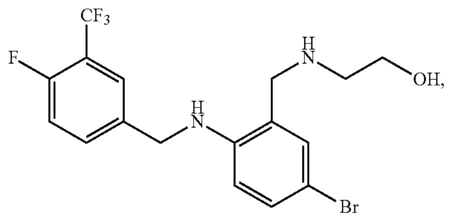
-continued
(12) MZ77
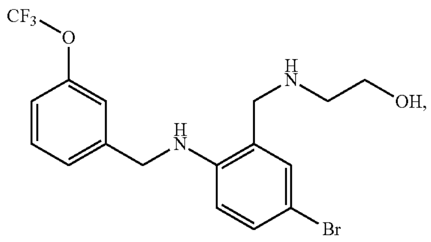
(13) MZ1
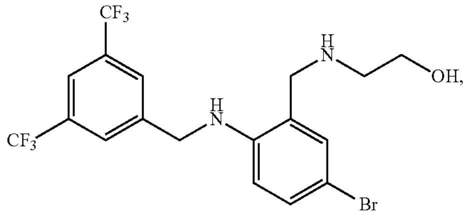
(14) MZ30
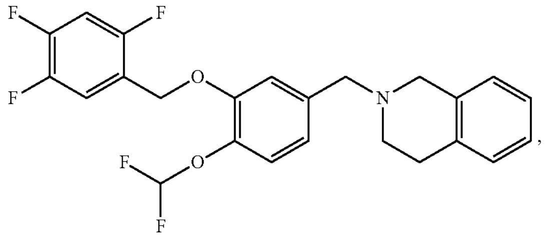
(15) MZ32
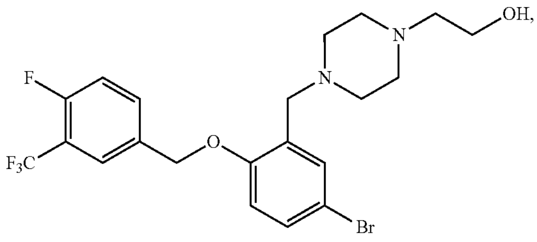
(16) MZ67
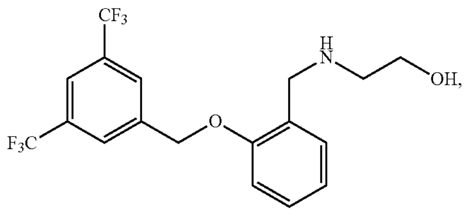
(17) MZ66
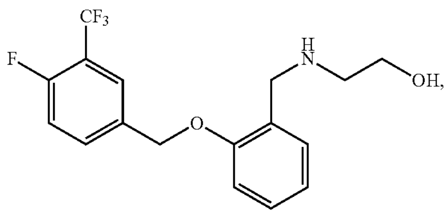

-continued
(18) MZ5
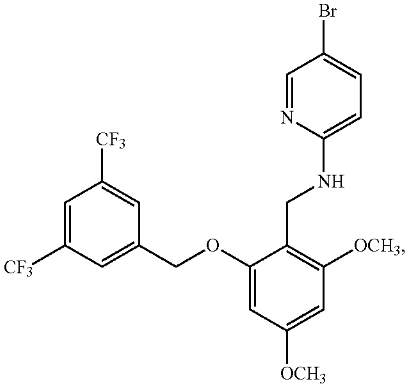
(19) MZ71
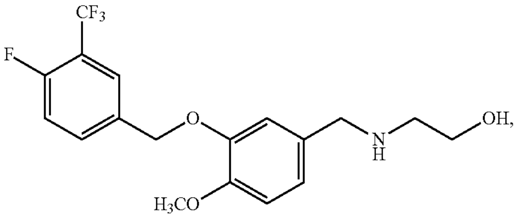
(20) MZ33
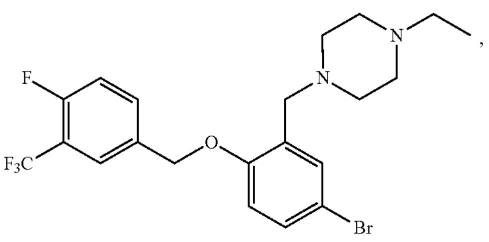
(21) MZ74
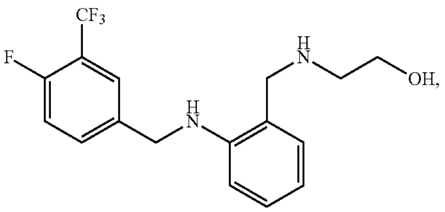
(22) MZ68
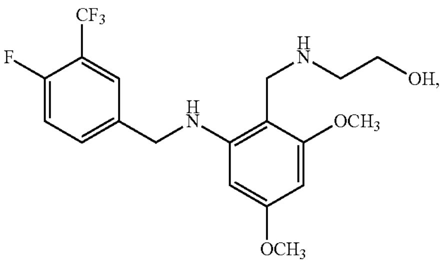
-continued
(23) MZ72
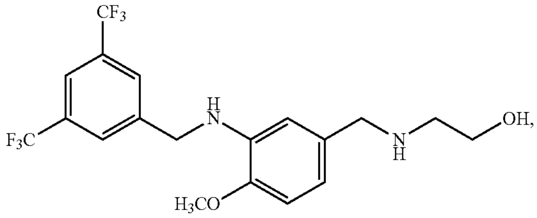
(24) MZ41
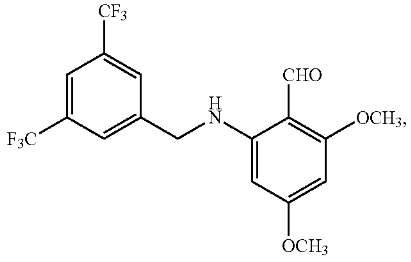
(25) MZ43
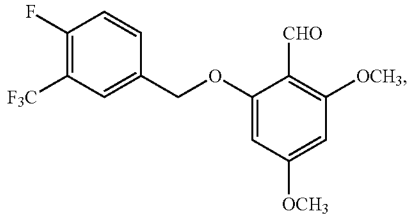
(26) MZ38
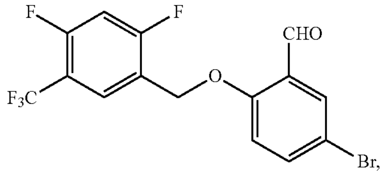
(27) MZ40
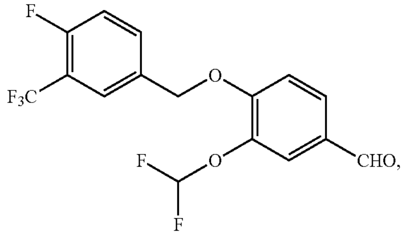
(28) MZ69
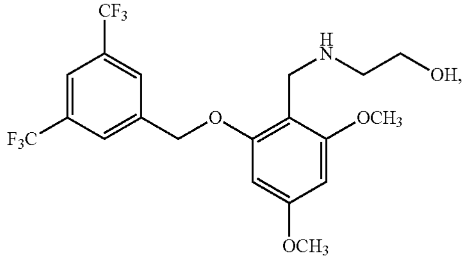

-continued

(29) MZ42

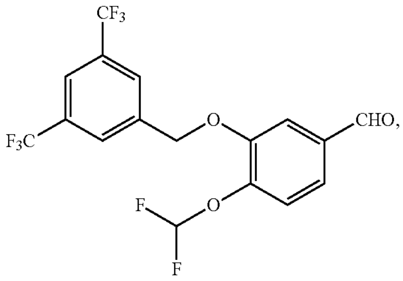

,

(30) MZ35

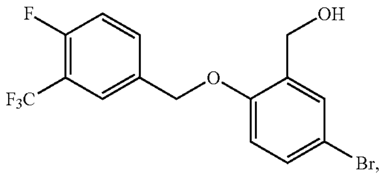

,

(31) MZ36

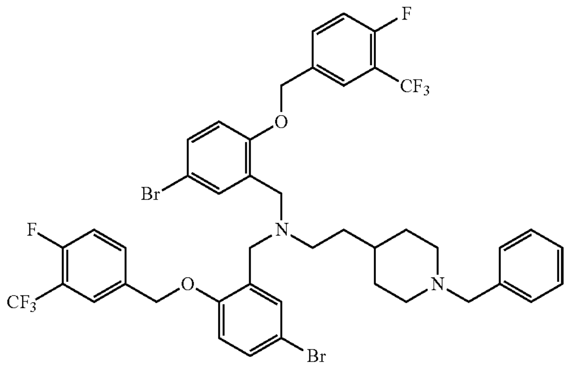

,

(32) MZ37

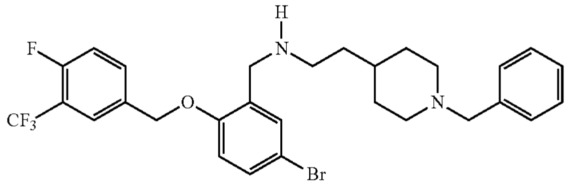

,

(33) MZ27

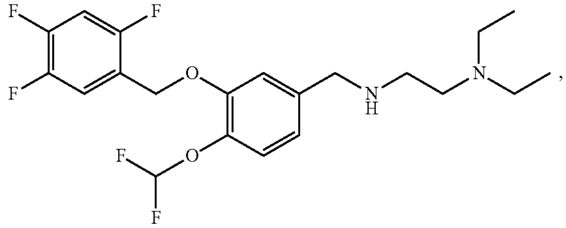

,

(34) MZ4

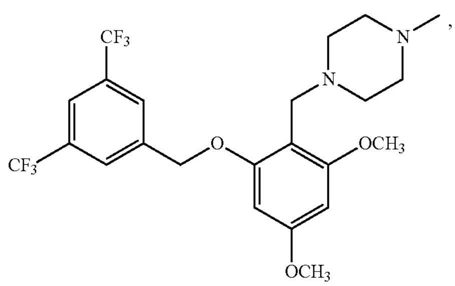

,

-continued

(35) MZ70

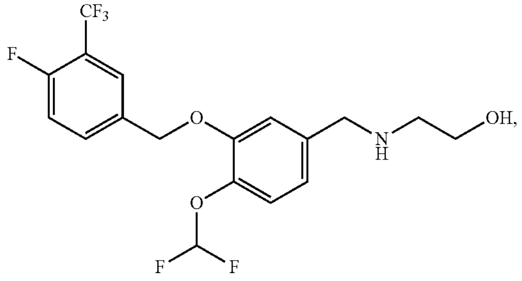

,

(36) MZ22

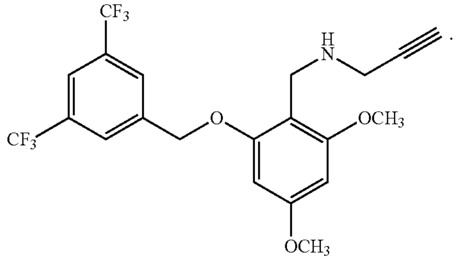

.

In a preferred embodiment, the compound of formula I is MZ77, MZ76, MZ1, MZ30, MZ32, MZ67, MZ66, MZ75, MZ31, MZ34, MZ74, MZ68, MZ29, MZ72, MZ38 or MZ24.

In a fourth aspect, the present invention provides a pharmaceutical composition comprising the compound of formula I described in the second aspect, various crystal forms, hydrates or solvates thereof, and optional pharmaceutically acceptable excipients.

In a preferred embodiment, the present invention provides a compound of formula I described in the second aspect, various crystal forms, hydrates or solvates thereof for preventing, treating or improving Alzheimer's disease or Down's syndrome.

In a preferred embodiment, the present invention provides a method for preventing, treating or improving Alzheimer's disease or Down's syndrome, comprising a step of administering the compound of formula I, various crystal forms, hydrates or solvates thereof to a subject in need thereof.

In a preferred embodiment, the present invention provides a drug comprising a compound of formula I, various crystal forms, hydrates or solvates thereof for preventing, treating or improving Alzheimer's disease or Down's syndrome.

It should be understood that, within the scope of the present invention, each technical feature of the present invention described above and in the following (as examples) may be combined with each other to form a new or preferred technical solution, which is not listed here due to space limitations.

MODES FOR CARRYING OUT THE INVENTION

Figure 1:
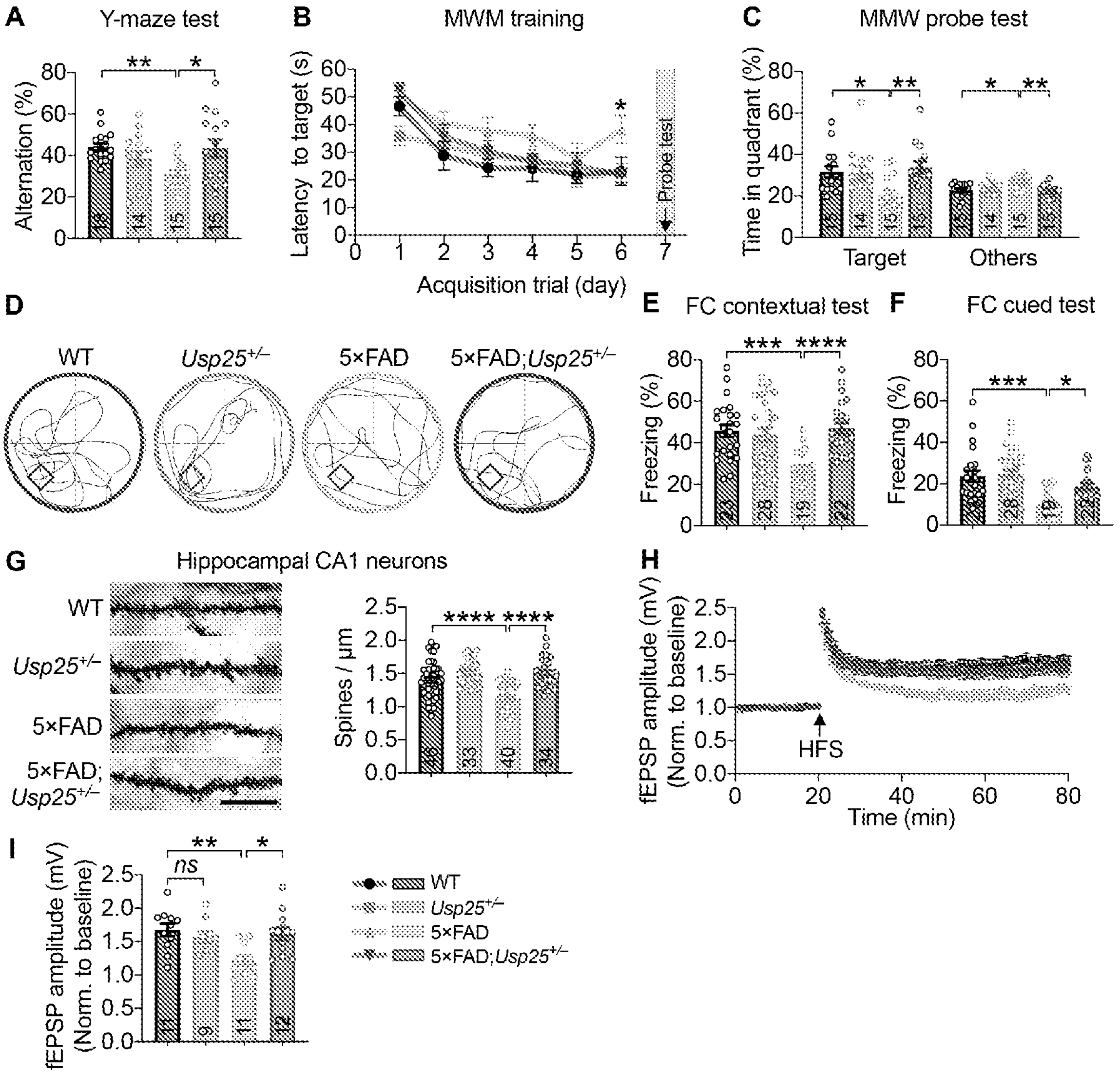
FIG. 1 is a schematic diagram showing that knockout of Usp25 enhances synaptic and cognitive function in AD mice; wherein (A-F) are the behavioral analysis results of 6-7 months old WT, $Usp25^{+/-}$, 5×FAD, 5×FAD; $Usp25^{+/-}$ mice. (A) Analysis results of the percentage of spontaneous alternations in the Y-maze test (Alternation %). n=14~18 mice per group. (B) Latency to target of mice during Morris water maze (MWM) training. (C) Analysis results of the percentage of time in the target quadrant and other quadrants of the mice during the test period of the Morris water maze platform. n=14-15 mice per group. (D) Schematic diagram of the swimming trajectories of mice in the Morris water maze platform test. (E) Analysis results of the percentage of time of mice freezing behavior (Freezing %) in Fear conditioned (FC) scene-related memory test. (F) Analysis results of the percentage of time of mice freezing behavior (Freezing %) in Fear conditioned (FC) cue-related memory test. n=19-28 mice per group. (G) Representative graph of Golgi staining in hippocampus of 9-month-old mice and analysis results of dendritic spine density. Scale bar, 10 μm. n=4 mice per group, 33-46 dendrites. (H) Long-term potentiation (LTP) recording results in CA1 region of hippocampal slices of 6-7 month old mice. (I) Statistical analysis of fEPSP amplitudes in the last 10 min of LTP recordings. WT (n=6 mice/11 brain slices), $Usp25^{+/-}$ (n=5 mice/9 brain slices), 5×FAD (n=5 mice/11 brain slices), 5×FAD; $Usp25^{+/-}$ (n=6 mice/12 brain slices). Data in Figures (A, C, E, F, G, I) were statistically analyzed by Kruskal-Wallis test, and data in Figure (B) were statistically analyzed by repeated-measures ANOVA. ns, no significant difference, P>0.05; *P<0.05; P<0.01; *P<0.001; and ****P<0.001.

After extensive and in-depth research, the inventors have unexpectedly discovered a series of compounds capable of preventing, treating or ameliorating Alzheimer's disease and Down's syndrome, especially preventing, treating or ameliorating cognitive impairment caused by Alzheimer's disease and Down's syndrome. Most of the compounds found in the present invention have completely new structures, thereby laying a new material basis for the development of drugs for preventing, treating or improving Alzheimer's disease and Down's syndrome. The present invention has been completed on this basis.

Definition

Unless otherwise defined, all technical and scientific terms used herein have the same meaning as commonly understood by those skilled in the art of the disclosed invention belongs. For clarity, some terms of the present invention are defined below.

The term "said" is intended to include "at least one" or "one or more."

If substituents are described as being "independently selected from" a group, each substituent is selected independently of the other. Therefore, each substituent may be the same as or different from another (other) substituent.

Unless otherwise indicated, "treating" as used herein means reversing, alleviating, inhibiting, or preventing the progression of, or one or more symptoms of, a disorder or condition to which such terms apply. Unless otherwise indicated, the term "treating" as used herein refers to the act of "treating" as defined immediately above. The term "treatment" also includes adjuvant and neoadjuvant therapy treatment of an individual.

As used herein, an expression, such as "$C_{1-n}$", means that a group has 1-n carbon atoms. For example, the expression "$C_{1-6}$" means that a group has 1, 2, 3, 4, 5 or 6 carbon atoms; and similarly, "$C_2$-$C_6$" means that a group has 2, 3, 4, 5 or 6 carbon atoms.

In various parts of the present specification, substituents of the compounds disclosed in the present invention are disclosed in terms of group type or scope. Specifically, the present invention includes each and every independent sub-combination of each member within these group species and ranges. For example, the term "$C_1$-$C_6$ alkyl" specifically refers to independently disclosed methyl, ethyl, $C_3$ alkyl, $C_4$ alkyl, $C_5$ alkyl and $C_6$ alkyl.

The term "alkyl" as used herein has the same meaning as commonly understood by a skilled person, and refers to various saturated or unsaturated linear, pendant or cyclic hydrocarbon groups. For example, alkyls as used herein refer to lower alkyls of 1-6 carbon atoms; preferably, lower alkyls of 1-4 carbon atoms. In a specific embodiment, alkyls described herein include, but are not limited to, methyl, ethyl, propyl, isopropyl, butyl, isobutyl, sec-butyl, tert-butyl, pentyl, hexyl, and the like.

The term "$C_{1-6}$ alkoxy" as used herein has the same meaning as commonly understood by a skilled in the art, and refers to a straight or branched chain alkoxy having 1 to 6 carbon atoms, including but not limited to methoxy, ethoxy, propoxy, isopropoxy and butoxy, etc.

The term "halogen" as used herein refers to F, Cl, Br or I.

Based on the teachings of the present invention and common knowledge in the art, a skilled person will know that the compounds of the present invention and the various substituents defined above can be further substituted, for example, by a halogen, nitro, amino, hydroxyl, etc., so long as the desired combination of substituents is a stable or chemically achievable combination of substituents.

As used herein, the term "substituted" means that one or more hydrogen atoms on a particular group are replaced by a specific substituent. The specific substituent may be a substituent described in the forgoing, or may be a specific substituent found in the various examples or a conventional substituent in the art. Therefore, in the present invention, the substituents in formula I can also be the corresponding groups in the specific compounds in the examples independently; that is, not only the combination of the substituents in the above formula I, but also the combination of some substituents shown in formula I and other specific substituents appearing in the Examples are included in the present invention.

"Pharmaceutically acceptable" as used herein refers to compounds, raw materials, compositions and/or dosage forms that, within the scope of sound medical judgment, are suitable for the contact with patient tissue without excessive toxicity, irritation, allergies or other problems and complications commensurate with a reasonable benefit/risk ratio and are effective for the intended use.

As used herein, "pharmaceutically acceptable salts" refer to organic and inorganic salts of the compounds of the present invention. Pharmaceutically acceptable salts are well known in the art, pharmaceutically acceptable non-toxic acid salts include, but are not limited to, inorganic acid salts such as hydrochloride, hydrobromide, phosphorates, sulfates, perchlorates, and organic acid salts such as acetates, oxalates, maleates, tartrates, citrates, succinates, malonates, or such salts can be obtained by other methods described in literatures, such as ion exchange method. Other pharmaceutically acceptable salts of non-toxic acids, including adipate, alginate, ascorbate, aspartate, besylate, benzoate, bisulfate, borate, butyrate, camphorate, camphorsulfonate, cyclopentylpropionate, digluconate, lauryl sulfate, ethanesulfonate, formate, fumarate, glucoheptonate, glycerophosphate, gluconate, hemisulfate, heptanoate, caproate, hydroiodide, 2-hydroxy-ethanesulfonate, lacturonate, lactate, laurate, lauryl sulfate, malate, malonate, methanesulfonate, 2-naphthalenesulfonate, nicotinate, nitrate, oleate, palmitate, pectate, persulfate, 3-phenylpropionate, picrate, pivalate, propionate, stearate, thiocyanate, p-toluenesulfonate, undecanoate, valerate, etc. Pharmaceutically acceptable salts obtained from appropriate bases include alkali metal salts, alkaline earth metal salts. Alkali or alkaline earth metal salts, include sodium, lithium, potassium, calcium, magnesium, and the like. The present invention also contemplates quaternary ammonium salts formed from any compound containing an N-group. Water- or oil-soluble or dispersible products can be obtained by quaternization. Pharmaceutically acceptable salts further include appropriate, non-toxic ammonium, quaternary ammonium salts and amine cations formed with anti-counterions, such as halides, hydroxides, carboxylates, sulfates, phosphates, nitrates, $C_1$-$C_8$ sulfonates and aromatic sulfonates.

A skilled person will recognize that the chemical reactions described herein can be used to suitably prepare many other compounds of the present invention, and that other methods for preparing the compounds of the present invention are considered to be within the scope of the present invention Inside. For example, the synthesis of those non-exemplified compounds according to the present invention can be successfully accomplished by a skilled person by modifying methods, such as appropriate protection of interfering groups, by using other known reagents in addition to those described herein, or by routinely modifying reaction conditions. In addition, the reactions disclosed herein or known reaction conditions are also acknowledged to be applicable to the preparation of other compounds of the present invention.

For convenience and in line with conventional understanding, the terms "optionally substituted" or "substituted or unsubstituted" apply only to sites that can be substituted by substituents, and do not include those chemically unrealizable replace.

Compounds of the Present Invention

The present invention provides compounds capable of preventing, treating or ameliorating Alzheimer's disease and Down's syndrome, in particular preventing, treating or ameliorating cognitive impairment caused by Alzheimer's disease and Down's syndrome. The results of the experiments confirmed that the compounds of the present invention can significantly improve the learning and memory impairment and synaptic function defects in the Alzheimer's disease 5×FAD mouse model, and can inhibit neuroinflammationby reducing the number and activation state of the microglia in the cerebral cortex and hippocampus, to exert its anti-Alzheimer's disease and related diseases.

Compared with other clinically applied drugs, the compound of the invention has simple structure, clear efficacy, easy synthesis and preparation, can effectively pass through the blood-brain barrier, can effectively improve the synaptic function and learning and memory deficits in Alzheimer's disease and Down's syndrome mouse models, and will not produce other adverse reactions at a higher dose. Therefore, it has good safety, and can be used in the treatment of Alzheimer's disease and Down's syndrome.

In a specific embodiment, the present invention provides a compound of formula I, various crystal forms, hydrates, solvates or pharmaceutically acceptable salts thereof,

I

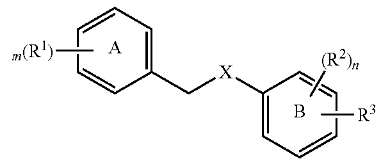

Wherein each substituent in formula I is as described above.

In particular, the present invention provides following compounds:

AZ1

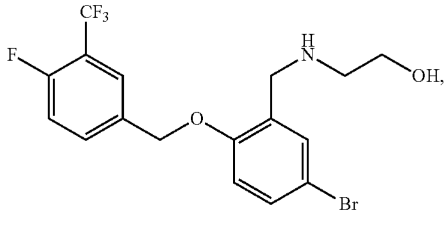

AZ2

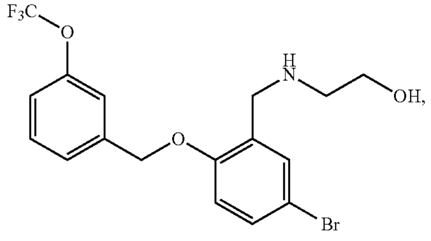

-continued
XMU1
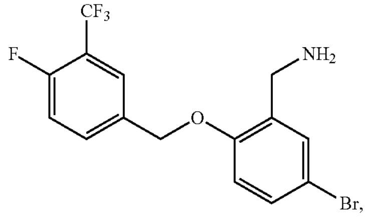
MZ39
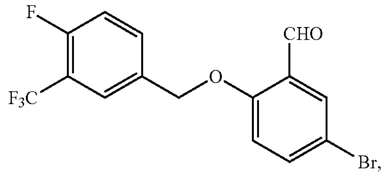
(1) MZ3
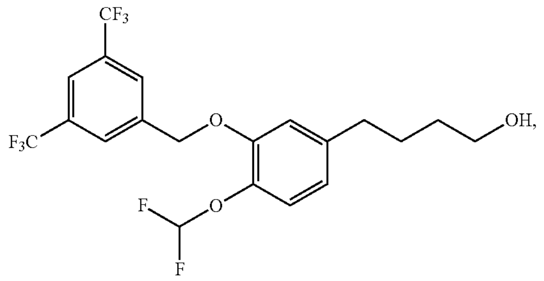
(2) MZ23
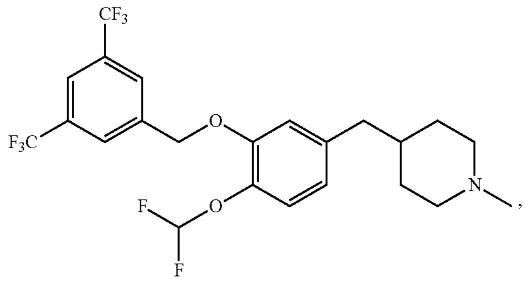
(3) MZ25
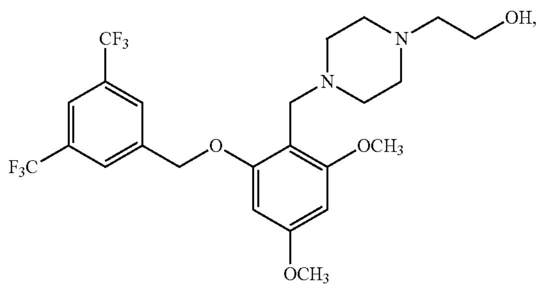
(4) MZ28
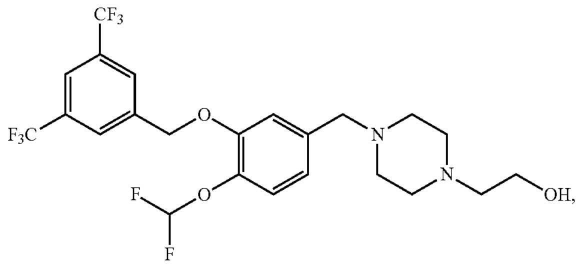
-continued
(5) MZ29
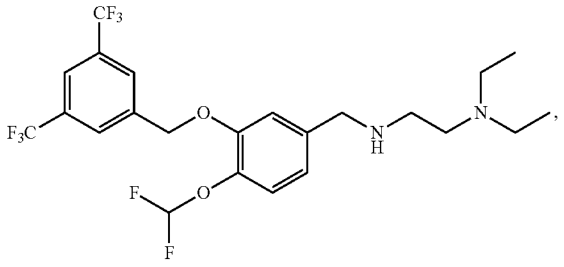
(6) MX24
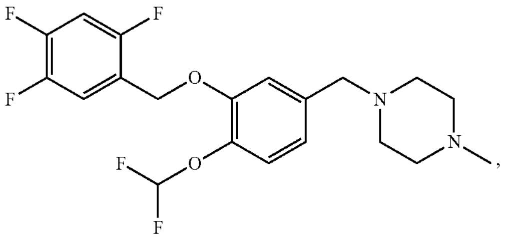
(7) MZ26
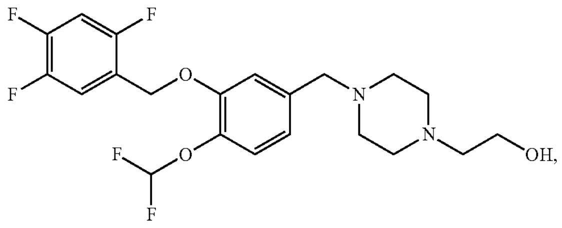
(8) MZ34
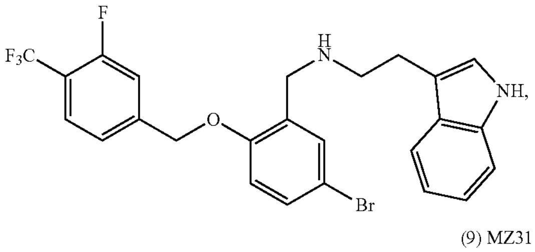
(9) MZ31
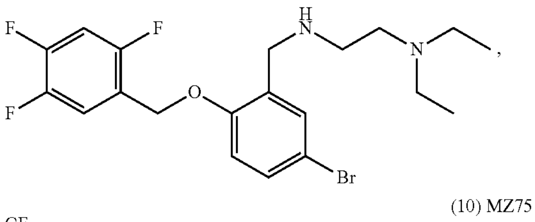
(10) MZ75
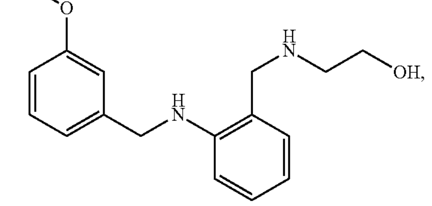

-continued
(11) MZ76
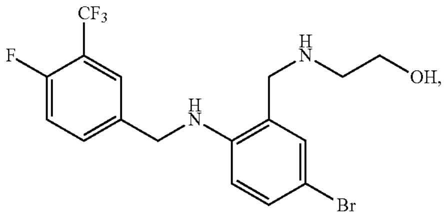
(12) MZ77
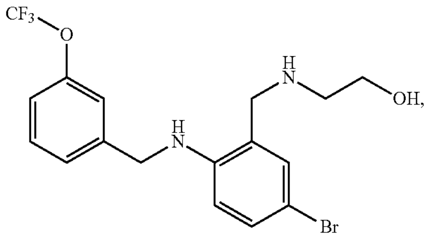
(13) MZ1
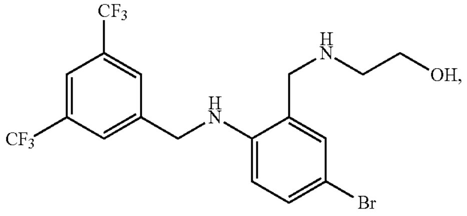
(14) MZ30
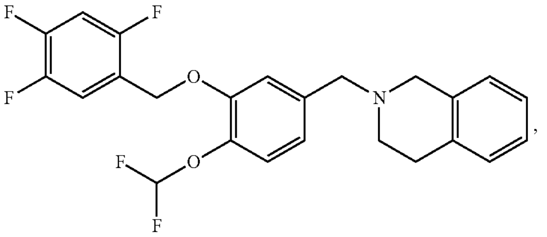
(15) MZ32
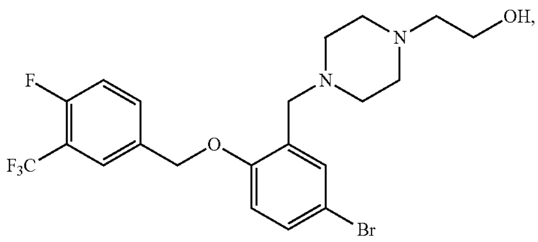
(16) MZ67
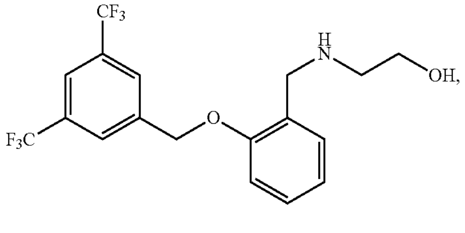
-continued
(17) MZ66
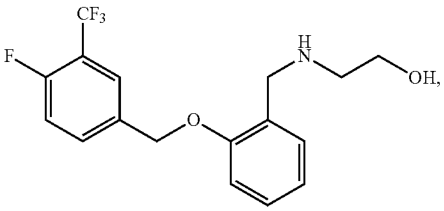
(18) MZ5
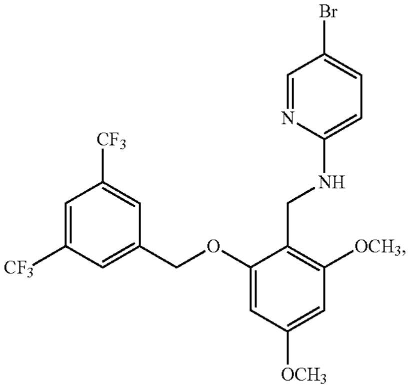
(19) MZ71
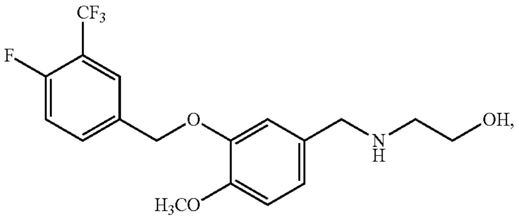
(20) MZ33
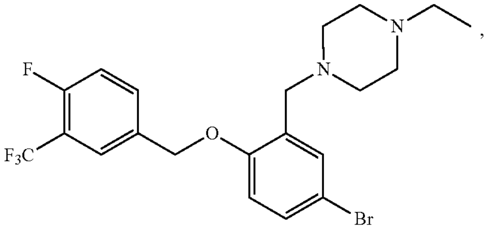
(21) MZ74
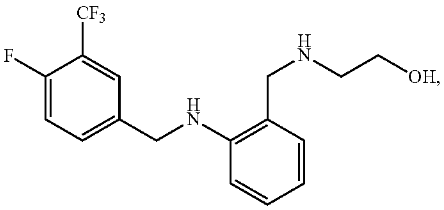

-continued
(22) MZ68
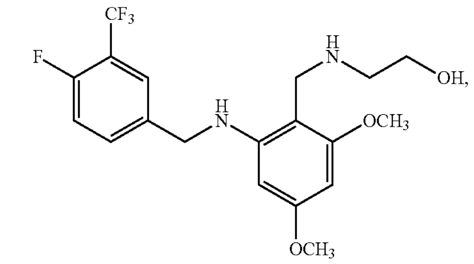
(23) MZ72
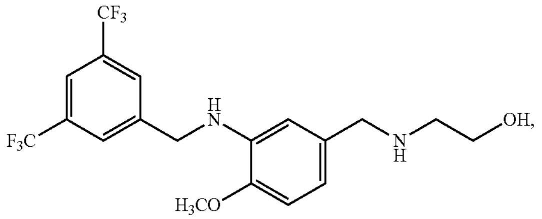
(24) MZ41
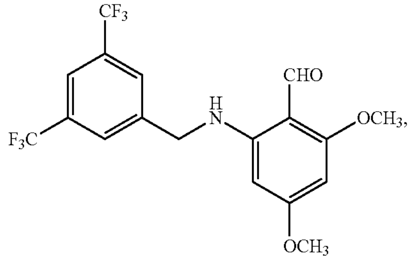
(25) MZ43
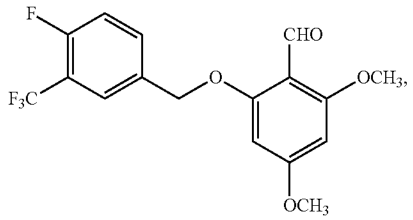
(26) MZ38
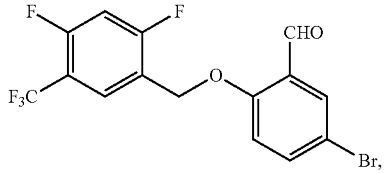
(27) MZ40
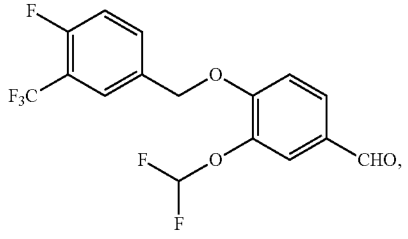
-continued
(28) MZ69
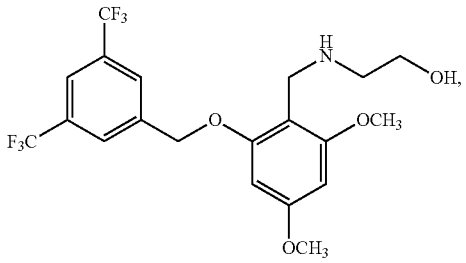
(29) MZ42
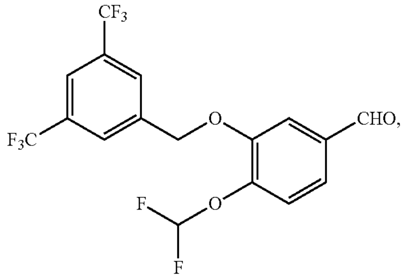
(30) MZ35
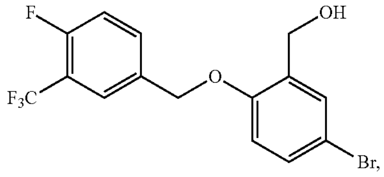
(31) MZ36
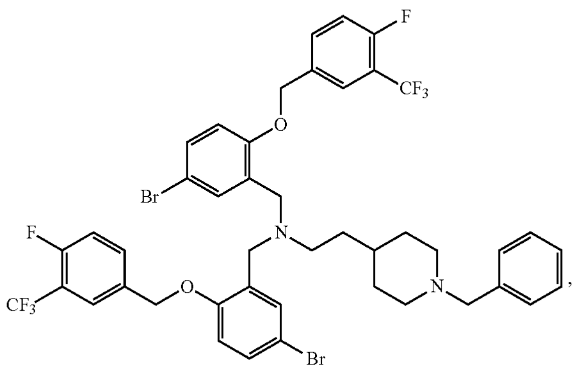
(32) MZ37
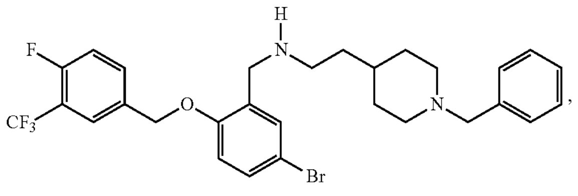
(33) MZ27
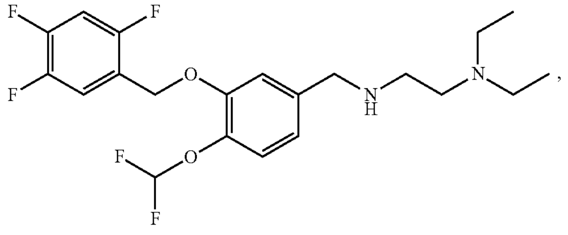

-continued

(34) MZ4

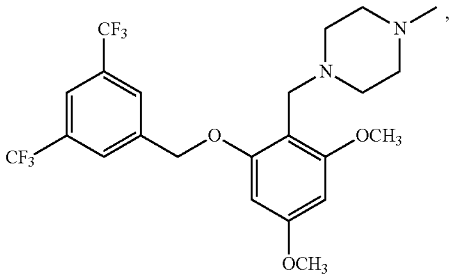

(35) MZ70

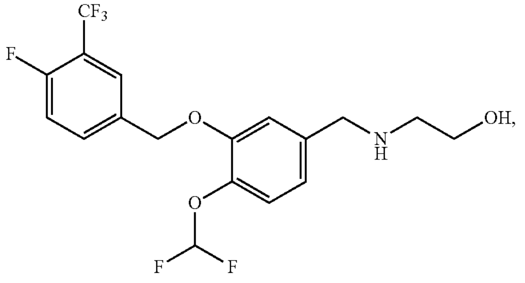

(36) MZ22

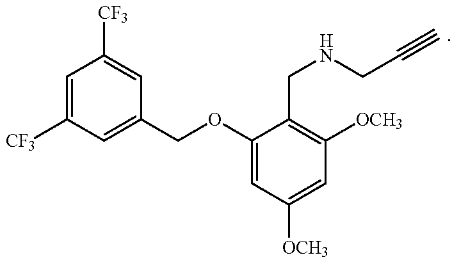

In a specific embodiment, the compound of the present invention is AZ1, AZ2, MZ77, MZ76, MZ1, MZ30, MZ32, MZ67, MZ66, MZ75, MZ31, MZ34, MZ74, MZ68, MZ29, MZ72, MZ38 or MZ24.

Pharmaceutical Composition of the Present Invention and Methods of Administration Thereof The compounds of the present invention can be used for preventing, treating or ameliorating Alzheimer's disease and Down's syndrome, especially preventing, treating or ameliorating cognitive impairment caused by Alzheimer's disease and Down's syndrome. Therefore, based on the compounds of the present invention and various crystal forms, hydrates, solvates or pharmaceutically acceptable salts thereof, the present invention also provides a pharmaceutical composition comprising the compound of the present invention, and the pharmaceutical composition optionally including pharmaceutically acceptable excipients.

In a specific embodiment, the pharmaceutical composition of the present invention comprises a compound of the present invention or a pharmaceutically acceptable salt thereof in a safe and effective amount and a pharmaceutically acceptable excipient or carrier. The "safe and effective amount" refers to: the amount of the compound is sufficient to significantly improve the condition without causing serious side effects.

The "pharmaceutically acceptable carrier" refers to one or more compatible solid or liquid filler or gel materials which are suitable for human use and which must be of sufficient purity and sufficiently low toxicity. "Compatibility" as used herein means that the components of the composition are capable of intermixing with each other and between the compounds of the present invention without significantly reducing the efficacy of the compounds. Examples of pharmaceutically acceptable carrier include cellulose and its derivatives (such as sodium carboxymethylcellulose, sodium ethylcellulose, cellulose acetate, etc.), gelatin, talc, solid lubricant (such as stearic acid, magnesium stearate), calcium sulfate, vegetable oil (such as soybean oil, sesame oil, peanut oil, olive oil, etc.), polyol (such as propylene glycol, glycerol, mannitol, sorbitol, etc), emulsifiers (e.g., Tween®), wetting agents (e.g., sodium lauryl sulfate), colorants, flavors, stabilizers, antioxidants, preservatives, pyrogen-free water, etc.

The mode for administering the compound or pharmaceutical composition of the present invention is not particularly limited, and representative modes of administration include, but are not limited to, oral, parenteral (intravenous, intramuscular, or subcutaneous) administration.

Solid dosage forms for oral administration include capsules, tablets, pills, powders, and granules. In these solid dosage form, the active compound is mixed with at least one conventional inert excipient (or carry), such as sodium citrate or dicalcium phosphate, or with the following ingredients: (a) fillers or compatibilizer, for example, starch, lactose, sucrose, glucose, mannitol and silicic acid; (b) binder such as hydroxymethylcellulose, alginates, gelatin, polyvinylpyrrolidone, sucrose, and acacia; (c) humectant such as glycerin; (d) disintegrants such as agar, calcium carbonate, potato or tapioca starch, alginic acid, certain complex silicates, and sodium carbonate; (e) slow solvents such as paraffin; (f) absorption accelerator such as quaternary ammonium compounds; (g) wet agents such as cetyl alcohol and glyceryl monostearate; (h) adsorbents such as kaolin; and (i) lubricants such as talc, calcium stearate, magnesium stearate, solid polyethylene glycol, sodium lauryl sulfate, or mixture thereof. In the case of capsules, tablets and pills, the dosage form may also contain a buffering agent.

Solid dosage forms, such as tablets, dragees, capsules, pills and granules may be prepared using coating and shell materials, such as enteric coatings and other materials known in the art. An opacifying agent can be contained and the active compound or the compounds in such compositions can be released in a certain part of the digestive tract in a delayed manner. Examples of embedding components that can be used are polymeric materials and wax-like materials. If desired, the active compounds can also be formed into microcapsules with one or more of the above-mentioned excipients.

Liquid dosage forms for oral administration include pharmaceutically acceptable emulsions, solutions, suspensions, syrups, or tinctures. In addition to the active compound, liquid dosage forms may contain inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, in particular cottonseed oil, peanut oil, corn germ oil, olive oil, castor oil and sesame oil or mixtures of these or the like.

In addition to these inert diluents, the compositions may also contain adjuvants, such as wetting agents, emulsifying and suspending agents, sweetener, flavoring agents and spices.

In addition to the active compound, the suspension may comprise suspending agents, such as ethoxylated isostearyl alcohol, polyoxyethylene sorbitol and sorbitan esters, microcrystalline cellulose, aluminum methoxide and agar or mixtures thereof, and the like.

A composition for parenteral injection may comprise a physiologically acceptable sterile aqueous or anhydrous solution, dispersion, suspension or emulsion, and a sterile powder for reconstitution into a sterile injectable solution or dispersion. Suitable aqueous and non-aqueous carriers, diluents, solvents or excipients include water, ethanol, polyols and suitable mixtures thereof.

Dosage forms for topical administration of the compounds of the present invention include ointments, powders, patches, sprays and inhalants. The active ingredient is mixed under sterile conditions with a physiologically acceptable carrier and any preservatives, buffers, or propellants that may be required if necessary.

The compounds of the present invention may be administered alone or in combination with other pharmaceutically acceptable compounds. When the pharmaceutical compositions is used, a safe and effective amount of a compound of the present invention is administered to a mammal in need of treatment, such as a human, at a dose that is considered pharmaceutically effective for administration. The compound and pharmaceutical composition of the present invention can be administered by oral, nasal, dermal, pulmonary or gastrointestinal routes of administration. Preferably, it is taken orally in a single dose or in divided doses. Regardless of the method of administration, the optimal dose for an individual will depend on the specific treatment. It is common to start with a small dose and gradually increase the dose until the most suitable dose is found. Of course, the specific dosage should also take into account the route of administration, patient health and other factors, which are within the skills of skilled physicians.

Main Advantages of the Present Invention:

1. The present invention provides compounds with novel structures for preventing, treating or improving Alzheimer's disease and Down's syndrome, in particular preventing, treating or improving the cognitive impairment caused by Alzheimer's disease and Down's syndrome;
2. The compound of the invention has the advantages of simple structure, clear efficacy and easy synthesis and preparation;
3. The compound of the present invention can effectively pass through the blood-brain barrier;
4. The compounds of the present invention will not produce other adverse reactions when applied in larger doses, therefore, have good safety.

The present invention will be further described below with reference to specific examples. It should be understood that these examples are merely illustrative of the invention and are not intended to limit the scope of the invention. In the following examples, the test method without specifying the specific conditions is usually based on the conventional conditions or the conditions recommended by the manufacturer. Percentages and parts are percentages and parts by weight, unless otherwise indicated. The experimental materials and reagents used in the following examples are commercially available unless otherwise specified.

The used chromatographic column in the following Examples is a silica gel column, and silica gel is (200-300 mesh).

$^1$H NMR was recorded using a Bruker 400 MHz magnetic resonance spectrometer. $^1$H NMR spectra were performed with $CDCl_3$ as solvent (in ppm) and TMS (0 ppm) or chloroform (7.26 ppm) as reference standards. The following abbreviations are used when multiplets are present: s (singlet), d (doublet), t (triplet), q (quartet), m (multiplet) peak), dd (doublet of doublets), ddd (doublet of doublet of doublets), dt (doublet of triplets), td (triplet of doublets), tt (triplet of triplets, triple triplet). The coupling constant, J, is expressed in Hertz (Hz).

Compounds AZ1 and AZ2 are commercially available drugs, and can also be synthesized according to a prior art literature, such as Wrigley, et al., ACS Chem. Biol. 2017.

Example 1. Preparation of Compound XMU1

XMU1

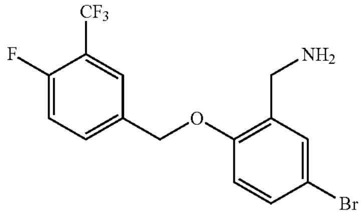

Step 1) Under nitrogen protection, potassium carbonate (2.93 g, 21.22 mmol), 4-(bromomethyl)-1-fluoro-2-(trifluoromethyl)benzene (3 g, 11.67 mmol) and 5-bromo-2-hydroxybenzaldehyde (2.13 g, 10.61 mmol) were added to the 250 ml there-neck flask successively, then 60 ml of DMF was added, and magnetically stirred at room temperature 25° C. to obtain a suspension, which was stirred at room temperature overnight (about 15 hours). The next day, the raw materials disappeared as being TLC-monitored, and the reaction was terminated. The reaction solution was poured into 1.2 L ice water, there were white precipitates, and the obtained white solids were filtered, washed with 3×500 ml of water, and dried in vacuo to obtain 5-bromo-2-(4-fluoro-3-(trifluoromethyObenzyloxy)benzaldehyde (3.5 g, 87.46%) as white solids (as shown in the following reaction formula):

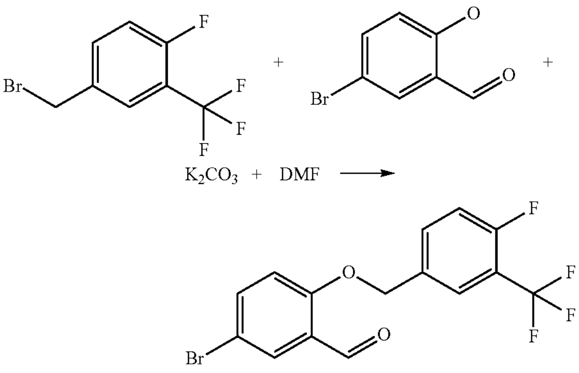

Step 2) Under nitrogen protection, 5-bromo-2-(4-fluoro-3-(trifluoromethyl)benzyloxy)benzaldehyde (3 g, 7.95 mmol) was added into a 250 ml bottle, 1.0 M solution in $NH_3$/THF (80 mL) was added, and then the solution was stirred for 10 mins. Then sodium triacetylborohydride (6.74 g, 31.82 mmol) was added portionwise over approximately 30 minutes. Upon addition, the resulting suspension was stirred at 20° C. for 16 hours. The reaction was monitored by TLC, and quenched after the starting material disappeared.

The mixture was poured into 10% $NaHCO_3$ solution (200 mL) and phases were extracted with ethyl acetate (2×200 mL). Organic phases were combined, dried over sodium sulfate, filtered, and evaporated in vacuo to remove the solvent so as to give a yellow gum. The crude product was purified by flash chromatography on silica gel with an eluting gradient of 0-10% methanol in dichloromethane. The pure fractions were combined and evaporated to dryness to give (5-bromo-2-((4-fluoro-3-(trifluoromethyl)benzyl)oxy)phenyl)methanamine (2 g, 66.48%) as a white solid, namely XMU1 (as shown in the following reaction formula):

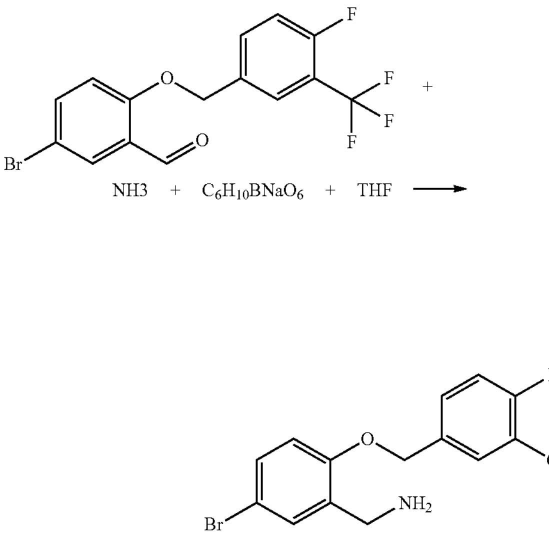

$^1$H-NMR (DMSO-d6, 400 MHz): 7.88-7.72 (m, 2H), 7.62-7.48 (m, 2H), 7.42 (d, J=7.6 Hz, 1H), 6.97 (d, J=8.8 Hz, 1H), 5.17 (s, 2H), 3.68 (s, 2H), 1.75 (brs, 2H).

Example 2. Preparation of Compound MZ39

MZ39

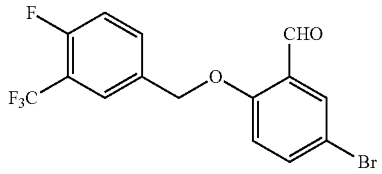

4-fluoro-3-trifluoromethylbenzyl bromide (0.18 mL, 1.2 mmol), 5-bromosalicylaldehyde (0.20 g, 1 mmol), potassium carbonate (0.41 g, 3 mmol), DMF (10 mL) were added in a 100 ml single-neck round-bottom flask, reacted at room temperature for 6 h, and extracted with ethyl acetate. Organic phases were combined, concentrated under a reduced pressure, and then purified with silica gel column to obtain a white solid (0.28 g, 74.2%).

1H NMR (400 MHz, $CDCl_3$) δ 10.42 (s, 1H), 7.95-7.92 (m, 2H), 7.86 (s, 1H), 7.17 (d, J=8.1 Hz, 1H), 7.07 (d, J=1.9 Hz, 1H), 6.96 (dd, J=8.2, 1.9 Hz, 1H), 6.53 (t, J=74.3 Hz, 1H), 5.23 (s, 2H);

MS (ESI): m/z 376.98 $[M+H]^+$.

Example 3. Preparation of Compound (1)

(1) MZ3

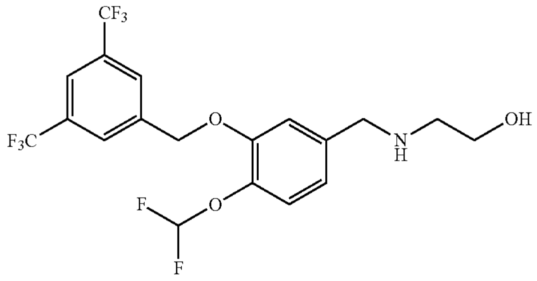

Step 1) 3,5-bistrifluoromethylbenzyl bromide (0.22 mL, 1.2 mmol), 4-difluoromethoxy-3-hydroxybenzaldehyde (0.13 g, 1 mol), potassium carbonate (0.41 g, 3 mmol), DMF (10 mL) were successively added to a 100 ml single-neck round-bottom flask, reacted at room temperature for 6 h, and extracted with ethyl acetate. Organic phases were combined, concentrated under a reduced pressure, and then purified by silica gel column to obtain a white solid (0.37 g, 89.3%).

$^1$H NMR (400 MHz, $CDCl_3$) δ 9.95 (s, 1H), 7.94 (s, 2H), 7.88 (s, 1H), 7.58 (d, J=1.8 Hz, 1H), 7.55 (dd, J=8.1, 1.8 Hz, 1H), 7.39 (d, J=8.1 Hz, 1H), 6.65 (t, J=73.2 Hz, 1H), 5.29 (s, 2H).

MS (ESI): m/z 415.05 $[M+H]^+$;

Step 2) 4-difluoromethoxy-3-(3,5-bistrifluoromethylbenzyl)benzaldehyde (0.21 g, 0.5 mmol), ethanolamine (0.09 ml, 1.5 mmol), acetic acid (0.17 mL, 1.5 mmol)), and THF (10 mL) were added to a 100 mL three-neck round-bottom flask under nitrogen protection, and reacted at room temperature for 1 h. Sodium triacetoxyborohydride (0.33 g, 1.5 mol) was added, reacted for another 24 h, and extracted with ethyl acetate. A saturated sodium bicarbonate solution was added to adjust pH to weakly basic. Organic phases were combined, and purified by silica gel column chromatography to obtain an orange solid (0.20 g, 87.1%).

$^1$H NMR (400 MHz, $CDCl_3$) δ 7.95-7.92 (m, 2H), 7.86 (s, 1H), 7.17 (d, J=8.1 Hz, 1H), 7.07 (d, J=1.9 Hz, 1H), 6.96 (dd, J=8.2, 1.9 Hz, 1H), 6.53 (t, J=74.3 Hz, 1H), 5.23 (s, 2H), 3.80 (s, 2H), 3.71-3.65 (m, 2H), 2.82-2.79 (m, 2H).

MS (ESI): m/z 460.11 $[M+H]^+$.

Example 4. Preparation of Compound (2)

(2) MZ23

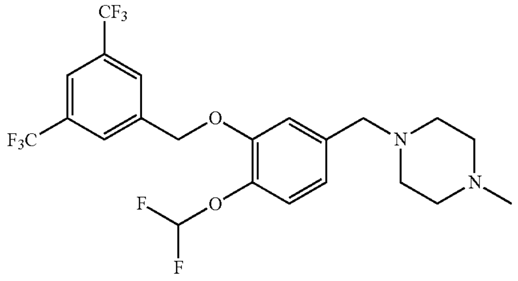

Step 1) 3,5-bistrifluoromethylbenzyl bromide (0.22 mL, 1.2 mmol), 4-difluoromethoxy-3-hydroxybenzaldehyde (0.13 g, 1 mol), potassium carbonate (0.41 g, 3 mmol), and DMF (10 mL) were successively added to a 100 ml single-neck round-bottom flask, reacted at room temperature for 6 h, and extracted with ethyl acetate. The organic phases were combined, concentrated under a reduced pressure, and then purified by silica gel column to obtain a white solid (0.37 g, 89.3%).

$^1$H NMR (400 MHz, $CDCl_3$) δ 9.95 (s, 1H), 7.94 (s, 2H), 7.88 (s, 1H), 7.58 (d, J=1.8 Hz, 1H), 7.55 (dd, J=8.1, 1.8 Hz, 1H), 7.39 (d, J=8.1 Hz, 1H), 6.65 (t, J=73.2 Hz, 1H), 5.29 (s, 2H).

MS (ESI): m/z 415.05 $[M+H]^+$;

Step 2) 4-difluoromethoxy-3-(3,5-bistrifluoromethylbenzyl)benzaldehyde (0.21 g, 0.5 mmol), N-methylpiperazine (0.17 mL, 1.5 mL), acetic acid (0.17 mL, 1.5 mmol), THF (10 mL) were successively added to a 100 mL three-neck round-bottom flask under a nitrogen protection, and reacted at room temperature for 1 h. Sodium triacetoxyborohydride (0.33 g, 1.5 mol) was added and reacted for another 24 h, and extracted with ethyl acetate. A saturated sodium bicarbonate solution was added to adjust pH to weakly alkaline. Organic phases were combined, and purified by silica gel column chromatography to obtain an oily liquid (0.17 g, 68.3%).

$^1$H NMR (400 MHz, $CDCl_3$) δ 7.92 (s, 2H), 7.85 (s, 1H), 7.14 (d, J=8.1 Hz, 1H), 7.05 (d, J=1.9 Hz, 1H), 6.93 (dd, J=8.2, 1.9 Hz, 1H), 6.53 (t, J=74.4 Hz, 1H), 5.23 (s, 2H), 3.45 (s, 2H), 2.42 (s, 8H), 2.28 (s, 3H).

MS (ESI): m/z 499.16 $[M+H]^+$.

Example 5. Preparation of Compound (3)

(3) MZ25

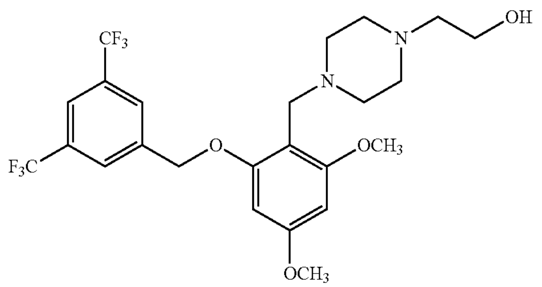

Step 1) 3,5-bistrifluoromethylbenzyl bromide (0.22 mL, 1.2 mmol), 4,6-dimethoxysalicylaldehyde (0.18 g, 1 mmol), potassium carbonate (0.41 g, 3 mmol), DMF (10 mL) was sequentially added to a 100 ml single-neck round-bottom flask, reacted at room temperature for 6 h, and extracted with ethyl acetate. The organic phases were combined, concentrated under a reduced pressure, and purified by silica gel column to obtain a white solid (0.44 g, 89.4%).

$^1$H NMR (400 MHz, $CDCl_3$) (δ 10.43 (s, 1H), 8.04 (s, 2H), 7.85 (s, 1H), 6.14 (d, J=2.1 Hz, 1H), 6.11 (d, J=2.1 Hz, 1H), 5.23 (s, 2H), 3.91 (s, 3H), 3.87 (s, 3H).

MS (ESI): m/z 409.08 $[M+H]^+$;

Step 2) 2-(3,5-bistrifluoromethylbenzyl)-4,6-dimethoxysalicylaldehyde (0.20 g, 0.49 mmol), 1-(2-hydroxyethyl) piperazine (0.18 mL), 1.5 mmol), acetic acid (0.17 mL, 1.5 mmol), THF (10 mL) were successively added to a 100 mL three-neck round-bottom flask under a nitrogen protection, and reacted at room temperature for 1 h. Sodium triacetoxyborohydride (0.33 g, 1.5 mol)) was added and reacted for another 24 h, and extracted with ethyl acetate. A saturated sodium bicarbonate solution was added to adjust pH to weakly alkaline, and the organic phases were combined, and purified by silica gel column chromatography to obtain a white solid (0.15 g, 58.6%).

$^1$H NMR (400 MHz, $CDCl_3$) (δ 7.92 (d, J=1.6 Hz, 2H), 7.83 (s, 1H), 6.16 (d, J=2.2 Hz, 1H), 6.14 (d, J=2.2 Hz, 1H), 5.14 (s, 2H), 3.68 (s, 2H), 3.61 (t, J=5.3 Hz, 2H), 2.68-2.52 (m, 10H).

MS (ESI): m/z 523.20 $[M+H]^+$.

Example 6. Preparation of Compound (4)

(4) MZ28

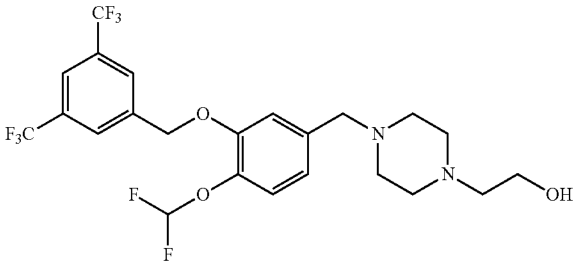

Step 1) 3,5-bistrifluoromethylbenzyl bromide (0.22 mL, 1.2 mmol), 4-difluoromethoxy-3-hydroxybenzaldehyde (0.13 g, 1 mol), potassium carbonate (0.41 g, 3 mmol), and DMF (10 mL) were successively added to a 100 ml single-neck round-bottom flask, reacted at room temperature for 6 h, and extracted with ethyl acetate. Organic phases were combined, concentrated under a reduced pressure, and then purified by silica gel column to obtain a white solid (0.37 g, 89.3%).

$^1$H NMR (400 MHz, $CDCl_3$) (δ 9.95 (s, 1H), 7.94 (s, 2H), 7.88 (s, 1H), 7.58 (d, J=1.8 Hz, 1H), 7.55 (dd, J=8.1, 1.8 Hz, 1H), 7.39 (d, J=8.1 Hz, 1H), 6.65 (t, J=73.2 Hz, 1H), 5.29 (s, 2H).

MS (ESI): m/z 415.05 $[M+H]^+$;

Step 2) 4-difluoromethoxy-3-(3,5-bistrifluoromethylbenzyl)benzaldehyde (0.21 g, 0.5 mmol), 1-(2-hydroxyethyl) piperazine (0.18 mL, 1.5 mmol), acetic acid (0.17 mL, 1.5 mmol), and THF (10 mL) were successively added to a 100 mL three-neck round-bottom flask under a nitrogen protection, and reacted at room temperature for 1 h. Sodium triacetoxyborohydride (0.33 g, 1.5 mol) was added and reacted for another 24 h, and extracted with ethyl acetate. A saturated sodium bicarbonate solution was added to adjust pH to weakly alkaline. Organic phases were combined, and purified by silica gel column chromatography to obtain an oily liquid (0.18 g, 68.0%).

$^1$H NMR (400 MHz, $CDCl_3$) (δ 7.95-7.92 (m, 2H), 7.84 (s, 1H), 7.16 (d, J=8.1 Hz, 1H), 7.05 (d, J=1.9 Hz, 1H), 6.93 (dd, J=8.2, 1.9 Hz, 1H), 6.51 (t, J=74.3 Hz, 1H), 5.20 (s, 2H), 3.67 (s, 2H), 3.60 (t, J=5.3 Hz, 2H), 2.69-2.50 (m, 10H).

MS (ESI): m/z 529.17 $[M+H]^+$.

Example 7. Preparation of Compound (5)

(5) MZ29

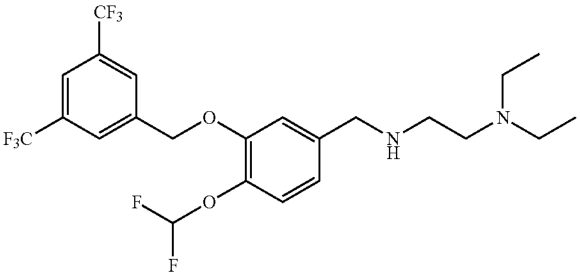

Step 1) 3,5-bistrifluoromethylbenzyl bromide (0.22 mL, 1.2 mmol), 4-difluoromethoxy-3-hydroxybenzaldehyde (0.13 g, 1 mol), potassium carbonate (0.41 g, 3 mmol), DMF (10 mL) weres successively added to a 100 ml single-neck round-bottom flask, reacted at room temperature for 6 h, and extracted with ethyl acetate. Organic phases were combined, concentrated under a reduced pressure, and then purified by silica gel column to obtain a white solid (0.37 g, 89.3%).

$^1$H NMR (400 MHz, $CDCl_3$) (δ 9.95 (s, 1H), 7.94 (s, 2H), 7.88 (s, 1H), 7.58 (d, J=1.8 Hz, 1H), 7.55 (dd, J=8.1, 1.8 Hz, 1H), 7.39 (d, J=8.1 Hz, 1H), 6.65 (t, J=73.2 Hz, 1H), 5.29 (s, 2H).

MS (ESI): m/z 415.05 $[M+H]^+$;

Step 2) 4-difluoromethoxy-3-(3,5-bistrifluoromethylbenzyl)benzaldehyde (0.21 g, 0.5 mmol), N,N-diethylethylenediamine (0.21 mL, 1.5 mmol)), acetic acid (0.17 mL, 1.5 mmol), and THF (10 mL) were successively added to a 100 mL three-neck round-bottom flask under a nitrogen protection, and reacted at room temperature for 1 h. Sodium triacetoxyborohydride (0.33 g, 1.5 mol) was added, reacted for another 24 h, and extracted with ethyl acetate. A saturated sodium bicarbonate solution was added to adjust pH to weakly alkaline. Organic phases were combined, and purified by silica gel column chromatography to obtain a white solid (0.18 g, 70.03%).

$^1$H NMR (400 MHz, $CDCl_3$) (δ 7.97-7.93 (m, 2H), 7.85 (s, 1H), 7.18 (d, J=8.1 Hz, 1H), 7.06 (d, J=1.9 Hz, 1H), 6.93 (dd, J=8.2, 1.9 Hz, 1H), 6.52 (t, J=74.3 Hz, 1H), 5.22 (s, 2H), 3.81 (s, 2H), 2.64 (t, J=6.4 Hz, 2H), 2.58 (t, J=5.9 Hz, 2H), 2.47 (q, J=7.1 Hz, 4H), 0.99 (t, J=7.1 Hz, 6H).

MS (ESI): m/z 515.19 $[M+H]^+$.

Example 8. Preparation of Compound (6)

(6) MZ24

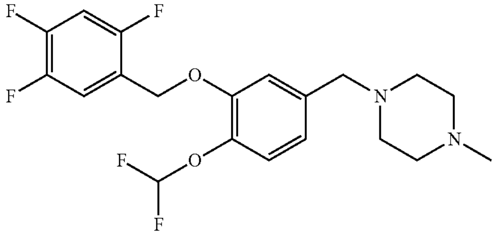

Step 1) 2,4,5-trifluorobenzyl bromide (0.16 mL, 1.2 mmol), 4-difluoromethoxy-3-hydroxybenzaldehyde (0.13 g, 1 mol), potassium carbonate (0.41 g, 3 mmol), and DMF (10 mL) were sequentially added to a 100 ml single-neck round-bottom flask, reacted at room temperature for 6 h, and extracted with ethyl acetate. Organic phases were combined, concentrated under a reduced pressure, and then purified by silica gel column to obtain a white solid (0.3 g, 90.0%).

$^1$H NMR (400 MHz, $CDCl_3$) (δ 9.95 (s, 1H), 7.57 (d, J=1.8 Hz, 1H), 7.53 (dd, J=8.1, 1.8 Hz, 1H), 7.38 (d, J=10.2 Hz, 1H), 7.36-7.32 (m, 1H), 7.00 (td, J=9.6, 6.4 Hz, 1H), 6.64 (t, J=73.6 Hz, 1H), 5.18 (q, J=1.0 Hz, 2H).

MS (ESI): m/z 333.05 $[M+H]^+$;

Step 2) 4-difluoromethoxy-3-(2,4,5-trifluorobenzyl)benzaldehyde (0.167 g, 0.5 mmol), N-methylpiperazine (0.17 mL, 1.5 mL), acetic acid (0.17 mL, 1.5 mmol), and THF (10 mL) were successively added to a 100 mL three-neck round-bottom flask under a nitrogen protection, and reacted at room temperature for 1 h. Sodium triacetoxyborohydride (0.33 g, 1.5 mol) was added and reacted for another 24 h, and extracted with ethyl acetate. A saturated sodium bicarbonate solution was added to adjust pH to weakly alkaline. Organic phases were combined, and purified by silica gel column chromatography to obtain an oily liquid (0.15 g, 71.9%).

$^1$H NMR (400 MHz, $CDCl_3$) (δ 7.36 (ddd, J=10.3, 8.7, 6.6 Hz, 1H), 7.11 (d, J=8.1 Hz, 1H), 7.04 (d, J=1.9 Hz, 1H), 7.01-6.93 (m, 1H), 6.91 (dd, J=8.1, 1.9 Hz, 1H), 6.51 (t, J=74.8 Hz, 1H), 5.11 (q, J=1.0 Hz, 2H), 3.46 (s, 2H), 2.44 (s, 8H), 2.29 (s, 3H).

MS (ESI): m/z 417.15 $[M+H]^+$.

Example 9. Preparation of Compound (7)

(7) MZ26

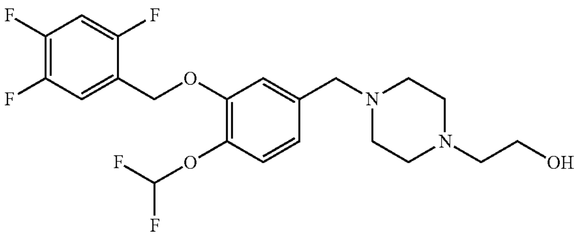

Step 1) 2,4,5-trifluorobenzyl bromide (0.16 mL, 1.2 mmol), 4-difluoromethoxy-3-hydroxybenzaldehyde (0.13 g, 1 mol), potassium carbonate (0.41 g, 3 mmol), and DMF (10 mL) were sequentially added to a 100 ml single-neck round-bottom flask, reacted at room temperature for 6 h, and extracted with ethyl acetate. Organic phases were combined, concentrated under a reduced pressure, and then purified by silica gel column to obtain a white solid (0.3 g, 90.0%).

$^1$H NMR (400 MHz, $CDCl_3$) δ 9.95 (s, 1H), 7.57 (d, J=1.8 Hz, 1H), 7.53 (dd, J=8.1, 1.8 Hz, 1H), 7.38 (d, J=10.2 Hz, 1H), 7.36-7.32 (m, 1H), 7.00 (td, J=9.6, 6.4 Hz, 1H), 6.64 (t, J=73.6 Hz, 1H), 5.18 (q, J=1.0 Hz, 2H).

MS (ESI): m/z: 333.05 $[M+H]^+$;

Step 2) 4-difluoromethoxy-3-(2,4,5-trifluorobenzyl)benzaldehyde (0.167 g, 0.5 mmol), 1-(2-hydroxyethyl)piperazine (0.18 mL, 1.5 mmol), acetic acid (0.17 mL, 1.5 mmol), and THF (10 mL) were successively added to a 100 mL three-neck round-bottom flask under a nitrogen protection, and reacted at room temperature for 1 h. Sodium triacetoxyborohydride (0.33 g, 1.5 mol) was added, reacted for another 24 h, and extracted with ethyl acetate. A saturated sodium bicarbonate solution was added to adjust pH to weakly alkaline. Organic phases were combined, and purified by silica gel column chromatography to obtain an oily liquid (0.13 g, 58.2%).

$^1$H NMR (400 MHz, $CDCl_3$) δ 7.37 (ddd, J=10.4, 8.7, 6.6 Hz, 1H), 7.12 (d, J=8.1 Hz, 1H), 7.03 (d, J=1.9 Hz, 1H), 6.97 (td, J=9.6, 6.4 Hz, 1H), 6.91 (dd, J=8.2, 1.9 Hz, 1H), 6.52 (t, J=74.7 Hz, 1H), 5.11 (s, 2H), 3.71-3.65 (m, 2H), 3.48 (s, 2H), 2.75-2.60 (m, 6H), 2.52 (s, 4H).

MS (ESI): m/z 447.16 (100.0%) $[M+H]^+$.

Example 10. Preparation of Compound (8)

(8) MZ34

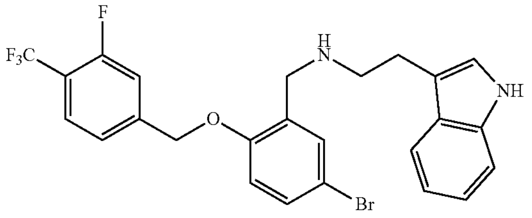

Step 1) 4-fluoro-3-trifluoromethylbenzyl bromide (0.19 mL, 1.2 mmol), 2-hydroxy-5-bromobenzaldehyde (0.20 g, 1 mmol), potassium carbonate (0.41 g, 3 mmol), and DMF (10 mL) were sequentially added to a 100 mL single-neck round-bottom flask, reacted at room temperature for 6 h, and extracted with ethyl acetate. Organic phases were combined, concentrated under a reduced pressure, and purified by silica gel column to obtain a white solid (0.32 g, 85.3%).

$^1$H NMR (400 MHz, $CDCl_3$) (δ 10.42 (s, 1H), 7.96 (d, J=2.6 Hz, 1H), 7.65 (dtd, J=13.1, 5.5, 4.3, 2.3 Hz, 3H), 7.28 (d, J=9.5 Hz, 1H), 6.93 (d, J=8.8 Hz, 1H), 5.17 (s, 2H).

MS (ESI): m/z 376.97 $[M+H]^+$;

Step 2) 2-(4-fluoro-3-trifluoromethylbenzyl)-5-bromobenzaldehyde (0.19 g, 0.5 mmol), tryptamine (0.24 g, 1.5 mmol), acetic acid (0.17 mL, 1.5 mmol), and THF (10 mL) were successively added to a 100 mL three-neck round-bottom flask under a nitrogen protection, and reacted at room temperature for 1 h. Sodium triacetoxyborohydride (0.33 g, 1.5 mol) was added, reacted for 24 h, and extracted with ethyl acetate. A saturated sodium bicarbonate solution was added to adjust pH to weakly alkaline, and the organic phases were combined and purified by silica gel column chromatography to obtain an oily liquid (0.15 g, 57.6%).

$^1$H NMR (500 MHz, $CDCl_3$) (δ 9.94 (d, J=8.4 Hz, 1H), 7.62-7.59 (m, 1H), 7.59-7.56 (m, 1H), 7.36-7.30 (m, 3H), 7.14 (td, J=7.5, 1.5 Hz, 1H), 7.12-7.10 (m, 2H), 7.05 (td, J=7.5, 1.6 Hz, 1H), 6.97 (dq, J=7.5, 1.2 Hz, 1H), 6.87 (d, J=7.3 Hz, 1H), 5.16 (t, J=1.0 Hz, 2H), 4.13-4.09 (m, 2H), 3.21-3.16 (m, 2H), 2.98-2.79 (m, 2H).

MS (ESI): m/z 521.08 $[M+H]^+$.

Example 11. Preparation of Compound (9)

(9) MZ31

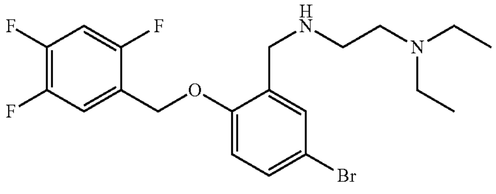

Step 1) 2,4,5-trifluorobenzyl bromide (0.16 mL, 1.2 mmol), 2-hydroxy-5-bromobenzaldehyde (0.20 g, 1 mmol), potassium carbonate (0.41 g, 3 mmol), and DMF (10 mL) were successively added to a 100 ml single-neck round-bottom flask, reacted at room temperature for 6 h, and extracted with ethyl acetate. Organic phases were combined, concentrated under a reduced pressure, and then purified by silica gel column to obtain a white solid (0.30 g, 87.2%).

$^1$H NMR (400 MHz, $CDCl_3$) (δ 10.38 (s, 1H) 8.02 (d, J=1.5 Hz, 1H), 7.46 (dd, J=7.5, 1.5 Hz, 1H), 7.12 (dtt, J=8.0, 4.9, 1.1 Hz, 1H), 7.02 (d, J=7.5 Hz, 1H), 7.01 (td, J=8.1, 5.0 Hz, 1H), 5.18 (s, 2H).

MS (ESI): m/z 344.97 $[M+H]^+$;

Step 2) 2-(2,4,5-trifluorobenzyl)-5-bromobenzaldehyde (0.17 g, 0.5 mmol), N,N-diethylethylenediamine (0.21 mL, 1.5 mmol), acetic acid (0.17 mL, 1.5 mmol), and THF (10 mL) were successively added to a 100 mL three-neck round-bottom flask under a nitrogen protection, and reacted at room temperature for 1 h. Sodium triacetoxyborohydride (0.33 g, 1.5 mol) was added, reacted for another 24 h, and extracted with ethyl acetate. A saturated sodium bicarbonate solution was added to adjust pH to weakly alkaline. Organic phases were combined, and purified by silica gel column chromatography to obtain an oily liquid (0.12 g, 54.05%).

$^1$H NMR (400 MHz, $CDCl_3$) (δ 7.44 (d, J=2.5 Hz, 1H), 7.33 (td, J=9.3, 8.7, 2.8 Hz, 2H), 6.97 (td, J=9.6, 6.4 Hz, 1H), 6.77 (d, J=8.7 Hz, 1H), 5.05 (s, 2H), 3.80 (s, 2H), 2.66 (t, J=6.4 Hz, 2H), 2.56 (t, J=5.9 Hz, 2H), 2.48 (q, J=7.1 Hz, 4H), 0.97 (t, J=7.1 Hz, 6H).

MS (ESI): m/z 445.10 $[M+H]^+$.

Example 12. Preparation of Compound (10)

(10) MZ75

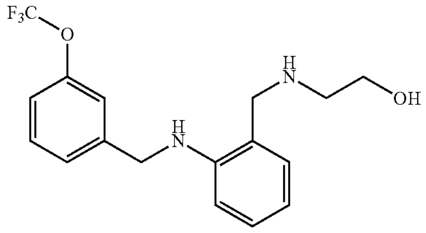

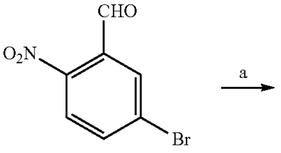

1

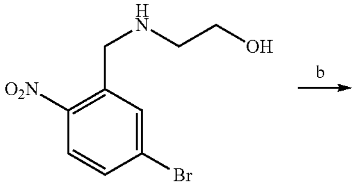

2

-continued

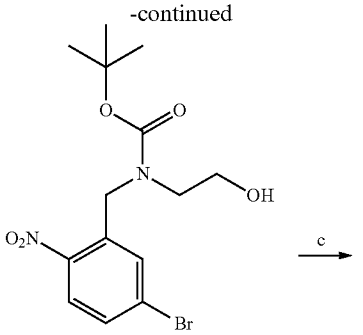

3

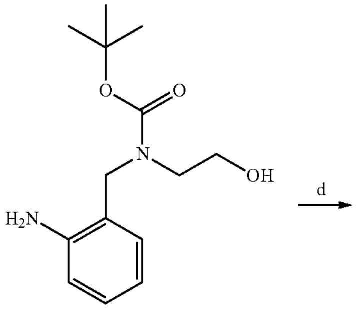

4

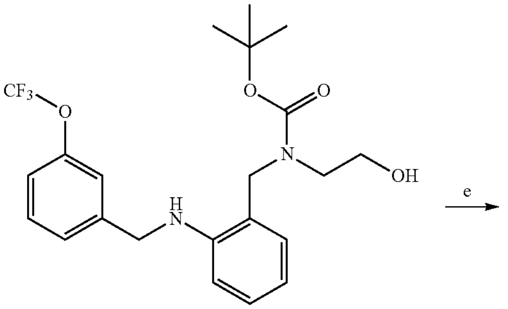

5

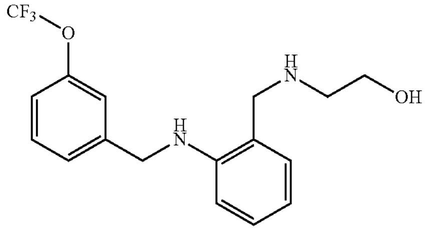

MZ75 a) Under $N_2$ protection, compound 1 (0.69 g, 3 mmol) and DCM (20 mL) were added to a 100 mL two-neck round-bottom flask, and then ethanolamine (0.54 mL, 9 mmol) and acetic acid (0.17 mL, 1.5 mmol) were added, and reacted at room temperature for 2 h. Sodium triacetoxyborohydride (1.27 g, 6 mmol) was added. The reaction was detected by TLC, quenched with a saturated sodium bicarbonate solution, and extracted with ethyl acetate. Organic phases were combined, and purified by silica gel column normal phase chromatography to obtain compound 2 (0.70 g, 85.3%).

$^1$H NMR (400 MHz, DMSO-$d_6$) δ 7.98 (d, J=2.2 Hz, 1H), 7.91 (d, J=8.6 Hz, 1H), 7.72 (dd, J=8.6, 2.3 Hz, 1H), 4.51 (t, J=5.3 Hz, 1H), 3.97 (s, 2H), 3.44 (q, J=5.4 Hz, 2H), 2.55 (t, J=5.8 Hz, 2H).

b) Compound 2 (0.41 g, 1.5 mmol) was placed in a 100 mL round-bottom flask, DCM (10 mL) and di-tert-butyl dicarbonate (0.69 mL, 0.3 mmol) were added successively, and reacted at room temperature until the completion of the reaction was detected by TLC. Water was added to quench the reaction, and the reaction solution was extracted with ethyl acetate. Organic phases were combined, and purified by normal phase chromatography on silica gel column to obtain compound 3 (0.50 g, 89.8%).

$^1$H NMR (400 MHz, DMSO-$d_6$) δ 8.06-7.95 (m, 1H), 7.77 (dd, J=8.7, 2.2 Hz, 1H), 7.52 (d, J=46.6 Hz, 1H), 4.74 (t, J=5.2 Hz, 2H), 4.70 (s, 1H), 3.51 (q, J=5.6 Hz, 2H), 3.28 (t, 2H), 1.50-1.15 (m, 9H).

c) Under H2 condition, compound 3 (0.37 g, 1 mmol), 10% Pd/C (100 mg), and MeOH (10 mL) were added to a 100 round-bottom flask, and the reaction was carried out at room temperature until the completion of the reaction was detected by TLC. The reaction system was filtered, and extracted with ethyl acetate. Organic phases were combined and purified by normal phase chromatography on silica gel column to obtain compound 4 (0.18 g, 67.5%).

$^1$H NMR (400 MHz, DMSO-$d_6$) δ 6.97 (t, J=7.5 Hz, 1H), 6.92 (s, 2H), 6.61 (d, J=7.9 Hz, 1H), 6.52 (d, J=7.5 Hz, 1H), 4.68 (s, 1H), 4.29 (s, 2H), 3.43 (q, J=5.7 Hz, 2H), 3.16-3.04 (m, 2H), 1.39 (d, J=14.6 Hz, 9H).

d) Under $N_2$ protection, 3-trifluoromethoxybenzaldehyde (0.11 g, 0.6 mmol) and DCM (10 mL) were added to a 100 mL double-neck round-bottom flask, then compound 4 (0.32 g, 1.2 mmol), and acetic acid (0.03 ml, 0.3 mmol) were added, and reacted for 2 hours at room temperature. Sodium triacetoxyborohydride (0.25 g, 1.2 mmol) was added, and the reaction was detected by TLC, quenched with a saturated sodium bicarbonate solution, and extracted with ethyl acetate. Organic phases were combined, and purified by normal phase chromatography on silica gel column to obtain compound 5 (0.20 g, 75.1%). $^1$H NMR (400 MHz, DMSO-$d_6$) δ 7.44 (t, J=7.9 Hz, 1H), 7.36 (d, J=7.7 Hz, 1H), 7.24 (s, 1H), 7.22-7.18 (m, 1H), 7.07-6.97 (m, 2H), 6.57 (t, J=7.3 Hz, 1H), 6.44 (dd, J=8.3, 1.1 Hz, 1H), 6.06 (s, 1H), 4.72 (t, J=5.5 Hz, 1H), 4.41 (d, J=3.6 Hz, 4H), 3.46 (q, J=6.2 Hz, 2H), 3.14 (s, 2H), 1.36 (s, 9H).

e) Compound 5 (0.15 g, 0.35 mmol) was placed in a 100 mL round-bottom flask, then DCM (10 mL) and 2 mL of trifluoroacetic acid were successively added and reacted at room temperature for 1 h. The reaction was quenched with a saturated sodium bicarbonate solution, and extracted with ethyl acetate. Organic phases were combined, and purified by normal phase chromatography on silica gel column to obtain compound MZ75 (0.1 g, 84.6%).

$^1$H NMR (400 MHz, DMSO-$d_6$) δ 7.45 (t, J=7.7 Hz, 1H), 7.42-7.39 (m, 1H), 7.32 (s, 1H), 7.19 (dd, J=7.9, 5.1 Hz, 1H), 7.03 (dd, J=7.4, 1.6 Hz, 1H), 6.99 (td, J=7.7, 1.7 Hz, 1H), 6.79 (s, 1H), 6.52 (t, J=7.3 Hz, 1H), 6.43 (d, J=8.0 Hz, 1H), 4.56 (s, 1H), 4.40 (s, 2H), 3.77 (s, 2H), 3.49 (d, J=7.1 Hz, 2H), 2.59 (t, J=5.7 Hz, 2H).

Example 13. Preparation of Compounds (11) and (12)

(11) MZ76

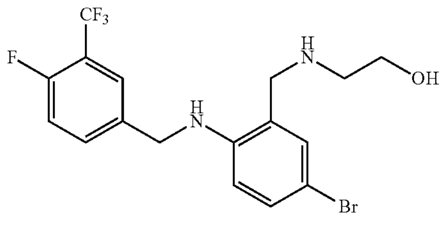

-continued

(12) MZ77

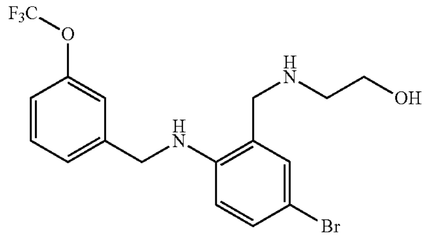

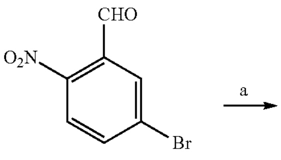

1

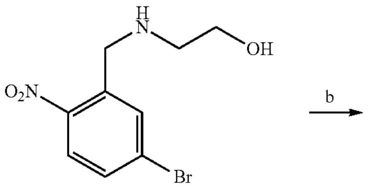

2

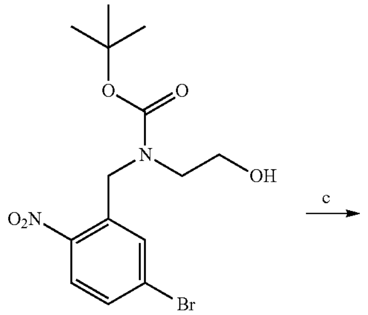

3

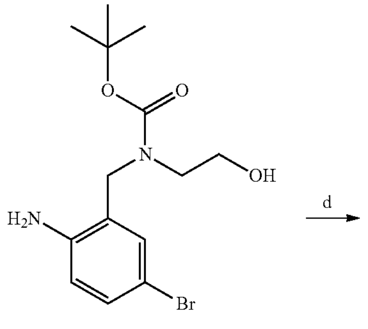

4

-continued

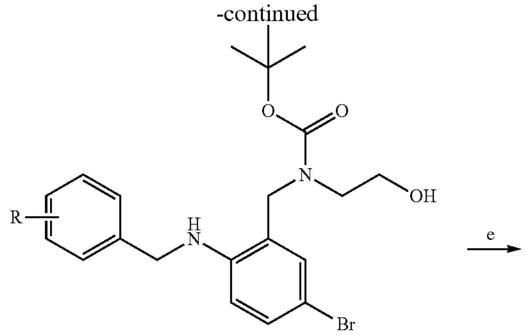

5-1 R = 4-F, 3-$CF_3$
5-2 R = 3-$OCF_3$

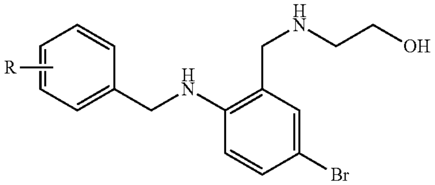

MZ76 R = 4-F, 3-$CF_3$
MZ77 R = 3-$OCF_3$

Step a) Under $N_2$ protection, compound 1 (0.69 g, 3 mmol) and DCM (20 mL) were added to a 100 mL double-neck round-bottom flask, and then ethanolamine (0.54 mL, 9 mmol) and acetic acid (0.17 mL, 1.5 mmol) were added and reacted at room temperature for 2 h. Sodium triacetoxy-borohydride (1.98 g, 6 mmol) was added. The reaction was completed as being detected by TLC, quenched with a saturated sodium bicarbonate solution, and extracted with ethyl acetate. Organic phases were combined, and purified by silica gel column normal phase chromatography to obtain compound 2 (0.69 g, 83.5%).

$^1$H NMR (400 MHz, DMSO-$d_6$) δ 7.98 (d, J=2.2 Hz, 1H), 7.91 (d, J=8.6 Hz, 1H), 7.72 (dd, J=8.6, 2.3 Hz, 1H), 4.51 (t, J=5.3 Hz, 1H), 3.97 (s, 2H), 3.44 (q, J=5.4 Hz, 2H), 2.55 (t, J=5.8 Hz, 2H).

Step b) Compound 2 (0.41 g, 1.5 mmol) was placed in a 100 mL round-bottom flask, and then DCM (10 mL) and di-tert-butyl dicarbonate (0.69 mL, 0.3 mmol) were added successively, and reacted at room temperature until the completion of the reaction was detected by TLC. The reaction was quenched by adding water, and extracted with ethyl acetate. Organic phases were combined and purified by normal phase chromatography on silica gel column to obtain compound 3 (0.50 g, 89.8%).

$^1$H NMR (400 MHz, DMSO-$d_6$) δ 8.06-7.95 (m, 1H), 7.77 (dd, J=8.7, 2.2 Hz, 1H), 7.52 (d, J=46.6 Hz, 1H), 4.74 (t, J=5.2 Hz, 2H), 4.70 (s, 1H), 3.51 (q, J=5.6 Hz, 2H), 3.28 (t, 2H), 1.50-1.15 (m, 9H).

Step c) Compound 3 (0.56 g, 1.5 mmol), iron powder for reduction (0.42 g, 7.5 mmol), $NH_4C_1$ (0.80 g, 15 mmol) and MeOH (15 mL) were added to a 100 round-bottom flask, refluxed at 80° C. The reaction was completed as being detected by TLC, quenched by adding water, and extracted with ethyl acetate. Organic phases were combine, and purified by silica gel column normal phase chromatography to obtain compound 4 (0.37 g, 71.6%).

$^1$H NMR (400 MHz, DMSO-$d_6$) δ 7.11 (dd, J=8.6, 2.3 Hz, 1H), 7.06 (s, 1H), 6.58 (d, J=8.5 Hz, 1H), 5.45-5.05 (m, 2H), 4.71 (s, 1H), 4.26 (s, 2H), 3.45 (t, J=6.4 Hz, 2H), 3.11 (s, 2H).

Step d) Under $N_2$ protection, 3-trifluoromethyl-4-fluorobenzaldehyde (0.096 g, 0.5 mmol) and DCM (10 mL) were added to a 100 mL double-neck round bottom flask, and then compound 4 (0.17 g, 0.5 mmol) and acetic acid (0.28 mL, 0.25 mmol) were added and reacted at room temperature for 2 h. Sodium triacetoxyborohydride (0.32 g, 1.5 mmol) was added, and the reaction was completed as being detected by TLC, quenched with a saturated sodium bicarbonate solution, and extracted with ethyl acetate. Organic phases were combined and purified by silica gel column normal phase chromatography to obtain compound 5-1 (0.20 g, 76.4%).

$^1$H NMR (400 MHz, DMSO-$d_6$) δ 7.76-7.60 (m, 2H), 7.47 (t, J=9.8 Hz, 1H), 7.17 (s, 2H), 6.41 (d, J=8.7 Hz, 1H), 6.17 (s, 1H), 4.74 (t, J=5.4 Hz, 1H), 4.45-4.35 (m, 4H), 3.47 (q, J=6.1 Hz, 2H), 3.14 (s, 2H), 1.33 (s, 9H).

Under $N_2$ protection, 3-trifluoromethoxybenzaldehyde (0.095 g, 0.5 mmol) and DCM (10 mL) were added to a 100 mL double-neck round-bottom flask. And then compound 4 (0.17 g, 0.5 mmol) and acetic acid (0.28 mL, 0.25 mmol) were added and reacted at room temperature for 2 hrs.

Sodium triacetoxyborohydride (0.32 g, 1.5 mmol) was added, and the reaction was completed as being detected by TLC, quenched with a saturated sodium bicarbonate solution, and extracted with ethyl acetate. Organic phases were combined, and purified by silica gel column normal phase chromatography to obtain compound 5-2 (0.21 g, 79.2%).

$^1$H NMR (400 MHz, DMSO-$d_6$) δ 7.45 (t, J=7.9 Hz, 1H), 7.34 (d, J=7.7 Hz, 1H), 7.21 (d, J=9.1 Hz, 2H), 7.16 (d, J=8.2 Hz, 2H), 6.39 (d, J=8.7 Hz, 1H), 6.20 (s, 1H), 4.39 (d, J=3.7 Hz, 4H), 3.48 (t, J=6.3 Hz, 2H), 3.15 (s, 2H), 1.34 (d, J=8.9 Hz, 9H).

Step e) Compound 5-1 (0.182 g, 0.35 mmol) was placed in a 100 mL round-bottom flask, and DCM (10 mL) and 2 mL of trifluoroacetic acid were added successively. The reaction was carried out at room temperature for 1 h, quenched with a saturated sodium bicarbonate solution, and extracted with ethyl acetate. Organic phases were combined and purified by silica gel column normal phase chromatography to obtain compound MZ76 (0.13 g, 87.1%).

$^1$H NMR (400 MHz, DMSO-$d_6$) δ 7.45 (t, J=7.9 Hz, 1H), 7.34 (d, J=7.7 Hz, 1H), 7.21 (d, J=9.1 Hz, 2H), 7.16 (d, J=8.2 Hz, 2H), 6.39 (d, J=8.7 Hz, 1H), 6.20 (s, 1H), 4.39 (d, J=3.7 Hz, 4H), 3.48 (t, J=6.3 Hz, 2H), 3.15 (s, 2H), 1.34 (d, J=8.9 Hz, 9H).

Compound 5-2 (0.181 g, 0.35 mmol) was placed in a 100 mL round-bottom flask, and DCM (10 mL) and 2 mL of trifluoroacetic acid were added successively. The reaction was carried out at room temperature for 1 h, quenched with a saturated sodium bicarbonate solution, and extracted with ethyl acetate. Organic phases were combined and purified by silica gel column normal phase chromatography to obtain compound MZ77 (0.125 g, 85.7%).

$^1$H NMR (400 MHz, DMSO-$d_6$) δ 7.45 (t, J=7.8 Hz, 1H), 7.38 (d, J=7.7 Hz, 1H), 7.31 (s, 1H), 7.21 (q, J=3.4 Hz, 2H), 7.12 (dd, J=8.6, 2.5 Hz, 1H), 6.87 (d, J=6.3 Hz, 1H), 6.36 (d, J=8.6 Hz, 1H), 4.57 (s, 1H), 4.40 (d, J=5.4 Hz, 2H), 3.74 (s, 2H), 3.48 (q, J=5.5 Hz, 2H), 2.58 (t, J=5.8 Hz, 2H).

Example 14. Preparation of Compound (13)

(13) MZ1

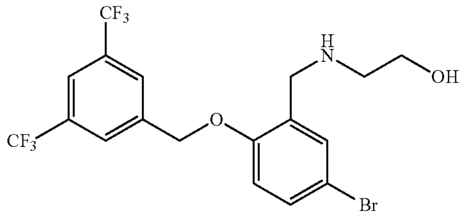

Step 1) 3,5-bistrifluoromethylbenzyl bromide (0.22 mL, 1.2 mmol), 2-hydroxy-5-bromobenzaldehyde (0.20 g, 1 mmol), potassium carbonate (0.41 g, 3 mmol) and DMF (10 mL) were successively added to a 100 ml single-neck round-bottom flask, reacted at room temperature for 6 hours, and extracted with ethyl acetate. Organic phases were combined, concentrated under a reduced pressure and purified by silica gel column to obtain a white solid (0.40 g, 94.1%).

$^1$H NMR (400 MHz, $CDCl_3$) δ 10.42 (s, 1H), δ 7.90 (s, 2H), 7.87 (s, 1H), 7.47 (d, J=2.5 Hz, 1H), 7.38 (dd, J=8.7, 2.5 Hz, 1H), 6.77 (d, J=8.7 Hz, 1H), 5.19 (s, 2H).

MS (ESI): m/z 426.97 $[M+H]^+$;

Step 2) 2-(3,5-bistrifluoromethylbenzyloxy)-5-bromobenzaldehyde (0.21 g, 0.5 mmol), ethanolamine (0.09 mL, 1.5 mmol), acetic acid (0.17 mL, 1.5 mmol) and THF (10 mL) were sequentially added to a 100 mL three-neck round-bottom flask under a nitrogen protection, and reacted at room temperature for 1 h. Sodium triacetoxyborohydride (0.33 g, 1.5 mmol) was added and reacted for another 24 hrs. The reaction solution was extracted with ethyl acetate, and a saturated sodium bicarbonate solution was added to adjust pH to weakly basic. Organic phases were combined and purified by silica gel column chromatography to obtain a white solid (0.14 g, 59.45%).

$^1$H NMR (400 MHz, $CDCl_3$) δ 7.90 (s, 2H), 7.87 (s, 1H), 7.47 (d, J=2.5 Hz, 1H), 7.38 (dd, J=8.7, 2.5 Hz, 1H), 6.77 (d, J=8.7 Hz, 1H), 5.19 (s, 2H), 3.90 (s, 2H), 3.74-3.66 (m, 2H), 2.82 (dd, J=6.0, 4.3 Hz, 2H), 1.91 (s, 1H).

MS (ESI): m/z 472.03 $[M+H]^+$.

Example 15. Preparation of Compound (14)

(14) MZ30

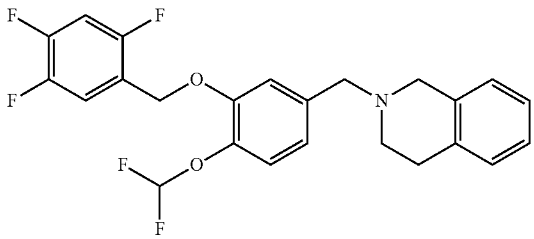

Step 1) 2,4,5-trifluorobenzyl bromide (0.16 mL, 1.2 mmol), 4-difluoromethoxy-3-hydroxybenzaldehyde (0.13 g, 1 mol), potassium carbonate (0.41 g, 3 mmol) and DMF (10 mL) were sequentially added to a 100 mL single-neck round-bottom flask, reacted at room temperature for 6 hrs, and extracted with ethyl acetate. Organic phases were combined, concentrated under a reduced pressure, and purified by silica gel column to obtain a white solid (0.3 g, 90.0%).

$^1$H NMR (400 MHz, $CDCl_3$) δ 10.42 (s, 1H), δ 7.36 (ddd, J=10.3, 8.7, 6.6 Hz, 1H), 7.11 (d, J=8.1 Hz, 1H), 7.04 (d, J=1.9 Hz, 1H), 7.01-6.93 (m, 1H), 6.91 (dd, J=8.1, 1.9 Hz, 1H), 6.51 (t, J=74.8 Hz, 1H), 5.11 (q, J=1.0 Hz, 2H).

MS (ESI): m/z 333.05 $[M+H]^+$;

Step 2) 4-difluoromethoxy-3-(2,4,5-trifluorobenzyloxy) benzaldehyde (0.167 g, 0.5 mmol), tetrahydroisoquinoline (0.19 mL, 1.5 mmol), acetic acid (0.17 mL, 1.5 mmol) and THF (10 mL) were sequentially added to a 100 mL three-neck round-bottom flask under a nitrogen protection, and reacted at room temperature for 1 h. Sodium triacetoxyborohydride (0.33 g, 1.5 mmol) was added and reacted for another 24 h. The reaction solution was extracted with ethyl acetate, and a saturated sodium bicarbonate solution was added to adjust pH to weakly alkaline. Organic phases were combined and purified by silica gel column chromatography to obtain an oily liquid (0.14 g, 60.4%).

$^1$H NMR (400 MHz, $CDCl_3$) δ 7.37 (ddd, J=10.4, 8.8, 6.6 Hz, 1H), 7.13 (dtd, J=10.5, 6.0, 5.6, 3.5 Hz, 5H), 6.98 (dd, J=8.2, 1.8 Hz, 2H), 6.89 (td, J=9.6, 6.4 Hz, 1H), 6.54 (t, J=74.8 Hz, 1H), 5.10 (s, 2H), 3.64 (s, 2H), 3.61 (s, 2H), 2.90 (t, J=5.9 Hz, 2H), 2.73 (t, J=5.9 Hz, 2H).

Example 16. Preparation of Compound (15)

(15) MZ32

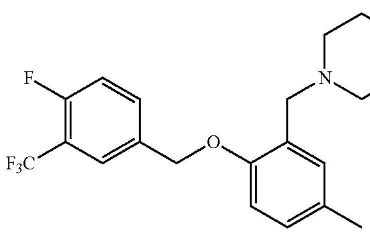

Step 1) 4-fluoro-3-trifluoromethylbenzyl bromide (0.19 mL, 1.2 mmol), 2-hydroxy-5-bromobenzaldehyde (0.20 g, 1 mmol), potassium carbonate (0.41 g, 3 mmol) and DMF (10 mL) were successively added to a 100 ml single-neck round-bottom flask, reacted at room temperature for 6 hours, and extracted with ethyl acetate. Organic phases were combined, concentrated under a reduced pressure, and then purified by silica gel column to obtain a white solid (0.32 g, 85.3%).

$^1$H NMR (400 MHz, $CDCl_3$) δ 10.42 (s, 1H), 7.96 (d, J=2.6 Hz, 1H), 7.65 (dtd, J=13.1, 5.5, 4.3, 2.3 Hz, 3H), 7.28 (d, J=9.5 Hz, 1H), 6.93 (d, J=8.8 Hz, 1H), 5.17 (s, 2H).

MS (ESI): m/z 376.97 $[M+H]^+$;

Step 2) 2-(4-fluoro-3-trifluoromethylbenzyloxy)-5-bromobenzaldehyde (0.19 g, 0.5 mmol), 1-(2-hydroxyethyl) piperazine (0.18 mL, 1.5 mmol), acetic acid (0.17 mL, 1.5 mmol) and THF (10 mL) were successively added to a 100 mL three-neck round-bottom flask under a nitrogen protection, and reacted at room temperature for 1 h. Sodium triacetoxyborohydride (0.33 g, 1.5 mmol) was added and reacted for another 24 h. The reaction solution was extracted with ethyl acetate, and a saturated sodium bicarbonate solution was added to adjust pH to weakly alkaline. Organic phases were combined, and purified by silica gel column chromatography to obtain a white solid (0.13 g, 53.06%).

$^1$H NMR (400 MHz, $CDCl_3$) δ 7.67 (dd, J=6.8, 2.2 Hz, 1H), 7.62 (ddd, J=7.4, 4.7, 2.2 Hz, 1H), 7.50 (d, J=2.6 Hz, 1H), 7.32 (dd, J=8.7, 2.6 Hz, 1H), 7.22 (d, J=9.2 Hz, 1H), 6.76 (d, J=8.7 Hz, 1H), 5.05 (s, 2H), 3.61 (t, J=5.4 Hz, 2H), 3.54 (s, 2H), 2.55 (d, J=6.9 Hz, 10H).

MS (ESI): m/z 491.09 $[M+H]^+$.

Example 17. Preparation of Compound (16)

(16) MZ67

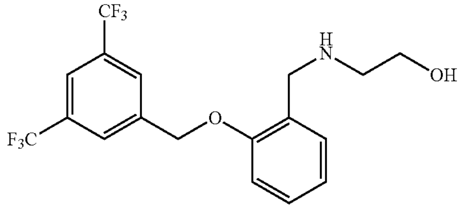

Step 1) 3,5-bistrifluoromethylbenzyl bromide (0.22 mL, 1.2 mmol), 2-hydroxybenzaldehyde (0.12 g, 1 mmol), potassium carbonate (0.41 g, 3 mmol) and DMF (10 mL) to a 100 ml single-neck round-bottom flask and reacted at room temperature for 6 h. The reaction solution was extracted with ethyl acetate. Organic phases were combined, concentrated under a reduced pressure, and then purified with silica gel column to obtain a white solid (0.31 g, 89.7%).

$^1$H NMR (400 MHz, DMSO-$d_6$) δ 10.41 (s, 1H), 8.28 (s, 2H), 8.11 (s, 1H), 7.76 (dd, J=7.6, 1.8 Hz, 1H), 7.70 (ddd, J=8.8, 7.3, 1.9 Hz, 1H), 7.32 (d, J=8.4 Hz, 1H), 7.15 (t, J=7.5 Hz, 1H), 5.48 (s, 2H).

MS (ESI): m/z 349.06 $[M+H]^+$;

Step 2) 2-(3,5-bistrifluoromethylbenzyloxy)benzaldehyde (0.17 g, 0.5 mmol), ethanolamine (0.09 ml, 1.5 mmol), acetic acid (0.17 mL, 1.5 mmol) and THF (10 mL) were sequentially added into a 100 mL three-neck round-bottom flask under a nitrogen protection, and reacted at room temperature for 1 h. Sodium triacetoxyborohydride (0.33 g, 1.5 mol) was added and reacted for 24 h. The reaction solution was extracted with ethyl acetate, and a saturated sodium bicarbonate solution was added to adjust pH to weakly basic. Organic phases were combined and purified by silica gel column chromatography to obtain an orange solid (0.11 g, 56.0%).

$^1$H NMR (400 MHz, DMSO-$d_6$) δ 8.19 (s, 2H), 8.08 (s, 1H), 7.35 (dd, J=7.4, 1.7 Hz, 1H), 7.25 (td, J=7.8, 1.8 Hz, 1H), 7.05 (d, J=8.2 Hz, 1H), 6.96 (t, J=7.4 Hz, 1H), 5.34 (s, 2H), 4.71-4.32 (m, 1H), 3.79 (s, 2H), 3.47 (t, J=5.7 Hz, 2H), 2.61 (t, J=5.7 Hz, 2H).

MS (ESI): m/z 394.12 $[M+H]^+$.

Example 18. Preparation of Compound (17)

(17) MZ66

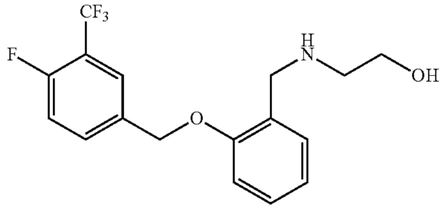

Step 1) 4-fluoro-3-trifluoromethylbenzyl bromide (0.18 mL, 1.2 mmol), 2-hydroxybenzaldehyde (0.12 g, 1 mmol), potassium carbonate (0.41 g, 3 mmol) and DMF (10 mL) were added to a 100 ml single-neck round-bottom flask, reacted at room temperature for 6 h, and extracted with ethyl acetate. Organic phases were combined, concentrated under a reduced pressure, and then purified with silica gel column to obtain a white solid (0.25 g, 82.3%).

$^1$H NMR (400 MHz, DMSO-$d_6$) δ 10.41 (d, J=0.8 Hz, 1H), 7.95 (ddd, J=16.5, 7.4, 2.2 Hz, 2H), 7.74 (dd, J=7.7, 1.8 Hz, 1H), 7.68 (ddd, J=8.9, 7.4, 1.9 Hz, 1H), 7.57 (dd, J=10.8, 8.5 Hz, 1H), 7.32 (d, J=8.4 Hz, 1H), 7.13 (t, J=7.5 Hz, 1H), 5.35 (s, 2H).

MS (ESI): m/z 299.07 $[M+H]^+$;

Step 2) 2-(4-fluoro-3-trifluoromethylbenzyloxy)benzaldehyde (0.15 g, 0.5 mmol), ethanolamine (0.09 ml, 1.5 mmol), acetic acid (0.17 mL, 1.5 mmol) and THF (10 mL) were sequentially added into a 100 mL three-neck round-bottom flask under a nitrogen protection, and reacted at room temperature for 1 hr. Sodium triacetoxyborohydride (0.33 g, 1.5 mol) was added and reacted for 24 h. The reaction solution was extracted with ethyl acetate, and a saturated sodium bicarbonate solution was added to adjust pH to weakly basic. Organic phases were combined and purified by silica gel column chromatography to obtain a white solid (0.10 g, 58.3%).

$^1$H NMR (400 MHz, DMSO-$d_6$) δ 7.92-7.84 (m, 2H), 7.55 (dd, J=10.9, 8.6 Hz, 1H), 7.33 (d, J=7.3 Hz, 1H), 7.23 (t, J=7.8 Hz, 1H), 7.05 (d, J=8.2 Hz, 1H), 6.94 (t, J=7.4 Hz, 1H), 5.20 (s, 2H), 4.50 (s, 1H), 3.75 (s, 2H), 3.46 (s, 2H), 2.58 (d, J=5.6 Hz, 2H).

MS (ESI): m/z 344.13 $[M+H]^+$.

Example 19. Preparation of Compound (18)

(18) MZ5

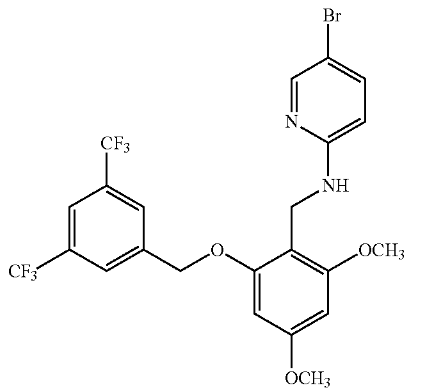

3,5-bistrifluoromethylbenzyl bromide (0.22 mL, 1.2 mmol), 4,6-dimethoxysalicylaldehyde (0.18 g, 1 mmol), potassium carbonate (0.41 g, 3 mmol) and DMF (10 mL) was successively added to a 100 ml single-neck round-bottom flask, reacted at room temperature for 6 h, and extracted with ethyl acetate. Organic phases were combined, concentrated under a reduced pressure, and purified by silica gel column to obtain a white solid (0.44 g, 89.4%).

$^1$H NMR (400 MHz, $CDCl_3$) δ 10.42 (s, 1H), δ 7.93 (s, 2H), 7.84 (s, 1H), 6.18 (d, J=2.2 Hz, 1H), 6.15 (d, J=2.3 Hz, 1H), 5.15 (s, 2H),

MS (ESI): m/z 409.08 $[M+H]^+$;

Step 2) 2-(3,5-bistrifluoromethylbenzyloxy)-4,6-dimethoxysalicylaldehyde (0.20 g, 0.49 mmol), 2-amino-5-bromopyridine (0.26 g, 1.5 mmol), acetic acid (0.17 mL, 1.5 mmol) and THF (10 mL) were successively added to a 100 mL three-neck round-bottom flask under a nitrogen protection, and reacted at room temperature for 1 h. Sodium triacetoxyborohydride (0.33 g, 1.5 mmol) was added and reacted for 24 h. The reaction solution was extracted with ethyl acetate and a saturated sodium bicarbonate solution was added to adjust pH to weakly alkaline. Organic phases were combined, and purified by silica gel column chromatography to obtain a white solid (0.16 g, 58.6%).

$^1$H NMR (400 MHz, Chloroform-d) δ 8.04 (d, J=2.4 Hz, 1H), 7.90 (s, 2H), 7.85 (s, 1H), 7.40 (dd, J=8.9, 2.5 Hz, 1H), 6.43 (d, J=8.9 Hz, 1H), 6.19 (d, J=2.2 Hz, 1H), 6.13 (d, J=2.2 Hz, 1H), 5.17 (s, 2H), 4.46 (d, J=5.9 Hz, 2H), 3.85 (s, 3H), 3.79 (s, 3H).

MS (ESI): m/z 565.05 $[M+H]^+$.

Example 20. Preparation of Compound (19)

(19) MZ71

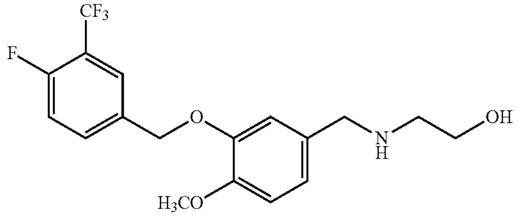

Step 1) 4-fluoro-3-trifluoromethylbenzyl bromide (0.18 mL, 1.2 mmol), 3-hydroxy-4-methoxybenzaldehyde (0.15 g, 1 mmol), potassium carbonate (0.41 g, 3 mmol) and DMF (10 mL) were sequentially added to a 100 mL single-neck round-bottom flask, reacted at room temperature for 6 h, and extracted with ethyl acetate. Organic phases were combined, concentrated under a reduced pressure, and then purified by silica gel column to obtain a white solid (0.25 g, 79.2%).

$^1$H NMR (400 MHz, DMSO-$d_6$) δ 9.85 (s, 1H), 7.91 (dd, J=7.1, 2.2 Hz, 1H), 7.86 (ddd, J=7.7, 4.9, 2.1 Hz, 1H), 7.61 (dd, J=8.4, 2.0 Hz, 1H), 7.58-7.54 (m, 1H), 7.52 (d, J=1.9 Hz, 1H), 7.23 (d, J=8.3 Hz, 1H), 5.24 (s, 2H), 3.89 (s, 3H).

MS (ESI): m/z 329.08 $[M+H]^+$;

Step 2) 3-((4-fluoro-3-(trifluoromethyl)benzyl)oxy)-4-methoxybenzaldehyde (0.16 g, 0.5 mmol), ethanolamine (0.09 ml, 1.5 mmol), acetic acid (0.17 mL, 1.5 mmol) and THF (10 mL) were sequentially added to a 100 mL three-neck round-bottom flask under a nitrogen protection, and reacted at room temperature for 1 h. Sodium triacetoxyborohydride (0.33 g, 1.5 mol) was added and reacted for another 24 h. The reaction solution was extracted with ethyl acetate, a saturated sodium bicarbonate solution was added to adjust pH to weak alkaline, and organic phases were combined and purified by silica gel column chromatography to obtain an orange solid (0.10 g, 53.6%).

$^1$H NMR (400 MHz, DMSO-$d_6$) δ 7.88 (dd, J=7.3, 2.1 Hz, 1H), 7.82 (ddd, J=7.6, 5.0, 2.1 Hz, 1H), 7.54 (dd, J=10.9, 8.6 Hz, 1H), 7.06 (d, J=1.8 Hz, 1H), 6.92 (d, J=8.2 Hz, 1H), 6.88 (dd, J=8.3, 1.8 Hz, 1H), 5.13 (s, 2H), 3.74 (s, 3H), 3.64 (s, 2H), 3.45 (t, J=5.7 Hz, 2H), 2.53 (t, J=5.8 Hz, 2H).

MS (ESI): m/z 374.14 $[M+H]^+$.

Example 21. Preparation of Compound (20)

(20) MZ33

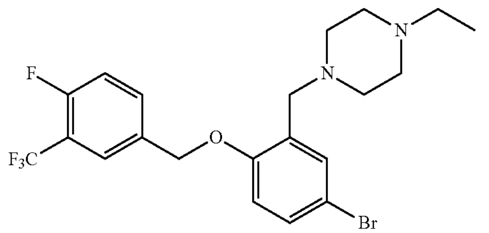

Step 1) 4-fluoro-3-trifluoromethylbenzyl bromide (0.19 mL, 1.2 mmol), 2-hydroxy-5-bromobenzaldehyde (0.20 g, 1 mmol), potassium carbonate (0.41 g, 3 mmol) and DMF (10 mL) were successively added to a 100 ml single-neck round-bottom flask, reacted at room temperature for 6 hours, and extracted with ethyl acetate. Organic phases were combined, concentrated under a reduced pressure, and then purified by silica gel column to obtain a white solid (0.32 g, 85.3%).

$^1$H NMR (400 MHz, $CDCl_3$) δ 10.42 (s, 1H), 7.96 (d, J=2.6 Hz, 1H), 7.65 (dtd, J=13.1, 5.5, 4.3, 2.3 Hz, 3H), 7.28 (d, J=9.5 Hz, 1H), 6.93 (d, J=8.8 Hz, 1H), 5.17 (s, 2H).

MS (ESI): m/z 376.97 $[M+H]^+$;

Step 2) 2-(4-fluoro-3-trifluoromethylbenzyloxy)-5-bromobenzaldehyde (0.19 g, 0.5 mmol), N-ethylpiperazine (0.19 mL, 1.5 mmol), acetic acid (0.17 mL), 1.5 mmol) and THF (10 mL) were successively added to a 100 mL three-neck round-bottom flask under a nitrogen protection, and reacted at room temperature for 1 h. Sodium triacetoxyborohydride (0.33 g, 1.5 mmol) was added and reacted for 24 h. The reaction solution was extracted with ethyl acetate, a saturated sodium bicarbonate solution was added to adjust pH to weakly alkaline, and organic phases were combined and purified by silica gel column chromatography to obtain a white solid (0.11 g, 54.62%).

1H NMR (400 MHz, $CDCl_3$) δ 7.68-7.60 (m, 2H), 7.49 (d, J=2.6 Hz, 1H), 7.30 (dd, J=8.7, 2.6 Hz, 1H), 7.25-7.18 (m, 1H), 6.75 (d, J=8.7 Hz, 1H), 5.03 (s, 2H), 3.54 (s, 2H), 2.70-2.44 (m, 8H), 2.41 (q, J=7.2 Hz, 2H), 1.07 (t, J=7.2 Hz, 3H).

MS (ESI): m/z 379.00 $[M+H]^+$.

Example 22. Preparation of Compound (21)

(21) MZ74

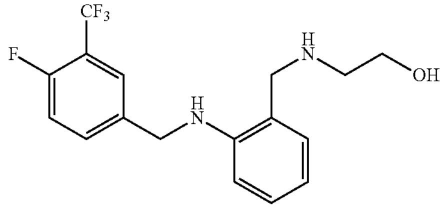

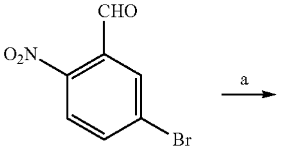

1

-continued

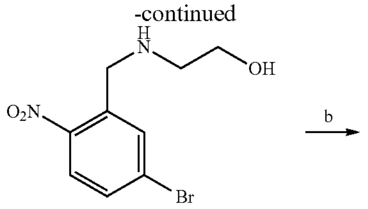

2

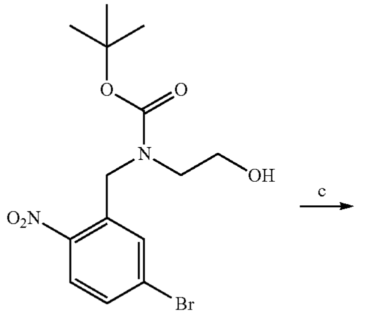

3

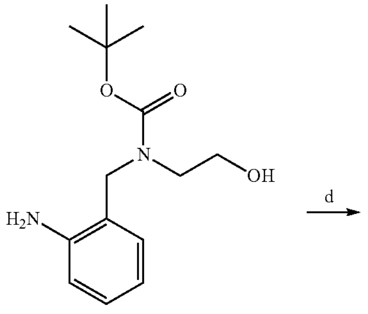

4

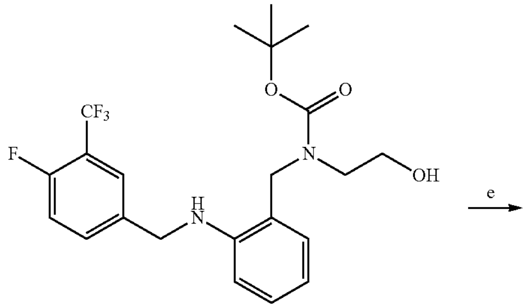

5

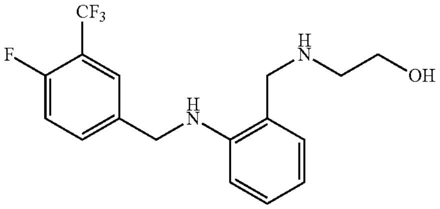

MZ74 a) Under $N_2$ protection, compound 1 (0.69 g, 3 mmol) and DCM (20 mL) were added to a 100 mL double-neck round-bottom flask, and then ethanolamine (0.54 mL, 9 mmol) and acetic acid (0.17 mL, 1.5 mmol) were added, and reacted at room temperature for 2 h. Sodium triacetoxyborohydride (1.27 g, 6 mmol) was added, and the reaction was completed as being detected by TLC, quenched with a saturated sodium bicarbonate solution, and extracted with ethyl acetate. Organic phases were combined and purified by silica gel column normal phase chromatography to obtain compound 2 (0.70 g, 84.9%).

$^1$H NMR (400 MHz, DMSO-d$_6$) δ 7.98 (d, J=2.2 Hz, 1H), 7.91 (d, J=8.6 Hz, 1H), 7.72 (dd, J=8.6, 2.3 Hz, 1H), 4.51 (t, J=5.3 Hz, 1H), 3.97 (s, 2H), 3.44 (q, J=5.4 Hz, 2H), 2.55 (t, J=5.8 Hz, 2H).

b) Compound 2 (0.41 g, 1.5 mmol) was placed in a 100 mL round-bottom flask, and DCM (10 mL) and di-tert-butyl dicarbonate (0.69 mL, 0.3 mmol) were successively added and reacted at room temperature until the completion of the reaction was detected by TLC. The reaction was quenched by adding water, and extracted with ethyl acetate. Organic phases were combined, and purified by normal phase chromatography on silica gel column to obtain compound 3 (0.50 g, 87.8%).

$^1$H NMR (400 MHz, DMSO-d$_6$) δ 8.06-7.95 (m, 1H), 7.77 (dd, J=8.7, 2.2 Hz, 1H), 7.52 (d, J=46.6 Hz, 1H), 4.74 (t, J=5.2 Hz, 2H), 4.70 (s, 1H), 3.51 (q, J=5.6 Hz, 2H), 3.28 (t, 2H), 1.50-1.15 (m, 9H).

c) Under H2 condition, compound 3 (0.37 g, lmmol), 10% Pd/C (100 mg) and MeOH (10 mL) were added to a 100 round-bottom flask, and reacted at room temperature until the completion of the reaction as being detected by TLC. The reaction solution was filtered, and extracted with ethyl acetate. Organic phases were combined and purified by normal phase chromatography on silica gel to obtain compound 4 (0.17 g, 62.7%).

$^1$H NMR (400 MHz, DMSO-d$_6$) δ 6.97 (t, J=7.5 Hz, 1H), 6.92 (s, 2H), 6.61 (d, J=7.9 Hz, 1H), 6.52 (d, J=7.5 Hz, 1H), 4.68 (s, 1H), 4.29 (s, 2H), 3.43 (q, J=5.7 Hz, 2H), 3.16-3.04 (m, 2H), 1.39 (d, J=14.6 Hz, 9H).

d) Under $N_2$ protection, 3-trifluoromethyl-4-fluorobenzaldehyde (0.12 g, 0.6 mmol) and DCM (10 mL) were added to a 100 mL two-neck round-bottom flask. And compound 4 (0.32 g, 1.2 mmol), acetic acid (0.03 ml, 0.3 mmol) were added and reacted at room temperature for 2 h. Sodium triacetoxyborohydride (0.25 g, 1.2 mmol) was added, and the reaction was completed as being detected by TLC, quenched with saturated sodium bicarbonate solution, and extracted with ethyl acetate. Organic phases were combined and purified by silica gel column normal phase chromatography to obtain compound 5 (0.19 g, 72.6%).

$^1$H NMR (400 MHz, DMSO-d$_6$) δ 7.68 (dd, J=8.8, 5.4 Hz, 2H), 7.51-7.41 (m, 1H), 7.03 (t, J=7.6 Hz, 2H), 6.58 (t, J=7.3 Hz, 1H), 6.46 (d, J=8.1 Hz, 1H), 6.03 (s, 1H), 4.71 (t, J=5.4 Hz, 1H), 4.41 (d, J=5.9 Hz, 5H), 3.45 (q, J=6.2 Hz, 2H), 3.12 (s, 2H), 1.33 (s, 9H).

e) Compound 5 (0.15 g, 0.35 mmol) was placed in a 100 mL round-bottom flask, and DCM (10 mL) and 2 mL of trifluoroacetic acid were successively added. The reaction was carried out at room temperature for 1 h, quenched with a saturated sodium bicarbonate solution, and extracted with ethyl acetate. Organic phases were combined, and purified by normal phase chromatography on silica gel column to obtain compound MZ74 (0.1 g, 81.8%).

$^1$H NMR (400 MHz, DMSO-d$_6$) δ 7.69 (dd, J=8.7, 5.4 Hz, 2H), 7.52 (m, 1H), 7.05 (t, J=7.6 Hz, 2H), 6.58 (t, J=7.3 Hz, 1H), 6.46 (d, J=8.1 Hz, 1H), 6.03 (s, 1H), 4.71 (t, J=5.4 Hz, 1H), 4.41 (d, J=5.9 Hz, 5H), 3.44 (q, J=6.3 Hz, 2H), 3.14 (s, 2H).

Example 23. Preparation of Compound (22)

(22) MZ68

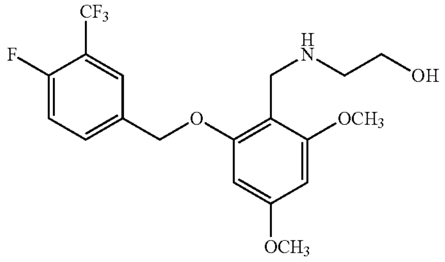

Step 1) 4-fluoro-3-trifluoromethylbenzyl bromide (0.18 mL, 1.2 mmol), 2-hydroxy-4,6-dimethoxybenzaldehyde (0.18 g, 1 mmol), potassium carbonate (0.41 g, 3 mmol) and DMF (10 mL) were sequentially added to a 100 mL single-neck round-bottom flask, reacted at room temperature for 6 h, and extracted with ethyl acetate. Organic phases were combined, concentrated under a reduced pressure, and then purified by silica gel column to obtain a white solid (0.30 g, 83.4%).

$^1$H NMR (400 MHz, DMSO-d$_6$) δ 10.27 (s, 1H), 8.03 (dd, J=7.1, 2.2 Hz, 1H), 7.89 (ddd, J=7.9, 5.0, 2.1 Hz, 1H), 7.56 (dd, J=10.8, 8.6 Hz, 1H), 6.38 (d, J=2.1 Hz, 1H), 6.32 (d, J=2.1 Hz, 1H), 5.27 (s, 2H), 3.88 (s, 3H), 3.85 (s, 3H).

MS (ESI): m/z 359.09 $[M+H]^+$;

Step 2) 2-(4-fluoro-3-trifluoromethylbenzyloxy)-4,6-dimethoxybenzaldehyde (0.18 g, 0.5 mmol), ethanolamine (0.09 ml, 1.5 mmol), acetic acid (0.17 mL, 1.5 mmol) and THF (10 mL) were sequentially added to a 100 mL three-neck round-bottom flask under a nitrogen protection, and reacted at room temperature for 1 h. Sodium triacetoxyborohydride (0.33 g, 1.5 mol) was added and reacted for another 24 h. The reaction solution was extracted with ethyl acetate, a saturated sodium bicarbonate solution was added to adjust pH to weakly alkaline, and organic phases were combined, and purified by silica gel column chromatography to obtain an orange solid (0.11 g, 54.5%).

$^1$H NMR (400 MHz, DMSO-d$_6$) δ 7.95 (dd, J=12.7, 7.7 Hz, 2H), 7.86 (d, J=8.3 Hz, 1H), 7.56 (dd, J=10.9, 8.5 Hz, 1H), 6.33 (ddd, J=25.9, 23.3, 2.1 Hz, 2H), 5.23 (s, 2H), 4.02 (s, 2H), 3.83 (s, 3H), 3.80 (s, 3H), 2.84 (t, J=5.4 Hz, 2H).

MS (ESI): m/z 404.15 $[M+H]^+$.

Example 24. Preparation of Compound (23)

(23) MZ72

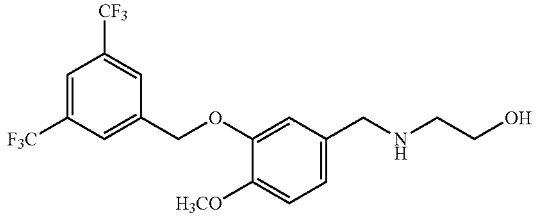

Step 1) 3,5-bistrifluoromethylbenzyl bromide (0.22 mL, 1.2 mmol), 4-methoxy-3-hydroxybenzaldehyde (0.15 g, 1 mmol), potassium carbonate (0.41 g, 3 mmol) and DMF (10 mL)) were sequentially added to a 100 ml single-neck round-bottom flask, reacted at room temperature for 6 h, and extracted with ethyl acetate. Organic phases were combined, concentrated under a reduced pressure, and then purified by silica gel column to obtain a white solid (0.30 g, 80.7%).

$^1$H NMR (400 MHz, DMSO-$d_6$) δ 9.85 (s, 1H), 8.19 (s, 2H), 8.11 (s, 1H), 7.63 (dd, J=8.3, 1.9 Hz, 1H), 7.54 (d, J=1.8 Hz, 1H), 7.25 (d, J=8.3 Hz, 1H), 5.38 (s, 2H), 3.90 (s, 3H).

MS (ESI): m/z 379.08 $[M+H]^+$;

Step 2) 2-(3,5-bistrifluoromethylbenzyloxy)-4-methoxy-3-hydroxybenzaldehyde (0.19 g, 0.5 mmol), ethanolamine (0.09 ml, 1.5 mmol), acetic acid (0.17 mL, 1.5 mmol) and THF (10 mL) were sequentially added to a 100 mL three-neck round-bottom flask under a nitrogen protection, and reacted at room temperature for 1 h. Sodium triacetoxyborohydride (0.33 g, 1.5 mol) was added and reacted for 24 h. The reaction solution was extracted with ethyl acetate, a saturated sodium bicarbonate solution was added to adjust pH to weakly alkaline, and organic phases were combined and purified by silica gel column chromatography to obtain an orange solid (0.11 g, 51.2%).

$^1$H NMR (400 MHz, DMSO-$d_6$) δ 8.16 (s, 2H), 8.08 (s, 1H), 7.12 (d, J=1.8 Hz, 1H), 6.96 (d, J=8.2 Hz, 1H), 6.92 (dd, J=8.3, 1.7 Hz, 1H), 5.28 (s, 2H), 3.76 (s, 3H), 3.69 (s, 2H), 3.46 (t, J=5.7 Hz, 2H), 2.57 (t, J=5.7 Hz, 2H).

MS (ESI): m/z 424.13 $[M+H]^+$.

Example 25. Preparation of Compound (24)

(24) MZ41

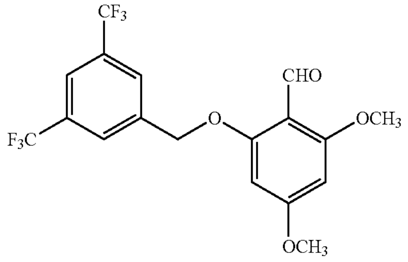

3,5-bistrifluoromethylbenzyl bromide (0.22 mL, 1.2 mmol), 4,6-dimethoxysalicylaldehyde (0.18 g, 1 mmol), potassium carbonate (0.41 g, 3 mmol), and DMF were sequentially added in a 100 ml single-neck round-bottom flask, reacted at room temperature for 6 h, and extracted with ethyl acetate. Organic phases were combined, concentrated under a reduced pressure, and then purified with silica gel column to obtain a white solid (0.44 g, 89.4%).

$^1$H NMR (400 MHz, $CDCl_3$) δ 10.42 (s, 1H), δ 7.93 (s, 2H), 7.84 (s, 1H), 6.18 (d, J=2.2 Hz, 1H), 6.15 (d, J=2.3 Hz, 1H), 5.15 (s, 2H),

MS (ESI): m/z 409.08 $[M+H]^+$.

Example 26. Preparation of Compound (25)

(25) MZ43

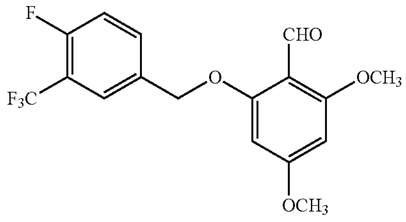

4-fluoro-3-trifluoromethylbenzyl bromide (0.18 mL, 1.2 mmol), 4,6-dimethoxysalicylaldehyde (0.18 g, 1 mmol), potassium carbonate (0.41 g, 3 mmol) and DMF (10 mL)) were successively added to a 100 ml single-neck round-bottom flask, reacted at room temperature for 6 h, and extracted with ethyl acetate. Organic phases were combined, concentrated under a reduced pressure, and then purified by silica gel column to obtain a white solid (0.29 g, 80.9%).

1H NMR (400 MHz, $CDCl_3$) δ 10.42 (s, 1H), 7.95-7.92 (m, 2H), 7.86 (s, 1H), 7.17 (d, J=8.1 Hz, 1H), 7.07 (d, J=1.9 Hz, 1H), 6.96 (dd, J=8.2, 1.9 Hz, 1H), 6.53 (t, J=74.3 Hz, 1H), 5.23 (s, 2H);

MS (ESI): m/z 359.09 $[M+H]^+$.

Example 27. Preparation of Compound (26)

(26) MZ38

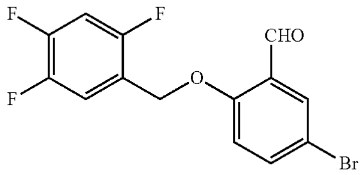

2,4,5-trifluorobenzyl bromide (0.16 mL, 1.2 mmol), 5-bromosalicylaldehyde (0.20 g, 1 mmol), potassium carbonate (0.41 g, 3 mmol) and DMF (10 mL) were successively added into a 100 ml single-neck round-bottom flask, reacted at room temperature for 6 h, and extracted with ethyl acetate. Organic phases were combine, concentrated under a reduced pressure, and then purified by silica gel column to obtain a white solid (0.29 g, 84.0%).

$^1$H NMR (400 MHz, $CDCl_3$) δ 10.42 (s, 1H), δ 7.36 (ddd, J=10.3, 8.7, 6.6 Hz, 1H), 7.11 (d, J=8.1 Hz, 1H), 7.04 (d, J=1.9 Hz, 1H), 7.01-6.93 (m, 1H), 6.91 (dd, J=8.1, 1.9 Hz, 1H), 6.51 (t, J=74.8 Hz, 1H), 5.11 (q, J=1.0 Hz, 2H).

MS (ESI): m/z 344.97 $[M+H]^+$.

Example 28. Preparation of Compound (27)

(27) MZ40

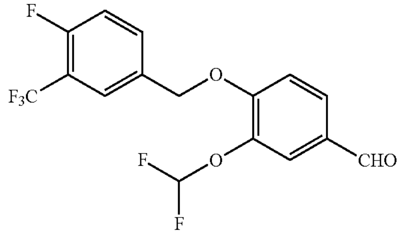

4-fluoro-3-trifluoromethylbenzyl bromide (0.18 mL, 1.2 mmol), 4-hydroxy-3-difluoromethoxybenzaldehyde (0.19 g, 1 mmol), potassium carbonate (0.41 g, 3 mmol), and DMF (10 mL) were sequentially added to a 100 mL single-neck round-bottom flask, reacted at room temperature for 6 h, and extracted with ethyl acetate. Organic phases were combined, concentrated under a reduced pressure, and then purified by silica gel column to obtain a white solid (0.29 g, 79.6%).

$^1$H NMR (400 MHz, $CDCl_3$) δ 10.42 (s, 1H), 7.95-7.92 (m, 2H), 7.86 (s, 1H), 7.17 (d, J=8.1 Hz, 1H), 7.07 (d, J=1.9 Hz, 1H), 6.96 (dd, J=8.2, 1.9 Hz, 1H), 6.53 (t, J=74.3 Hz, 1H), 5.23 (s, 2H);

MS (ESI): m/z 365.06 [M+H]$^+$.

Example 29. Preparation of Compound (28)

(28) MZ69

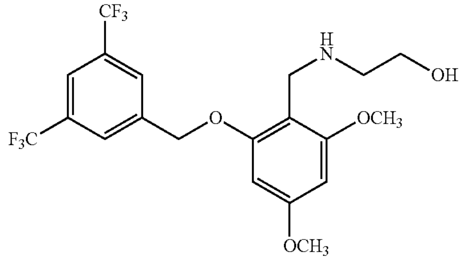

Step 1) 3,5-bistrifluoromethylbenzyl bromide (0.22 mL, 1.2 mmol), 2-hydroxy-4,6-dimethoxybenzaldehyde (0.18 g, 1 mmol), potassium carbonate (0.41 g, 3 mmol), and DMF (10 mL) were successively added to a 100-ml single-neck round-bottom flask, reacted at room temperature for 6 h, and extracted with ethyl acetate. Organic phases were combined, concentrated under a reduced pressure, and purified by silica gel column to obtain a white solid (0.33 g, 81.5%).

$^1$H NMR (400 MHz, $CDCl_3$) δ 10.42 (s, 1H), 7.95-7.92 (m, 2H), 7.86 (s, 1H), 7.17 (d, J=8.1 Hz, 1H), 7.07 (d, J=1.9 Hz, 1H), 6.96 (dd, J=8.2, 1.9 Hz, 1H), 6.53 (t, J=74.3 Hz, 1H), 5.23 (s, 2H);

MS (ESI): m/z 409.09 [M+H]$^+$;

Step 2) 2-(3,5-bistrifluoromethylbenzyloxy)-4,6-dimethoxybenzaldehyde (0.20 g, 0.5 mmol), ethanolamine (0.09 ml, 1.5 mmol), acetic acid (0.17 mL, 1.5 mmol), and THF (10 mL) were successively added to a 100 mL three-neck round-bottom flask under a nitrogen protection, and reacted at room temperature for 1 hr. Sodium triacetoxyborohydride (0.33 g, 1.5 mol) was added and reacted for another 24 h. The reaction solution was extracted with ethyl acetate, a saturated sodium bicarbonate solution was added to adjust pH to weakly alkaline, and organic phases were combined and purified by silica gel column chromatography to obtain an orange solid (0.11 g, 50.8%).

$^1$H NMR (400 MHz, DMSO-$d_6$) δ 8.18 (s, 2H), 8.08 (s, 1H), 6.32 (d, J=2.1 Hz, 1H), 6.26 (d, J=2.1 Hz, 1H), 5.32 (s, 2H), 3.77 (s, 3H), 3.75 (s, 3H), 3.69 (s, 2H), 3.41 (t, J=5.6 Hz, 2H), 2.55-2.51 (m, 3H).

MS (ESI): m/z 454.15 [M+H]$^+$.

Example 30. Preparation of Compound (29)

(29) MZ42

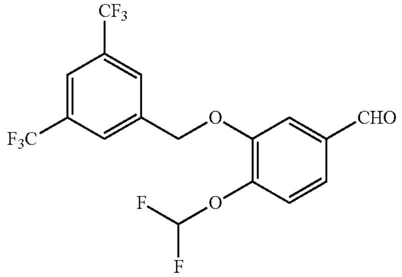

3,5-bistrifluoromethylbenzyl bromide (0.22 mL, 1.2 mmol), 4-difluoromethoxy-3-hydroxybenzaldehyde (0.13 g, 1 mol), potassium carbonate (0.41 g, 3 mmol), and DMF (10 mL) were sequentially added to a 100 mL single-neck round-bottom flask, reacted at room temperature for 6 h, and extracted with ethyl acetate. Organic phases were combined, concentrated under a reduced pressure, and purified by silica gel column to obtain a white solid (0.37 g, 89.3%).

$^1$H NMR (400 MHz, $CDCl_3$) δ 10.42 (s, 1H), 7.95-7.92 (m, 2H), 7.86 (s, 1H), 7.17 (d, J=8.1 Hz, 1H), 7.07 (d, J=1.9 Hz, 1H), 6.96 (dd, J=8.2, 1.9 Hz, 1H), 6.53 (t, J=74.3 Hz, 1H), 5.23 (s, 2H);

MS (ESI): m/z 415.05 [M+H]$^+$.

Example 31. Preparation of Compound (30)

(30) MZ35

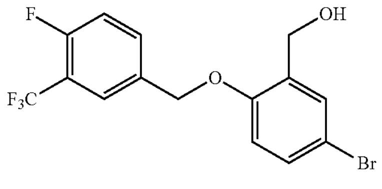

Step 1) 4-fluoro-3-trifluoromethylbenzyl bromide (0.19 mL, 1.2 mmol), 2-hydroxy-5-bromobenzaldehyde (0.20 g, 1 mmol), potassium carbonate (0.41 g, 3 mmol), and DMF (10 mL) were successively added to a 100 ml single-neck round-bottom flask, reacted at room temperature for 6 hours, and extracted with ethyl acetate. Organic phases were combined, concentrated under a reduced pressure, and then purified by silica gel column to obtain a white solid (0.32 g, 85.3%).

$^1$H NMR (400 MHz, $CDCl_3$) δ 10.42 (s, 1H), 7.96 (d, J=2.6 Hz, 1H), 7.65 (dtd, J=13.1, 5.5, 4.3, 2.3 Hz, 3H), 7.28 (d, J=9.5 Hz, 1H), 6.93 (d, J=8.8 Hz, 1H), 5.17 (s, 2H).

MS (ESI): m/z 376.97 [M+H]$^+$;

Step 2) 2-(4-fluoro-3-trifluoromethylbenzyloxy)-5-bromobenzaldehyde (0.19 g, 0.5 mmol), N-ethylpiperazine (0.19 mL, 1.5 mmol), acetic acid (0.17 mL, 1.5 mmol), and THF (10 mL) were successively added to a 100 mL three-neck round-bottom flask under a nitrogen protection, and reacted for 1 h at room temperature. Sodium borohydride (0.05 g, 1.5 mmol) was added and reacted for 24 h, and extracted with ethyl acetate. A saturated sodium bicarbonate solution was added to adjust pH to weakly alkaline, and organic phases were combined and purified by silica gel column chromatography to obtain a white solid (0.065 g, 29.9%). This compound was a by-product of MZ33.

$^1$H NMR (400 MHz, $CDCl_3$) δ 7.66 (dd, J=6.6, 2.2 Hz, 1H), 7.60 (ddd, J=7.1, 4.6, 2.2 Hz, 1H), 7.51 (d, J=2.5 Hz, 1H), 7.37 (dd, J=8.7, 2.5 Hz, 1H), 7.23 (d, J=9.2 Hz, 1H), 6.78 (d, J=8.7 Hz, 1H), 5.08 (s, 2H), 4.71 (d, J=6.3 Hz, 2H).

MS (ESI): m/z 475.11 $[M+H]^+$.

Example 32. Preparation of Compound (31)

(31) MZ36

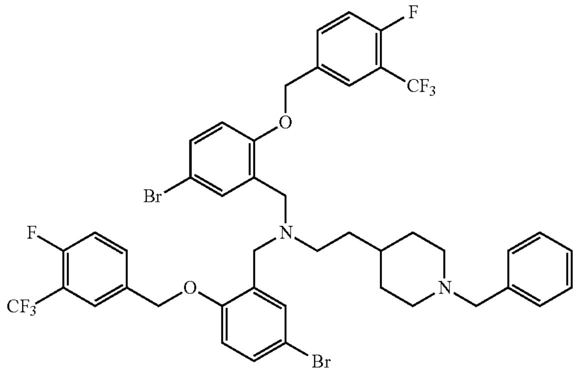

4-fluoro-3-trifluoromethylbenzyl bromide (0.19 mL, 1.2 mmol), 2-hydroxy-5-bromobenzaldehyde (0.20 g, 1 mmol), potassium carbonate (0.41 g, 3 mmol), and DMF (10 mL) were successively added to a 100 ml single-neck round-bottom flask, reacted at room temperature for 6 hours, and extracted with ethyl acetate. Organic phases were combined, concentrated under a reduced pressure, and then purified by silica gel column to obtain a white solid (0.32 g, 85.3%).

$^1$H NMR (400 MHz, $CDCl_3$) δ 10.42 (s, 1H), 7.96 (d, J=2.6 Hz, 1H), 7.65 (dtd, J=13.1, 5.5, 4.3, 2.3 Hz, 3H), 7.28 (d, J=9.5 Hz, 1H), 6.93 (d, J=8.8 Hz, 1H), 5.17 (s, 2H).

MS (ESI): m/z 376.97 $[M+H]^+$;

Step 2) 2-(4-fluoro-3-trifluoromethylbenzyl)-5-bromobenzaldehyde (0.19 g, 0.5 mmol), 4-(2-aminoethyl)-1-benzylpiperidine (0.33 g, 1.5 mmol), acetic acid (0.17 mL, 1.5 mmol), and THF (10 mL) were successively added to a 100 mL three-neck round-bottom flask under a nitrogen protection, and reacted at room temperature for 1 h. Sodium triacetoxyborohydride (0.33 g, 1.5 mmol) was added and reacted for another 24 h. The reaction solution was extracted with ethyl acetate, a saturated sodium bicarbonate solution was added to adjust pH to weakly alkaline. Organic phases were combined, and purified by silica gel column chromatography to obtain a white solid (0.21 g, 44.82%).

$^1$H NMR (400 MHz, Chloroform-d) δ 7.63 (dd, J=6.9, 2.2 Hz, 2H), 7.58-7.52 (m, 4H), 7.32 (d, J=4.4 Hz, 4H), 7.26-7.22 (m, 3H), 7.22-7.15 (m, 2H), 6.68 (d, J=8.7 Hz, 2H), 5.01 (s, 4H), 3.60 (s, 6H), 3.01-2.85 (m, 2H), 2.46 (t, J=7.1 Hz, 2H), 2.01 (d, J=5.1 Hz, 3H).

MS (ESI): m/z 941.14.00 $[M+H]^+$.

Example 33. Preparation of Compound (32)

(32) MZ37

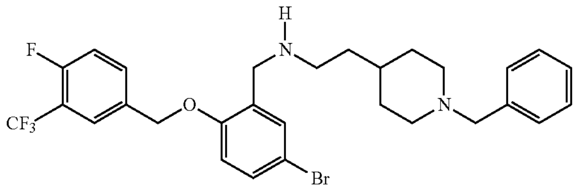

4-fluoro-3-trifluoromethylbenzyl bromide (0.19 mL, 1.2 mmol), 2-hydroxy-5-bromobenzaldehyde (0.20 g, 1 mmol), potassium carbonate (0.41 g, 3 mmol), and DMF (10 mL) were successively added to a 100 ml single-neck round-bottom flask, reacted at room temperature for 6 hours, and extracted with ethyl acetate. Organic phases were combined, concentrated under a reduced pressure, and then purified by silica gel column to obtain a white solid (0.32 g, 85.3%).

$^1$H NMR (400 MHz, $CDCl_3$) δ 10.42 (s, 1H), 7.96 (d, J=2.6 Hz, 1H), 7.65 (dtd, J=13.1, 5.5, 4.3, 2.3 Hz, 3H), 7.28 (d, J=9.5 Hz, 1H), 6.93 (d, J=8.8 Hz, 1H), 5.17 (s, 2H).

MS (ESI): m/z 376.97 $[M+H]^+$;

Step 2) 2-(4-fluoro-3-trifluoromethylbenzyl)-5-bromobenzaldehyde (0.19 g, 0.5 mmol), 4-(2-aminoethyl)-1-benzylpiperidine (0.33 mL, 1.5 mmol), acetic acid (0.17 mL, 1.5 mmol), and THF (10 mL) were successively added to a 100 mL three-neck round-bottom flask under a nitrogen protection, and reacted at room temperature for 1 h. Then sodium triacetoxyborohydride (0.33 g, 1.5 mol) was added and reacted for 24 h. The reaction solution was extracted with ethyl acetate, a saturated sodium bicarbonate solution was added to adjust pH to weakly alkaline, and organic phases were combined and purified by silica gel column chromatography to obtain a white solid (0.15 g, 51.77%).

$^1$H NMR (400 MHz, Chloroform-d) δ 7.67 (dd, J=6.8, 2.2 Hz, 1H), 7.60 (ddd, J=7.5, 4.7, 2.3 Hz, 1H), 7.45 (d, J=2.5 Hz, 1H), 7.39-7.27 (m, 6H), 7.23 (t, J=9.4 Hz, 1H), 6.76 (d, J=8.7 Hz, 1H), 5.06 (s, 2H), 3.79 (s, 2H), 3.58 (s, 2H), 2.94 (d, J=11.2 Hz, 2H), 2.62 (t, J=7.4 Hz, 2H), 2.01 (d, J=9.2 Hz, 2H), 1.71-1.31 (m, 7H).

MS (ESI): m/z 579.16 $[M+H]^+$.

Example 34. Preparation of Compound (33)

(33) MZ27

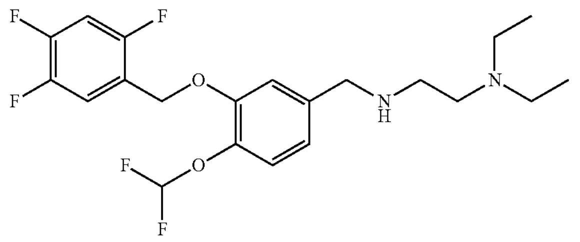

Step 1) 2,4,5-trifluorobenzyl bromide (0.16 mL, 1.2 mmol), 4-difluoromethoxy-3-hydroxybenzaldehyde (0.13 g, 1 mol), potassium carbonate (0.41 g, 3 mmol), and DMF (10 mL) were sequentially added to a 100 mL single-neck round-bottom flask, reacted at room temperature for 6 h, and extracted with ethyl acetate. Organic phases were combined, concentrated under a reduced pressure, and purified with silica gel column to obtain a white solid (0.3 g, 90.0%).

$^1H$ NMR (400 MHz, $CDCl_3$) δ 10.42 (s, 1H), δ 7.36 (ddd, J=10.3, 8.7, 6.6 Hz, 1H), 7.11 (d, J=8.1 Hz, 1H), 7.04 (d, J=1.9 Hz, 1H), 7.01-6.93 (m, 1H), 6.91 (dd, J=8.1, 1.9 Hz, 1H), 6.51 (t, J=74.8 Hz, 1H), 5.11 (q, J=1.0 Hz, 2H).

MS (ESI): m/z 333.05 $[M+H]^+$;

Step 2) 4-difluoromethoxy-3-(2,4,5-trifluorobenzyl)benzaldehyde (0.167 g, 0.5 mmol), N,N-diethylethylenediamine (0.21 mL, 1.5 mmol), acetic acid (0.17 mL, 1.5 mmol), and THF (10 mL) were sequentially added to a 100 mL three-neck round-bottom flask under a nitrogen protection, and reacted at room temperature for 1 h. Sodium triacetoxyborohydride (0.33 g, 1.5 mmol) was added and reacted for another 24 h. The reaction solution was extracted with ethyl acetate, and a saturated sodium bicarbonate solution was added to adjust pH to weakly alkaline. Organic phases were combined, and purified by silica gel column chromatography to obtain an oily liquid (0.15 g, 69.4%).

$^1H$ NMR (400 MHz, $CDCl_3$) δ 7.37 (ddd, J=10.4, 8.7, 6.6 Hz, 1H), 7.12 (d, J=8.1 Hz, 1H), 7.08 (d, J=1.9 Hz, 1H), 7.00-6.93 (m, 1H), 6.93-6.90 (m, 1H), 6.50 (t, J=74.8 Hz, 1H), 5.11 (q, J=1.0 Hz, 2H), 3.77 (s, 2H), 2.69 (td, J=5.8, 1.2 Hz, 2H), 2.62 (td, J=5.8, 1.2 Hz, 2H), 2.57 (q, J=7.2 Hz, 4H), 1.02 (t, J=7.2 Hz, 6H).

MS (ESI): m/z 433.18 $[M+H]^+$.

Example 35. Preparation of Compound (34)

(34) MZ4

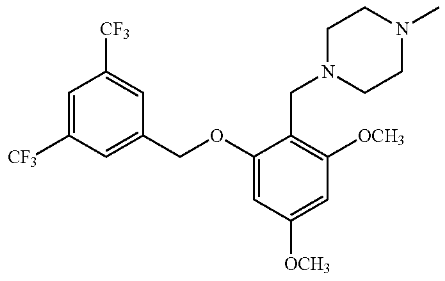

Step 1) 3,5-bistrifluoromethylbenzyl bromide (0.22 mL, 1.2 mmol), 4,6-dimethoxysalicylaldehyde (0.18 g, 1 mmol), potassium carbonate (0.41 g, 3 mmol), and DMF (10 mL) were sequentially added to a 100 ml single-neck round-bottom flask, reacted at room temperature for 6 h, and extracted with ethyl acetate. Organic phases were combined, concentrated under a reduced pressure, and then purified by silica gel column to obtain a white solid (0.44 g, 89.4%).

$^1H$ NMR (400 MHz, $CDCl_3$) δ 10.42 (s, 1H), δ 7.93 (s, 2H), 7.84 (s, 1H), 6.18 (d, J=2.2 Hz, 1H), 6.15 (d, J=2.3 Hz, 1H), 5.15 (s, 2H),

MS (ESI): m/z 409.08 $[M+H]^+$;

Step 2) 2-(3,5-bistrifluoromethylbenzyl)-4,6-dimethoxysalicylaldehyde (0.20 g, 0.49 mmol), N-methylpiperazine (0.17 mL, 1.5 mmol), acetic acid (0.17 mL, 1.5 mmol) and THF (10 mL) were sequentially added to a 100 mL three-neck round-bottom flask under a nitrogen protection, and reacted at room temperature for 1 h. Then sodium triacetoxyborohydride (0.33 g, 1.5 mmol) was added and reacted for another 24 h. The reaction solution was extracted with ethyl acetate, a saturated sodium bicarbonate solution was added to adjust pH to weakly alkaline, and organic phases were combine, and purified by silica gel column chromatography to obtain a white solid (0.19 g, 78.6%).

$^1H$ NMR (400 MHz, $CDCl_3$) δ 7.93 (s, 2H), 7.84 (s, 1H), 6.18 (d, J=2.2 Hz, 1H), 6.15 (d, J=2.3 Hz, 1H), 5.15 (s, 2H), 3.80 (s, 6H), 3.65 (s, 2H), 2.51 (d, J=53.4 Hz, 8H), 2.26 (s, 3H).

MS (ESI): m/z 493.18 $[M+H]^+$.

Example 36. Preparation of Compound (35)

(35) MZ70

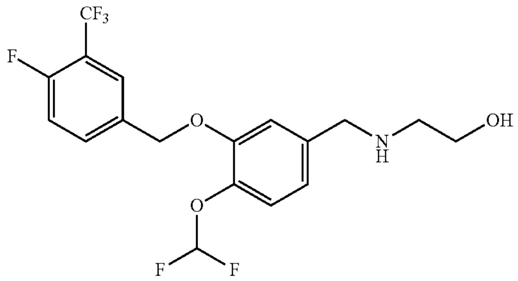

Step 1) 4-fluoro-3-trifluoromethylbenzyl bromide (0.18 mL, 1.2 mmol), 4-difluoromethoxy-3-hydroxybenzaldehyde (0.19 g, 1 mmol), potassium carbonate (0.41 g, 3 mmol), and DMF (10 mL) were successively added to a 100-ml single-neck round-bottom flask, reacted at room temperature for 6 h, and extracted with ethyl acetate. Organic phases were combined, concentrated under a reduced pressure, and purified by silica gel column to obtain a white solid (0.29 g, 79.6%).

1H NMR (400 MHz, $CDCl_3$) δ 10.42 (s, 1H), 7.95-7.92 (m, 2H), 7.86 (s, 1H), 7.17 (d, J=8.1 Hz, 1H), 7.07 (d, J=1.9 Hz, 1H), 6.96 (dd, J=8.2, 1.9 Hz, 1H), 6.53 (t, J=74.3 Hz, 1H), 5.23 (s, 2H);

MS (ESI): m/z 365.06 $[M+H]^+$;

Step 2) 4-difluoromethoxy-3-((4-fluoro-3-(trifluoromethyl)benzyl)oxy)benzaldehyde (0.18 g, 0.5 mmol), ethanolamine (0.09 ml, 1.5 mmol), acetic acid (0.17 mL, 1.5 mmol) and THF (10 mL) were successively added to a 100 mL three-neck round-bottom flask under a nitrogen protection, and reacted at room temperature for 1 h. Then sodium triacetoxyborohydride (0.33 g, 1.5 mol) was added and reacted for another 24 h. The reaction solution was extracted with ethyl acetate, a saturated sodium bicarbonate solution was added to adjust pH to weakly alkaline, and organic phases were combined and purified by silica gel column chromatography to obtain an orange solid (0.14 g, 68.4%).

$^1H$ NMR (400 MHz, $CDCl_3$) δ 7.95-7.92 (m, 2H), 7.86 (s, 1H), 7.17 (d, J=8.1 Hz, 1H), 7.07 (d, J=1.9 Hz, 1H), 6.96 (dd, J=8.2, 1.9 Hz, 1H), 6.53 (t, J=74.3 Hz, 1H), 5.23 (s, 2H), 3.80 (s, 2H), 3.71-3.65 (m, 2H), 2.82-2.79 (m, 2H).

MS (ESI): m/z 410.12 $[M+H]^+$.

Example 37. Preparation of Compound (36)

(36) MZ22

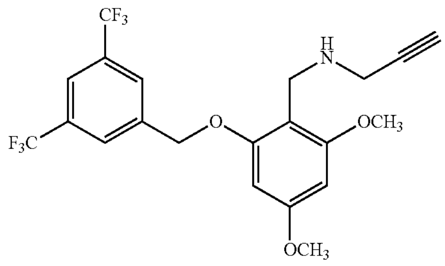

Step 1) 3,5-bistrifluoromethylbenzyl bromide (0.22 mL, 1.2 mmol), 2-hydroxy-4,6-dimethoxybenzaldehyde (0.18 g, 1 mmol), potassium carbonate (0.41 g, 3 mmol), and DMF (10 mL) were successively added to a 100-mL single-neck round-bottom flask, reacted at room temperature for 6 h, and extracted with ethyl acetate. Organic phases were combined, concentrated under a reduced pressure, and purified by silica gel column to obtain a white solid (0.34 g, 82.7%).

$^1$H NMR (400 MHz, $CDCl_3$) δ 10.42 (s, 1H), δ 7.93 (s, 2H), 7.84 (s, 1H), 6.18 (d, J=2.2 Hz, 1H), 6.15 (d, J=2.3 Hz, 1H), 5.15 (s, 2H),

MS (ESI): m/z 409.09 $[M+H]^+$;

Step 2) 2-(3,5-bistrifluoromethylbenzyloxy)-4,6-dimethoxybenzaldehyde (0.20 g, 0.5 mmol), ethanolamine (0.09 ml, 1.5 mmol), acetic acid (0.17 mL, 1.5 mmol), and THF (10 mL) were successively added to a 100 mL three-neck round-bottom flask under a nitrogen protection, and reacted for 1 hr at room temperature. Then sodium triacetoxyborohydride (0.33 g, 1.5 mmol) was added and reacted for another 24 h. The reaction solution was extracted with ethyl acetate, a saturated sodium bicarbonate solution was added to adjust pH to weakly alkaline, and organic phases were combined and purified by silica gel column chromatography to obtain an orange solid (0.12 g, 55.1%).

$^1$H NMR (400 MHz, Chloroform-d) δ 7.94-7.92 (m, 2H), 7.85 (s, 1H), 6.18 (d, J=2.2 Hz, 1H), 6.14 (d, J=2.2 Hz, 1H), 5.16 (s, 2H), 3.90 (s, 2H), 3.83 (s, 3H), 3.80 (s, 3H), 3.39 (d, J=2.5 Hz, 2H), 2.11 (t, J=2.4 Hz, 1H).

MS (ESI): m/z 448.13 $[M+H]^+$.

Example 38. Knockout of Usp25 Enhances Synaptic and Cognitive Function in AD Mice 6-7 months old WT, Usp25$^{+/-}$, 5×FAD, 5×FAD; Usp25$^{+/-}$ mice were subjected to behavioral tests related to learning and memory, including Y-maze, Morris water maze test and conditioned panic test. The mouse was touched and stroked three days before the experiment, once a day; the mouse tail was gently grabbed to pick up the mouse; and the mouse was kept on the hand for 30 seconds. On the day of the experiment, the mice for experiment were transferred to a preparation room, so that the mice could acclimate for 30 minutes. Behavioral experiments were performed daily between 9:00 a.m.-6:00 p.m. with a light intensity of 650 lux in the laboratory. Data acquisition and analysis were performed using Smart Video Tracking Software (Panlab, Harvard Apparatus).

Y-maze test was used to evaluate spontaneous spatial alternation behavior and working memory in mice. The mice were placed in the center of the Y-maze (length 30 cm, width 6 cm, height 15 cm), and then let the mice freely explore the maze for 5 mins. All four limbs of a mouse entering the maze arm was used as the standard for entering the maze arm, and the mouse entering different maze arms for three consecutive times was used as a correct autonomous alternate shuttle (Alternation).

As shown in FIG. 1A, compared with WT mice, the percentage of autonomous alternate shuttles (Alternation %) in the Y-maze for 5×FAD mice was significantly reduced, whereas after Usp25 knockout, the percentage of autonomous alternate shuttles for 5×FAD; Usp$^{25+/-}$ mice was significantly increased, suggesting that knocking out Usp25 could reverse working memory in AD mice.

The Morris water maze test was performed in a circular water tank (120 cm in diameter), the height of water filling in the water tank was preferably 1 cm higher than the platform, and the temperature of the water in the water tank was set to 22° C. Four icons of different shapes were respectively pasted in the four directions in the maze arm as a reference for spatial positioning. In the training experiment, the platform was 1 cm below the water surface, and then the mice were put into the two water entry points of the maze, and the mice were allowed to search for the platform for 60 seconds, and the mice staying on the platform for 10 seconds was used as the standard for stopping the experiment. If a mouse could not find the platform within 60 seconds, it was guided to the platform and let it stay on the platform for 10 seconds. Each mouse was tested twice a day, and two different positions were randomly selected for entering the water. The interval between two experiments for each mouse was at least 1 hour. The latency to find the platform (Latency to target) of a mouse in each experiment was recorded. The study training was performed for 6 consecutive days. On day 7, the platform was removed, and the platform test was performed. A mouse was placed in the water from the diagonal position of the platform, and it was allowed to search freely in the water maze for 60 seconds. The swimming time of the mouse in the target quadrant where the platform was located and the other three different quadrants (Time in quadrant) were recorded.

As shown in FIG. 1B, compared with WT, 5×FAD; Usp25$^{+/-}$ mice, 5×FAD mice exhibited significant learning deficits during training in the water maze. As shown in FIG. 1C and FIG. 1D, in the platform test, compared with WT mice, 5×FAD mice spent less time in the target quadrant; whereas after knockout of Usp25, the time of the 5×FAD; Usp25$^{+/-}$ mice staying in the target quadrant significantly increased, suggesting that knocking out Usp25 significantly improved spatial learning and memory for AD mice.

Fear conditioning test: During the first day of training, the mice were placed in a test box and acclimated to the environment for 2 minutes, and then a 60-dB noise stimulus (conditioned stimulus) was given to the mice for 30 seconds, and the mice were given a 0.05 mA electric shock stimulation (unconditioned stimulation) in the last 2 seconds of the noise stimulation (repeated three times, with an interval of 60 seconds each time). The mice were allowed to stay in the experimental chamber for 90 seconds after the final electric shock. On the morning of the first day after training, a Contextual test was performed. The mice were placed in the same test box for 5 minutes and the percentage of time to freeze (Freezing %) was recorded to measure contextual memory. On the afternoon of the first day after training, a Cued test was performed. The mice were placed in a test box (different walls, floors) that was different from that in the previous training environment, and the mice were first allowed to stay in the normal environment for 3 minutes, and then subjected to 60 decibel sound stimulation for 3 minutes. The percentage of freezing time (Freezing %) under the sound stimulus and in the normal environment, respectively.

As shown in FIG. 1E, compared with WT mice, 5×FAD mice exhibited severe contextual memory deficits; while after Usp25 was knockout, the contextual memory deficits of 5×FAD mice were significantly reversed; as shown in FIG. 1F, compared with WT mice, 5×FAD mice exhibited severe cued memory deficits, while the cued memory deficits in 5×FAD mice were significantly reversed after Usp25 knockout.

In addition, neuronal dendritic spine density was analyzed by Golgi staining, as shown in FIG. 1G. Compared with WT mice, neuronal dendritic spine density was significantly reduced in the brains of 5×FAD mice, while knockout of Usp25 significantly increased neuronal dendritic spine density in the brains of 5×FAD; $Usp25^{+/-}$ mice.

Figure 11:
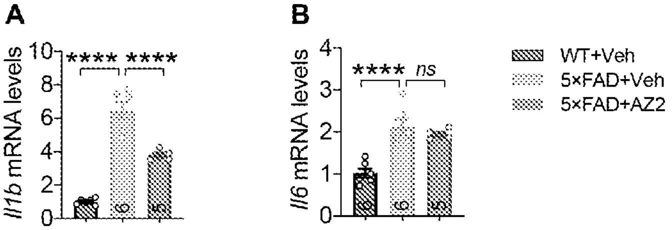
FIG. 11 shows the experiment that administration of AZ2 inhibits the inflammatory response in the brain of AD mice; wherein 6-month-old WT and 5×FAD male mice were administered with AZ2 or a control solvent (containing 1% Tween-80 and 0.5% CMC-Na aqueous solution, pH 3~4) by gavage at a dose of 20 mg/kg, respectively, and WT+Vehicle was the littermate control wild-type mice administered with the control solvent by gavage, 5×FAD+Vehicle was 5×FAD mice administered with the control solvent by gavage, and 5×FAD+AZ2 was 5×FAD mice experimental group administered with AZ2 by gavage. After continuous administration for 4 weeks, the mice were anesthetized with 5% chloral hydrate, and perfused with phosphate buffer. The brain tissue was isolated and then the hippocampus was isolated, RNAs were extracted by TRIzol and reverse-transcribed, and the transcription level of inflammation-related genes was detected by real-time fluorescence quantitative PCR. Figure (A) shows the transcription level of pro-inflammatory factor Il1b, and Figure (B) shows the transcription level of pro-inflammatory factor Il6. n (WT+Vehicle)=6, n (5×FAD+Vehicle)=6, and n (5×FAD+AZ2)=5. Data were statistically analyzed by one-way ANOVA. ns, no significant difference, P>0.05; ****P<0.0001.

Brain slice electrophysiological recordings were performed on 6-7 months old WT, $Usp25^{+/-}$, 5×FAD, 5×FAD; $Usp25^{+/-}$ mice. After a mouse was anesthetized, the brain tissue was quickly removed and placed in an ice-cold and oxygenated artificial cerebrospinal fluid (ACSF), and then transferred to an oscillatory microtome for coronal sectioning with a thickness of 400 μm. Brain slices were incubated in an oxygen-saturated ACSF at 32° C. for 1 hour and then transferred to room temperature for 1 hour. The recording electrodes were placed in the radiating layer of CA1 area of Schaffer collateral-commissural pathway, and the stimulating electrodes were placed in the CA3 area. The stimulus intensity was 30% of the maximum excitatory field excitatory postsynaptic potential (fEPSP). After stable fEPSP baseline was recorded for 20 minutes, long-term potentiation (LTP) was induced by high-frequency stimulation (HFS) (2 trains of 100 stimulation pulses, each with 30 s interval between stimulation trains) for a sustained period of 60 minutes. As shown in FIG. 11, compared with WT mice, LTP in Schaffer collateral-commissural pathway from hippocampal CA3 to CA1 in 5×FAD mice was significantly impaired, whereas after knockout of Usp25, LTP in 5×FAD; $Usp25^{+/-}$ mice was significantly enhanced, thus indicating that knockout of Usp25 can reverse synaptic dysfunction in AD mice.

Summing up, it is shown that knockout of Usp25 can reverse synaptic function and cognitive deficits in AD mice.

Example 39. Knockout of Usp25 Enhances Synaptic and Cognitive Function in DS Mice 6-7 months old WT, $Usp25^{+/-}$, Dp16, Dp165; $Usp25^{+/-}$ mice were subjected to behavioral tests related to learning and memory, including Y-maze, Morris water maze test and conditioned panic test. The mouse was touched and stroked three days before the experiment, once a day; the mouse tail was gently grabbed to pick up the mouse; and the mouse was kept on the hand for 30 seconds. On the day of the experiment, the mice for experiment were transferred to a preparation room, so that the mice could acclimate for 30 minutes. Behavioral experiments were performed daily between 9:00 a.m.-6:00 p.m. with a light intensity of 650 lux in the laboratory. Data acquisition and analysis were performed using Smart Video Tracking Software (Panlab, Harvard Apparatus).

Y-maze test was used to evaluate spontaneous spatial alternation behavior and working memory in mice. The mice were placed in the center of the Y-maze (length 30 cm, width 6 cm, height 15 cm), and then let the mice freely explore the maze for 5 mins. All four limbs of a mouse entering the maze arm was used as the standard for entering the maze arm, and the mouse entering different maze arms for three consecutive times was used as a correct autonomous alternate shuttle (Alternation).

Figure 2:
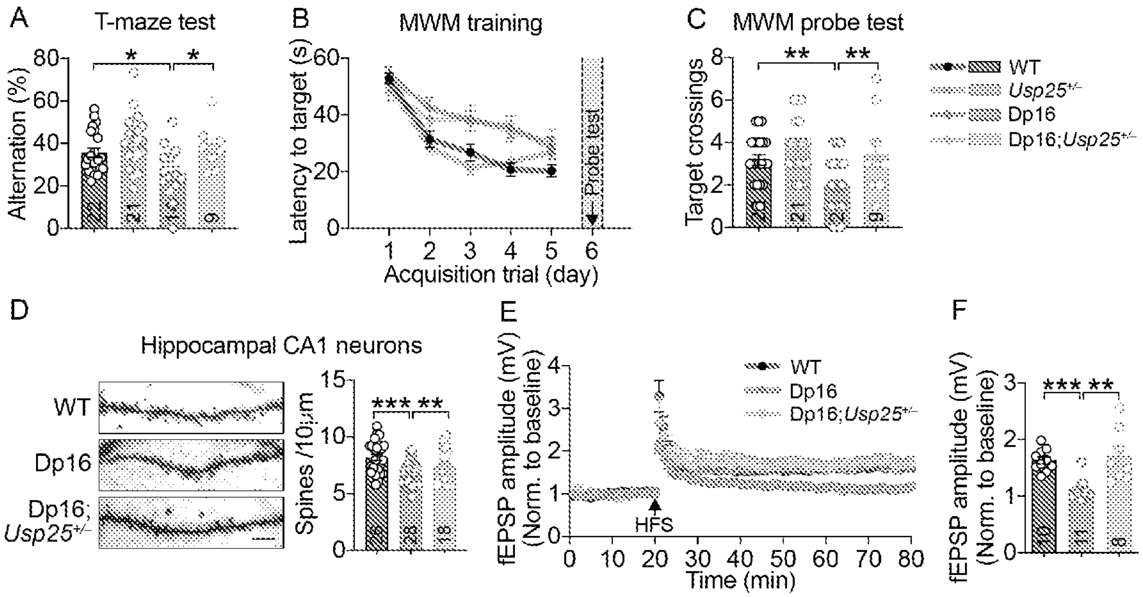
FIG. 2 is a schematic diagram showing that knockout of Usp25 enhances synaptic and cognitive function in DS mice; wherein (A-C) are the behavioral analysis results of 6-month old WT, $Usp25^{+/-}$, Dp16, Dp16; $Usp25^{+/-}$ mice. (A) Analysis results of the percentage of spontaneous alternations in the T-maze test (Alternation %). n=9~22 mice per group. (B) Latency to target of mice during Morris water maze (MWM) training. (C) The number of times of the mice crossed the quadrant of the platform during Morris water maze platform test (Target crossings). n=9~22 mice per group. (G) Representative graph of Golgi staining in hippocampus of 6-month-old mice and analysis results of dendritic spine density. Scale bar, 5 μm. n=18-28 dendrites per group. (E) LTP recording results in CA1 region of hippocampal slices of 6-month old mice. (I) Statistical analysis of fEPSP amplitudes in the last 10 min of LTP recordings. WT (n=5 mice/10 brain slices), 5×FAD (n=5 mice/11 brain slices), 5×FAD; $Usp25^{+/-}$ (n=5 mice/8 brain slices). Data in Figures (A, C) were statistically analyzed by one-way ANOVA, data in Figure (B) were statistically analyzed by repeated-measures ANOVA, and data in Figure (F) were statistically analyzed by 1Kruskal-Wallis test. *P<0.05; P<0.01; *P<0.001.

As shown in FIG. 2A, compared with WT mice, the percentage of autonomous alternate shuttles (Alternation %) in the Y-maze for Dp16 mice was significantly reduced, whereas after Usp25 knockout, the percentage of autonomous alternate shuttles for Dp16; $Usp^{25+/-}$ mice was significantly increased, suggesting that knocking out Usp25 could reverse working memory in DS mice.

The Morris water maze test was performed in a circular water tank (120 cm in diameter), the height of water filling in the water tank was preferably 1 cm higher than the platform, and the temperature of the water in the water tank was set to 22° C. Four icons of different shapes were respectively pasted in the four directions in the maze arm as a reference for spatial positioning. In the training experiment, the platform was 1 cm below the water surface, and then the mice were put into the two water entry points of the maze, and the mice were allowed to search for the platform for 60 seconds, and the mice staying on the platform for 10 seconds was used as the standard for stopping the experiment. If a mouse could not find the platform within 60 seconds, it was guided to the platform and let it stay on the platform for 10 seconds. Each mouse was tested twice a day, and two different positions were randomly selected for entering the water. The interval between two experiments for each mouse was at least 1 hour. The latency to find the platform (Latency to target) of a mouse in each experiment was recorded. The study training was performed for 5 consecutive days. On day 6, the platform was removed, and the platform test was performed. A mouse was placed in the water from the diagonal position of the platform, and it was allowed to search freely in the water maze for 60 seconds. The number of times for the mouse crossing the quadrant of the platform (Target crossings) were recorded.

As shown in FIG. 2B, compared with WT mice, Dp16 mice did not exhibit significant learning deficits during training in the water maze. As shown in FIG. 2C, in the platform test, compared with WT mice, the number of shuttles in the target quadrant of Dp16 mice was significantly reduced; whereas after knockout of Usp25, the number of shuttles in the target quadrant of Dp16; $Usp25^{+/-}$ mice was significantly increased, suggesting that knocking out Usp25 significantly improved spatial learning and memory for DS mice.

In addition, neuronal dendritic spine density was analyzed by Golgi staining, as shown in FIG. 2D. Compared with WT mice, neuronal dendritic spine density was significantly reduced in the brains of Dp16 mice, while knockout of Usp25 significantly increased neuronal dendritic spine density in the brains of Dp16; $Usp25^{+/-}$ mice.

Brain slice electrophysiological recordings were performed on 6-7 months old WT, Dp16, Dp16; $Usp25^{+/-}$ mice. After a mouse was anesthetized, the brain tissue was quickly removed and placed in an ice-cold and oxygenated artificial cerebrospinal fluid (ACSF), and then transferred to an oscillatory microtome for coronal sectioning with a thickness of 400 μm. Brain slices were incubated in an oxygen-saturated ACSF at 32° C. for 1 hour and then transferred to room temperature for 1 hour. The recording electrodes were placed in the radiating layer of CA1 area of Schaffer collateral-commissural pathway, and the stimulating electrodes were placed in the CA3 area. The stimulus intensity was 30% of the maximum excitatory field excitatory postsynaptic potential (fEPSP). After stable fEPSP baseline was recorded for 20 minutes, long-term potentiation (LTP) was induced by high-frequency stimulation (HFS) (2 trains of 100 stimulation pulses, each with 30 s interval between stimulation trains) for a sustained period of 60 minutes. As shown in FIGS. 2E-F, compared with WT mice, LTP in Schaffer collateral-commissural pathway from hippocampal CA3 to CA1 in Dp16 mice was significantly impaired, whereas after knockout of Usp25, LTP in Dp16; Usp25$^{+/-}$ mice was significantly enhanced, thus indicating that knockout of Usp25 can reverse synaptic dysfunction in DS mice.

Summing up, it is shown that knockout of Usp25 can reverse synaptic function and cognitive deficits in DS mice.

Example 40. Knockout of Usp25 Improves Mouse Microglial Homeostasis

Figure 3:
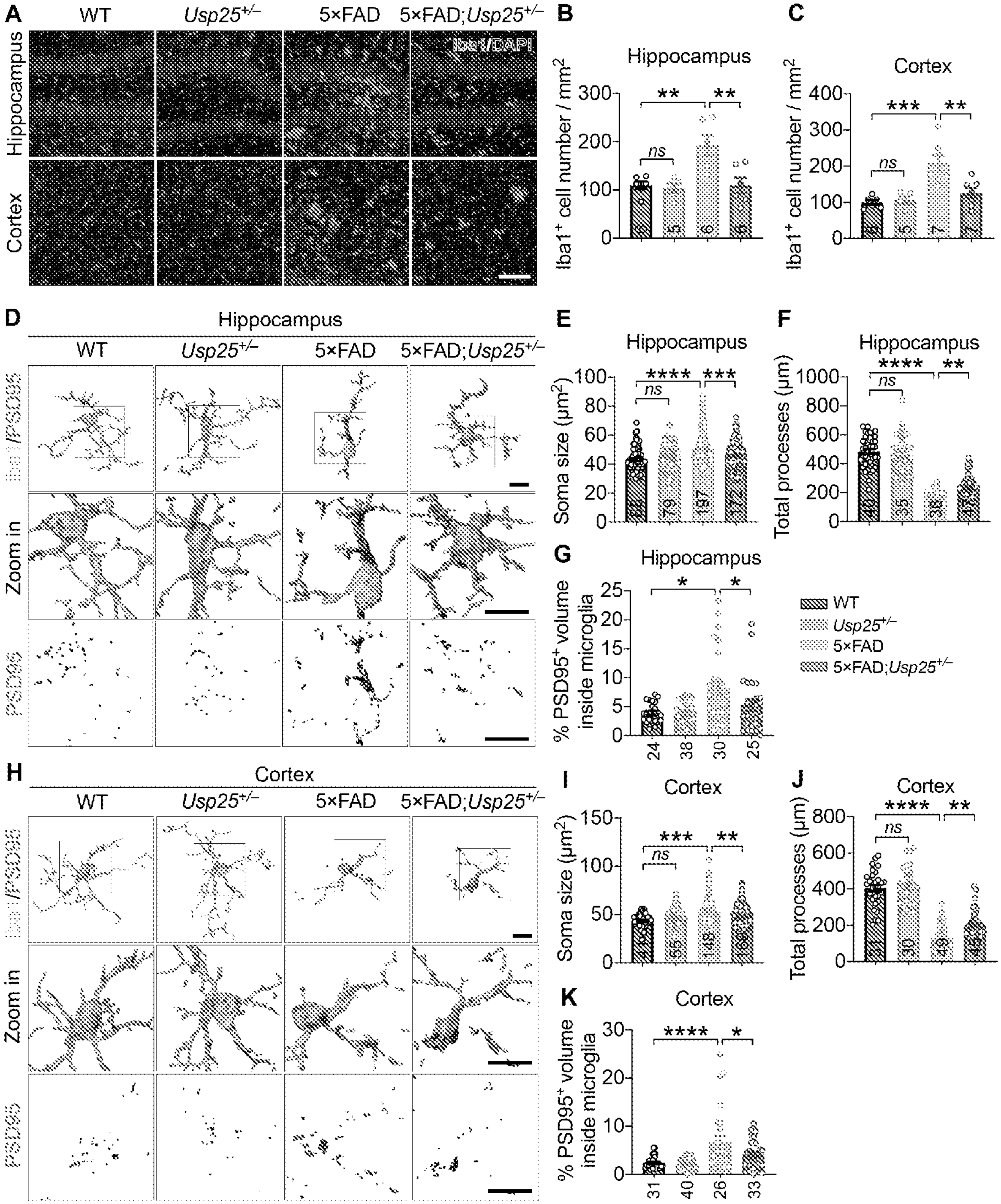
FIG. 3 is a schematic diagram of the improvement of mouse microglia homeostasis by knocking out Usp25; wherein (A-C) 6-7 month old WT, $Usp25^{+/-}$, 5×FAD, 5×FAD; $Usp25^{+/-}$ mice were anesthetized with 5% chloral hydrate, and perfused with phosphate buffer. The brain tissue was collected, fixed in 4% paraformaldehyde overnight, dehydrated in 25% and 30% sucrose solution, embedded by using OCT, sectioned, and immunofluorescence-stained to label the microglia marker protein Iba1 and the nuclear dye 4',6-diamidino-2-phenylindole (DAPI). Images were acquired by confocal fluorescence microscopy. Figure (A) shows the results of immunohistochemical staining of $Iba1^+$ microglia in the hippocampus and cerebral cortex. Figures (B, C) are the results of statistical analysis of the hippocampus (B) and the cerebral cortex (C), respectively. Scale bar, 100 μm. n=5-7 mice per group. (D) Representative diagram of the hippocampal tissue $Iba1^+$ microglia phagocytosing $PSD95^+$ synapse structure 3D-reconstructed by Imaris software. Scale bar, 10 μm. (E-G) Statistical analysis results of microglial cell body size (E), branch length (F), and microglia phagocytosing $PSD95^+$ synapse structure (G). n=3-6 mice, 24-197 microglia per group. (H) Representative image of cerebral cortex $Iba1^+$ microglia phagocytosing $PSD95^+$ synapse structure 3D-reconstructed by Imaris software. Scale bar, 10 μm. (I-K) Statistical analysis results of microglial cell body size (Soma size, I), branch length (Total processes, J), and microglia phagocytosing $PSD95^+$ synapse structure (K). n=3-6 mice, 26-169 microglia per group. Data in Figures (B, C, F, K) were statistically analyzed by one-way ANOVA, and data in Figures (E, G, I, J) were statistically analyzed by Kruskal-Wallis test. ns, no significant difference, P>0.05; *P<0.05; P<0.01; *P<0.001; ****P<0.001.

A 6-7 months old WT, Usp25$^{+/-}$, 5×FAD, 5×FAD; Usp25$^{+/-}$ mice was anesthetized with 5% chloral hydrate, then perfused with phosphate buffered saline, and the brain tissue was collected. The brain tissue was fixed with 4% paraformaldehyde overnight at 4° C. and dehydrated sequentially with 25% and 30% sucrose solutions. The brain tissue was then embedded by OCT, sliced, subjected to antigen-repair with sodium citrate buffer, blocked with 3% BSA buffer containing 0.2% Triton X-100, and subjected to immunofluorescence staining to label microglia marker protein Iba1 (Wako) and the nuclear dye 4',6-diamidino-2-phenylindole (DAPI) (sigma), respectively, followed by image acquisition with laser confocal fluorescence microscopy. As shown in FIGS. 3A-C, compared with WT mice, the number of microglia in the hippocampus and cerebral cortex of 5×FAD mice was significantly increased, while after Usp25 knockout, the microglia hyperplasia in the brain of 5×FAD mice was significantly reduced. The immunofluorescence staining images were 3D-reconstructed by Imaris software, and as shown in FIGS. 3D-F and FIGS. 3H-J, knockout of Usp25 significantly reduced the microglial cell body area in the hippocampus and cerebral cortex of 5×FAD mice and increased branch lengths of microglia, suggesting that microglial activation is inhibited. Furthermore, as shown in FIGS. 3D, 3G, 3H, and 3K, knockout of Usp25 significantly reduced phagocytosis of neuronal synapses by microglia in the brains of 5×FAD mice. Summing up, it was shown that knockout of Usp25 significantly inhibited microglial proliferation and activation as well as microglial-mediated synaptic phagocytosis in AD mouse brain.

Figure 4:
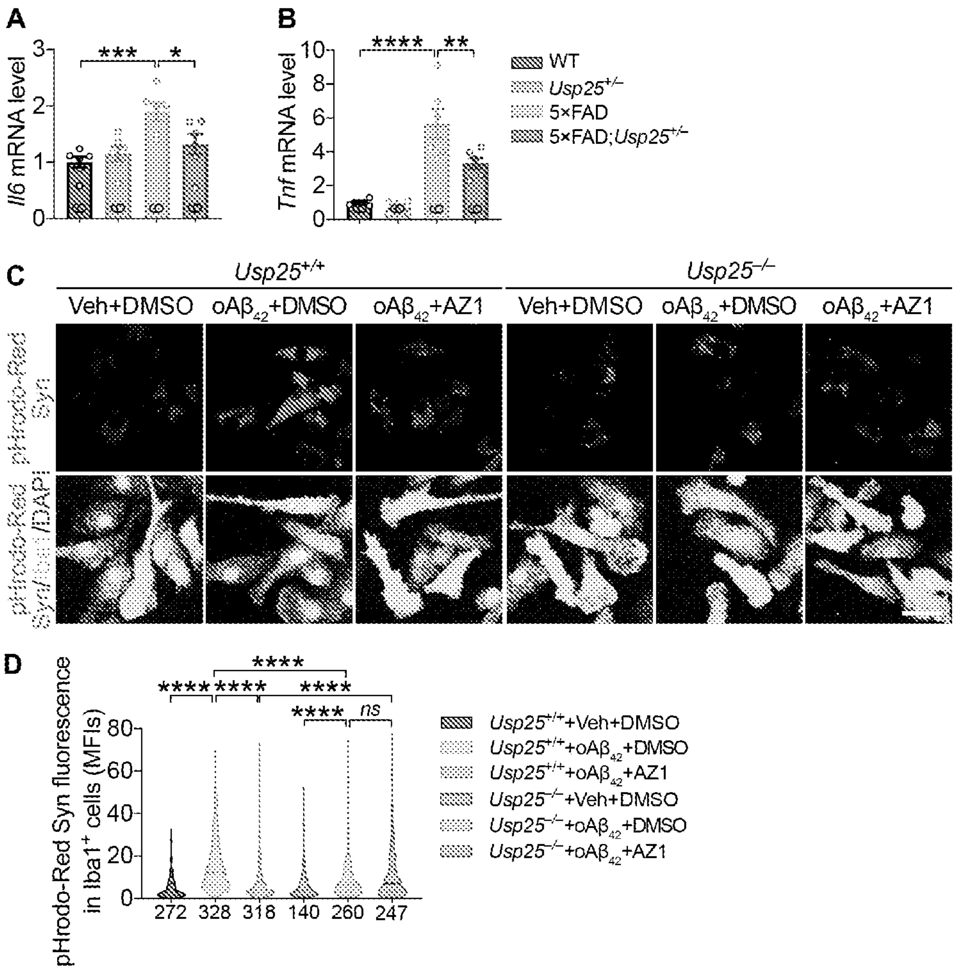
FIG. 4 is a schematic diagram showing that knockout of Usp25 inhibits the release of inflammatory factors and synaptic phagocytosis in mouse microglial cells; wherein (A, B) 10-month-old WT, $Usp25^{+/-}$, 5×FAD, 5×FAD; $Usp25^{+/-}$ mice hippocampal tissue, RNA was extracted by TRIzol and reverse-transcribed, and real-time fluorescent quantitative PCR was used to detect the transcription level of inflammation-related gene Il6 and Tnf. n=6. (C, D) $Usp25^{+/-}$, $Usp25^{+/-}$ mouse microglia and pHrodo-Red-labeled synaptosomes (Syn) were treated with 10 μM AZ1 or control solvent DMSO, and simultaneously 10 μM oAβ42 or control solvent Vehicle, respectively, and the fluorescence intensity of pHrodo-Red in $Iba1^+$ microglia was analyzed after 24 hours. Scale bar, 25 μm. n=140~328. Data in Figures (A, B) were statistically analyzed by one-way ANOVA, and data in Figures (D) were statistically analyzed by Kruskal-Wallis test. ns, no significant difference, P>0.05; *P<0.05; P<0.01; *P<0.001; ****P<0.001.

Example 41. Knockout of Usp25 Inhibits Inflammatory Cytokine Release and Synaptic Phagocytosis in Mouse Microglia 10-month-old WT, Usp25$^{+/-}$, 5×FAD, 5×FAD; Usp25$^{+/-}$ mice were anesthetized with 5% chloral hydrate, then perfused with phosphate buffered saline, and the brain tissue was taken and snap-frozen in liquid nitrogen, and then stored in a −80° C. refrigerator. RNAs were extracted by TRIzol (Thermo Fisher Scientific), then reverse-transcribed using the Rever Tra Ace qPCR RT Kit (TOYOBO), and real-time PCR was performed using FastStart Universal SYBR Green Master (Roche) to detect the transcription levels of inflammation-related genes Il6 and Tnf. As shown in FIG. 4A and FIG. 4B, compared with WT mice, the expression levels of pro-inflammatory factors Il6 and Tnf were significantly up-regulated in the brains of 5×FAD mice, while knockout of Usp25 significantly reduced the expression of Il6 and Tnf in the brains of 5×FAD mice, indicating that knockout of Usp25 can inhibit the inflammatory response in the brain of AD mouse.

Neonatal mouse microglia were isolated from Usp25$^{+/+}$, Usp25$^{+/-}$ mice on postnatal day 0, cultured in DMEM medium containing 25 ng/mL GM-CSF+10% fetal bovine serum for 10 days. The microglia were isolated by shaking at 220 rpm for 15 minutes. after 1 day of culture, the microglia and pHrodo-Red-labeled synaptosomes (Syn) were treated with 10 μM AZ1 or control solvent DMSO, and simultaneously with 10 μM oAβ42 or control solvent Vehicle, respectively. After 24 hours, cells were fixed in 4% paraformaldehyde, penetrated by 0.2% Triton X-100 solution, blocked by 3% BSA solution, and then the microglia marker protein Iba1 was labeled by immunofluorescence to analyze the fluorescence intensity of pHrodo-Red in Iba1$^{+}$ microglia. As shown in FIG. 4C and FIG. 4D, oAβ42 treatment can induce phagocytosis of pHrodo-Red-labeled synaptosomes by microglia, while knockout of Usp25 can reduce oAβ42-induced phagocytosis of synaptosomes by microglia. In addition, AZ1 treatment can also reduce oAβ42-induced phagocytosis of synaptosomes by microglia; and in Usp25$^{-/-}$ microglia, AZ1 treatment could no longer reduce phagocytosis of synaptosomes by microglia, showing that inhibitory effects of AZ1 on the phagocytosis of synapses by microglial was dependent on USP25.

Example 42. Experiment of Penetration Through the Blood-Brain Barrier for AZ1

After AZ1 was administered to ICR mice by gavage, brain tissue and blood samples were collected at different time points to study blood-brain barrier properties of AZ1 in ICR mice.

Preparation of AZ1 solution for administration by gavage: about 4 mg of AZ1 was accurately weighed into a glass bottle, an appropriate volume of 0.5% CMC-Na aqueous solution (1% Tween-80) was added, and pH was adjusted to 3-4 with 1 M HCl. After vortexing, ultrasonication was carried out to dissolve AZ1, and a final concentration of 1 mg/mL was obtained.

9 male ICR mice of 27.8-33.3 g were taken and divided into three groups (0.5, 2, and 8 hours at different administration times), and the experimental animals were administered by gavage at a dose of 10 mg/kg. Then, the mice were anesthetized with carbon dioxide at 0.5, 2, and 8 hours after administration, blood was collected from the heart (about 0.2 mL) and the mice were sacrificed. Whole blood was placed in a test tube containing anticoagulant EDTA-K2, stored on wet ice, and centrifuged (1500~1600 g) for 10 minutes within 1 hour to separate plasma. After the ICR mice were sacrificed, the brain tissue was excised, washed with ice physiological saline, and then weighed after dehydration, and 20% methanol-water was added at a weight-volume ratio of 1:5 (tissue:homogenate) for homogenization. Plasma and brain tissue homogenates were stored in a freezer at −40 to −20° C. for sample analysis.

The concentrations of AZ1 in plasma and brain of ICR mice after administration were determined by LC-MS/MS (API 4000: LC-MS-MS-010) method by Suzhou Shengsu New Drug Development Co., Ltd. As shown in Table 1, at 0.5, 2, and 8 hours after administration, the level of AZ1 in the plasma decreased from 68.8±11.9 ng/mL to 24.8±5.0 ng/mL and 3.9±1.1 ng/mL, and the level of AZ1 in the brain decreased from 559.2±138.3 ng/g to 388.2±49.0 ng/g and 80.8±1.2 ng/g. Summing up, it is shown that AZ1 can penetrate the blood-brain barrier in mice.

TABLE 1

| Permeability of AZ1 in the brain of mice after administration by gavage (10 mg/kg) | | | |
|---|---|---|---|
| Time Point (h) | Brain Conc. (ng · $g^{-1}$) | Plasma Conc. (ng · $mL^{-1}$) | Brain/Plasma Conc. ratio |
| 0.5 | 559.00 ± 79.98 | 68.77 ± 6.89 | 8.17 ± 1.00 |
| 2 | 388.30 ± 28.11 | 24.77 ± 2.90 | 15.90 ± 1.07 |
| 8 | 80.80 ± 0.72 | 3.87 ± 0.61 | 21.80 ± 2.87 |

Figure 5:
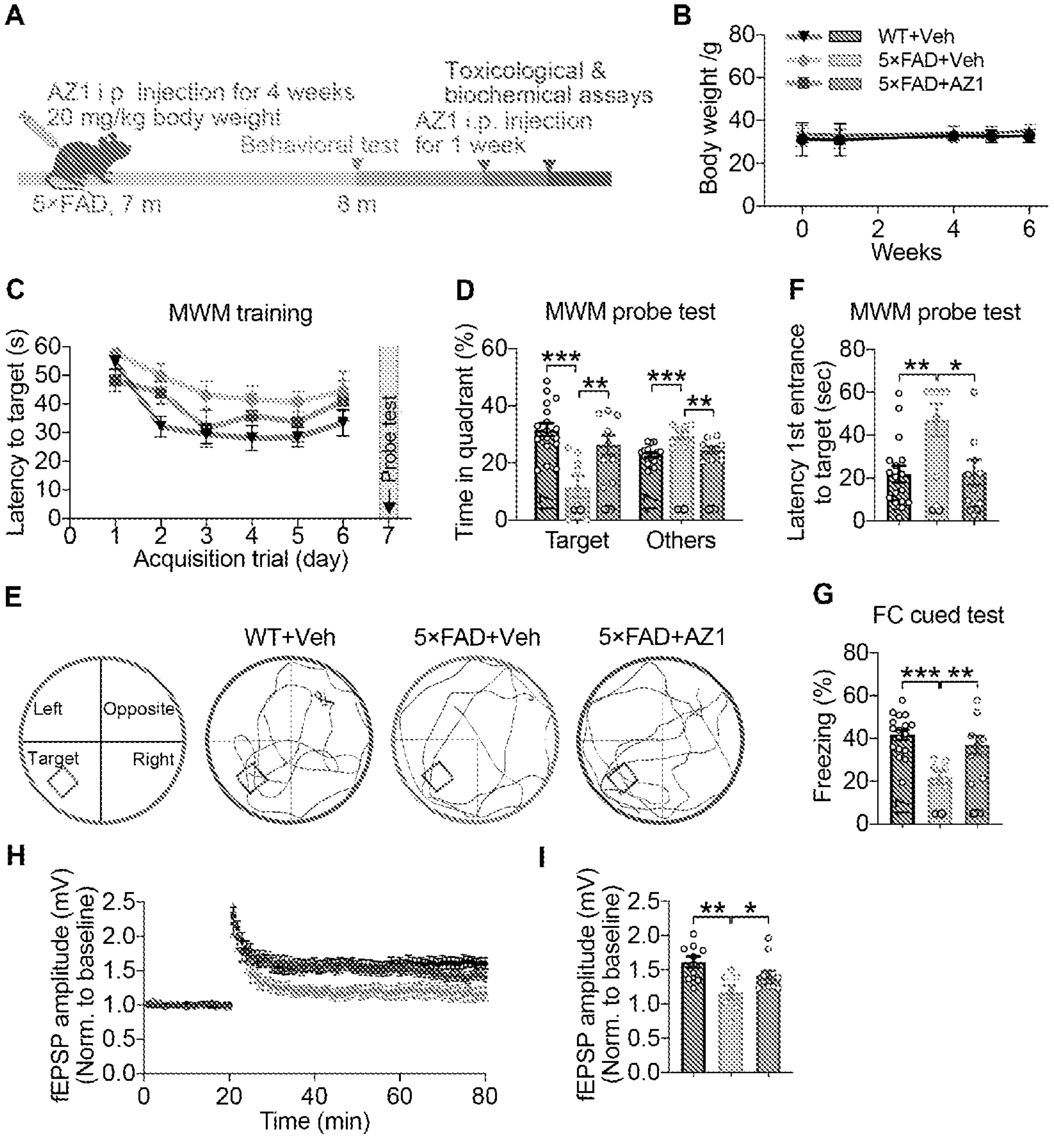
FIG. 5 is a schematic diagram showing that administration of AZ1 reverses synaptic and cognitive deficits in AD mice; wherein (A) 7-month-old WT and 5×FAD male mice were intraperitoneally injected with AZ1 or control solvent (5% DMSO+95% corn oil) at a dose of 20 mg/kg, respectively, and behavioral tests related to learning and memory were performed after continuous administration for 4 weeks. (B) Changes in the body weight of mice before and after administration of AZ1. n(WT+Vehicle)=16, n(5×FAD+Vehicle)=8, n(5×FAD+AZ1)=9. (C) Latency to target for mice to find the hidden platform in the Morris water maze hidden platform training (6 days) 1 month after administration. (D) Time in quadrant % of mice in the platform quadrant and other quadrants in the Morris water maze platform test (day 7). (E) Schematic diagram of the swimming trajectories of mice in the Morris water maze platform test. (F) Latency time for mice to reach the platform area for the first time in Morris water maze platform test (Latency $1^{st}$ entrance). (G) Percentage of freezing time (Freezing %) in mice in a Fear conditioned cue-related memory test. n(WT+Vehicle)=17, n(5×FAD+Vehicle)=8, n(5×FAD+AZ1)=9. (H, I) 5-month-old WT and 5×FAD male mice were intraperitoneally injected with AZ1 or control vehicle (5% DMSO+95% corn oil) at a dose of 20 mg/kg, respectively, wherein WT+Vehicle was the littermate control Wild-type mice intraperitoneally injected with control solvent, 5×FAD+Vehicle was 5×FAD mice intraperitoneally injected with control solvent, and 5×FAD+AZ1 was 5×FAD mice experimental group intraperitoneally injected with AZ1, and electrophysiological recording of mouse brain slices was performed after 4 weeks of continuous administration. Figure (H) shows the result of LTP recording in the CA1 region of the mouse hippocampus slice. Figure (I) shows the statistical results of the last 10 minutes of LTP. n (WT+Vehicle)=5 mice/10 brain slices, n (5×FAD+Vehicle)=4 mice/7 brain slices, n (5×FAD+AZ1)=7 mice/12 brain slices. Data in Figures (B, C) were statistically analyzed by repeated-measures ANOVA, and data in Figures (D, F, G, I) were statistically analyzed by one-way ANOVA. ns, no significant difference, $P>0.05$; $*P<0.05$; $P<0.01$; $*P<0.001$.

Example 43. Administration of AZ1 Reverses Synaptic and Cognitive Deficits in AD Mice 7-month-old WT and 5×FAD male mice were intraperitoneally injected with AZ1 or control solvent (5% DMSO+95% corn oil) at a dose of 20 mg/kg, wherein WT+Vehicle was the littermate control wild-type mice injected with the control solvent, 5×FAD+Vehicle was 5×FAD mice intraperitoneally injected with the control solvent, and 5×FAD+AZ1 was 5×FAD mice experimental group intraperitoneally injected with AZ1 (FIG. 5A). As shown in FIG. 5B, the administration of AZ1 did not affect the body weight of mice.

After 4 weeks of continuous administration, behavioral tests related to learning and memory, including Morris water maze test and Fear conditioning test, were performed. The mouse was touched and stroked three days before the experiment, once a day; the mouse tail was gently grabbed to pick up the mouse; and the mouse was kept on the hand for 30 seconds. On the day of the experiment, the mice for experiment were transferred to a preparation room, so that the mice could acclimate for 30 minutes. Behavioral experiments were performed daily between 9:00 a.m.-6:00 p.m. with a light intensity of 650 lux in the laboratory. Data acquisition and analysis were performed using Smart Video Tracking Software (Panlab, Harvard Apparatus).

The Morris water maze test was performed in a circular water tank (120 cm in diameter), the height of water filling in the water tank was preferably 1 cm higher than the platform, and the temperature of the water in the water tank was set to 22° C. Four icons of different shapes were respectively pasted in the four directions in the maze arm as a reference for spatial positioning. In the training experiment, the platform was 1 cm below the water surface, and then the mice were put into the two water entry points of the maze, and the mice were allowed to search for the platform for 60 seconds, and the mice staying on the platform for 10 seconds was used as the standard for stopping the experiment. If a mouse could not find the platform within 60 seconds, it was guided to the platform and let it stay on the platform for 10 seconds. Each mouse was tested twice a day, and two different positions were randomly selected for entering the water. The interval between two experiments for each mouse was at least 1 hour. The latency to find the platform (Latency to target) of a mouse in each experiment was recorded. The study training was performed for 6 consecutive days. On day 7, the platform was removed, and the platform test was performed. A mouse was placed in the water from the diagonal position of the platform, and it was allowed to search freely in the water maze for 60 seconds. The swimming time of the mouse in the target quadrant where the platform was located and the other three different quadrants (Time in quadrant) were recorded.

As shown in FIG. 5C, compared with WT+Vehicle mice, 5×FAD+Vehicle mice did not exhibited significant learning deficits during training in the water maze. As shown in FIG. 5D and FIG. 5E, in the platform test, compared with WT+Vehicle mice, 5×FAD+Vehicle mice spent less time in the target quadrant; whereas the administration of AZ1 significantly increased the time of the 5×FAD mice staying in the target quadrant. Furthermore, as shown in FIG. 5F, the administration of AZ1 significantly reduced the latency to target for the 5×FAD mice to reach the platform position for the first time, suggesting that the administration of AZ1 significantly improved spatial learning and memory for AD mice.

Fear conditioning test: During the first day of training, the mice were placed in a test box and acclimated to the environment for 2 minutes, and then a 60-dB noise stimulus (conditioned stimulus) was given to the mice for 30 seconds, and the mice were given a 0.05 mA electric shock stimulation (unconditioned stimulation) in the last 2 seconds of the noise stimulation (repeated three times, with an interval of 60 seconds each time). The mice were allowed to stay in the experimental chamber for 90 seconds after the final electric shock. On the first day after training, a Cued test was performed. The mice were placed in a test box (different walls, floors) that was different from that in the previous training environment, and the mice were first allowed to stay in the normal environment for 3 minutes, and then subjected to 60 decibel sound stimulation for 3 minutes. The percentage of freezing time (Freezing %) under the sound stimulus and in the normal environment, respectively.

As shown in FIG. 5G, compared with WT+Vehicle mice, 5×FAD+Vehicle mice exhibited severe cued memory deficits, while the cued memory deficits in 5×FAD mice were significantly reversed after the administration of AZ1.

Summing up, it was showed that the administration of AZ1 can reverse the cognitive deficits in AD mice.

5-month-old WT and 5×FAD male mice were intraperitoneally injected with AZ1 or control solvent (5% DMSO+95% corn oil) at a dose of 20 mg/kg, wherein WT+Vehicle was the littermate control wild-type mice injected with the control solvent, 5×FAD+Vehicle was 5×FAD mice intraperitoneally injected with the control solvent, and 5×FAD+AZ1 was 5×FAD mice experimental group intraperitoneally injected with AZ1.

After 4 weeks of continuous administration, Brain slice electrophysiological recordings were performed on the mice. After a mouse was anesthetized, the brain tissue was quickly removed and placed in an ice-cold and oxygenated artificial cerebrospinal fluid (ACSF), and then transferred to an oscillatory microtome for coronal sectioning with a thickness of 400 μm. Brain slices were incubated in an oxygen-saturated ACSF at 32° C. for 1 hour and then transferred to room temperature for 1 hour. The recording electrodes were placed in the radiating layer of CA1 area of Schaffer collateral-commissural pathway, and the stimulating electrodes were placed in the CA3 area. The stimulus intensity was 30% of the maximum excitatory field excitatory postsynaptic potential (fEPSP). After stable fEPSP baseline was recorded for 20 minutes, long-term potentiation (LTP) was induced by high-frequency stimulation (HFS) (2 trains of 100 stimulation pulses, each with 30 s interval between stimulation trains) for a sustained period of 60 minutes. As shown in FIGS. 5H and SI, compared with WT+Vehicle mice, LTP in Schaffer collateral-commissural pathway from hippocampal CA3 to CA1 in 5×FAD+Vehicle mice was significantly impaired, whereas the administration of AZ1 significantly enhanced LTP in 5×FAD mice, thus indicating that the administration of AZ1 can reverse synaptic dysfunction in AD mice.

Figure 6:
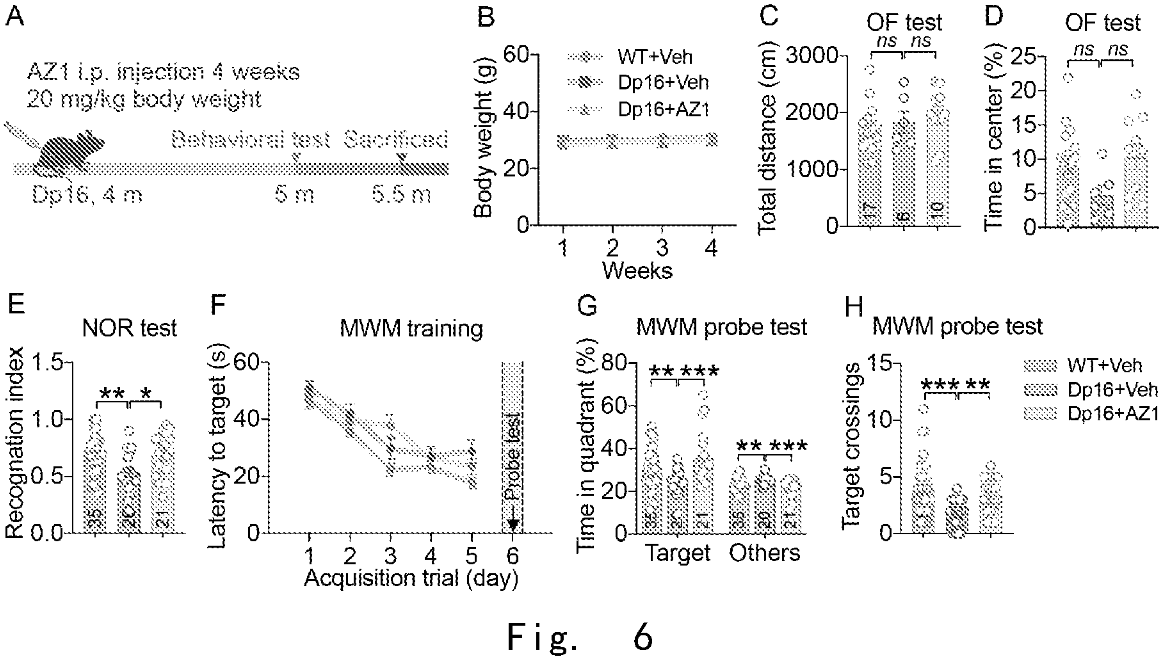
FIG. 6 is the schematic diagram showing that the administration of AZ1 reverses the cognitive function deficit of DS mice; wherein (A) 5-month-old WT and Dp16 male mice were intraperitoneally injected with AZ1 or a control solvent (5% DMSO+95% corn oil) at a dose of 20 mg/kg, respectively, and behavioral tests related to learning and memory were performed after continuous administration for 4 weeks. (B) Changes in the body weight of mice before and after administration of AZ1. n=20~35 mice/group. (C) Total distance of mice in Open field test (OF test). (D) Percentage of mice's exercise time in the middle area in the open field test (Time in center %), n=6-17 mice per group. (E) Recognition index of mice recognizing novel objects in Novel object recognition test (NOR test). (F) Latency to target for mice to find the hidden platform in the Morris water maze hidden platform training (5 days). (G) Time in quadrant % of mice in the platform quadrant and other quadrants in the Morris water maze platform test (day 6). (H) The number of times of the mice crossed the quadrant of the platform during Morris water maze platform test (Target crossings). n=20~35 mice per group. Data in Figures (B, F) were statistically analyzed by repeated-measures ANOVA, data in Figures (C, D, G, H) were statistically analyzed by Kruskal-Wallis test, and data in Figure (E) were statistically analyzed by one-way ANOVA. ns, no significant difference, $P>0.05$; $*P<0.05$; $P<0.01$; $*P<0.001$.

Example 44. Administration of AZ1 Reverses Cognitive Deficits in DS Mice 5-month-old WT and Dp16 male mice were intraperitoneally injected with AZ1 or control solvent (5% DMSO+95% corn oil) at a dose of 20 mg/kg, wherein WT+Vehicle was the littermate control wild-type mice injected with the control solvent, Dp16+Vehicle was Dp16 mice intraperitoneally injected with the control solvent, and Dp16+AZ1 was Dp16 mice experimental group intraperitoneally injected with AZ1 (FIG. 6A). As shown in FIG. 6B, the administration of AZ1 did not affect the body weight of mice.

After 4 weeks of continuous administration, behavioral tests, including Open field test, T-maze test, novel object recognition and Morris water maze test, were performed. The mouse was touched and stroked three days before the experiment, once a day; the mouse tail was gently grabbed to pick up the mouse; and the mouse was kept on the hand for 30 seconds. On the day of the experiment, the mice for experiment were transferred to a preparation room, so that the mice could acclimate for 30 minutes. Behavioral experiments were performed daily between 9:00 a.m.-6:00 p.m. with a light intensity of 650 lux in the laboratory. Data acquisition and analysis were performed using Smart Video Tracking Software (Panlab, Harvard Apparatus).

Open field test was used to evaluate the motor ability and anxiety-like mood of mice. The mice were placed in the center of the open field, and then the mice were allowed to explore freely in the maze for 10 minutes, and the total distance and time in the center of the open field were recorded.

As shown in FIGS. 6C and 6D, the administration of AZ1 did not affect the movement distance of mice in the open field and the time in the center of the open field, indicating that the administration of AZ1 exhibited no significant toxicological effects on the mice.

Novel object recognition test is based on the innate tendency of mice to explore novel objects. The process of exploring novel objects reflects the process of learning, recognition and memory of the mice, and can be used to evaluate the working memory of the mice. On the first day, the mice were allowed to explore freely in a separate open field for 5 min to become familiar with the environment; on the second day, two objects A and B were placed in the open field, and the mice were allowed to explore freely for 10 min; and on the third day, one of the objects A was replaced with a new object C, and the mice were allowed to explore freely for 10 min. The number of times for the mice to explore B and C was recorded, Recognition index=C/(B+C).

As shown in FIG. 6E, compared with WT+Vehicle mice, Dp16+Vehicle mice significantly reduced the number of exploration of novel objects, while the administration of AZ1 can significantly increase the exploration of novel objects for Dp16 mice, indicating that the administration of AZ1 can improve working memory in Dp16 mice.

The Morris water maze test was performed in a circular water tank (120 cm in diameter), the height of water filling in the water tank was preferably 1 cm higher than the platform, and the temperature of the water in the water tank was set to 22° C. Four icons of different shapes were respectively pasted in the four directions in the maze arm as a reference for spatial positioning. In the training experiment, the platform was 1 cm below the water surface, and then the mice were put into the two water entry points of the maze, and the mice were allowed to search for the platform for 60 seconds, and the mice staying on the platform for 10 seconds was used as the standard for stopping the experiment. If a mouse could not find the platform within 60 seconds, it was guided to the platform and let it stay on the platform for 10 seconds. Each mouse was tested twice a day, and two different positions were randomly selected for entering the water. The interval between two experiments for each mouse was at least 1 hour. The latency to find the platform (Latency to target) of a mouse in each experiment was recorded. The study training was performed for 5 consecutive days. On day 6, the platform was removed, and the platform test was performed. A mouse was placed in the water from the diagonal position of the platform, and it was allowed to search freely in the water maze for 60 seconds. The swimming time of the mouse in the target quadrant where the platform was located and the other three different quadrants (Time in quadrant), as well as the number of times for the mice crossing the quadrant of the platform (Target crossings) were recorded.

As shown in FIG. 6F, compared with WT+Vehicle mice, Dp16+Vehicle mice did not exhibit significant learning deficits during training in the water maze. As shown in FIG. 6G, in the platform test, compared with WT+Vehicle mice, Dp16+Vehicle mice spent less time in the target quadrant; whereas the administration of AZ1 significantly increased the time of Dp16 mice staying in the target quadrant. Furthermore, the administration of AZ1 significantly increased the number of shuttles in the target quadrant of Dp16 mice, suggesting that the administration of AZ1 significantly improved spatial learning and memory for DS mice.

Example 45. Administration of AZ1 Results in No Significant Toxicological Effects 5-month-old WT and 5×FAD male mice were intraperitoneally injected with AZ1 or control solvent (5% DMSO+95% corn oil) at a dose of 20 mg/kg, wherein WT+Vehicle was the littermate control wild-type mice injected with the control solvent, 5×FAD+Vehicle was 5×FAD mice intraperitoneally injected with the control solvent, and 5×FAD+AZ1 was 5×FAD mice experimental group intraperitoneally injected with AZ1.

Figure 7:
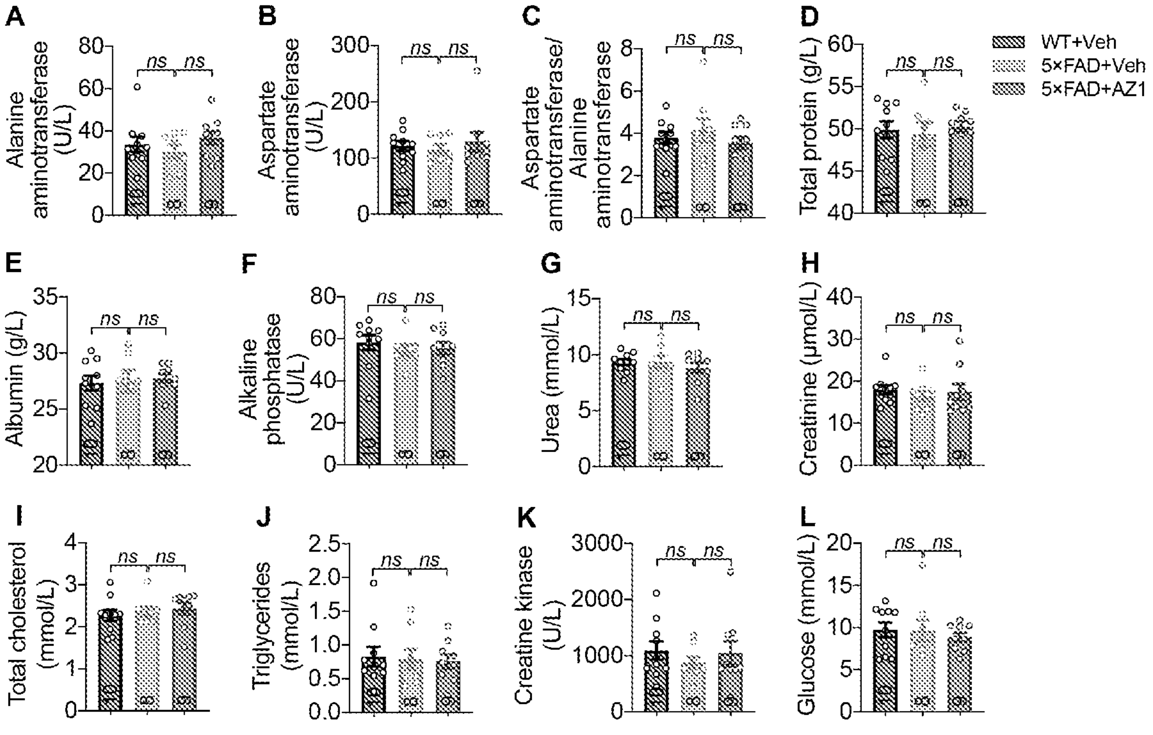
FIG. 7 is a schematic diagram of toxicological effects of administration of AZ1 on mice; wherein 7-month-old WT and 5×FAD male mice were intraperitoneally injected with AZ1 or control solvent (5% DMSO+95% corn oil) at a dose of 20 mg/kg, respectively, WT+Vehicle was the littermate control wild-type mice intraperitoneally injected with the control solvent, 5×FAD+Vehicle was 5×FAD mice intraperitoneally injected with the control solvent, and 5×FAD+AZ1 was 5×FAD mice experimental group intraperitoneally injected with AZ1. Behavioral tests related to learning and memory were performed after continuous administration for 4 weeks. After the test, the mice were administered for another 1 week, then the mice were anesthetized with 5% chloral hydrate, and the blood was collected by removing the eyeballs. The blood was kept at 4° C. for more than 30 minutes, centrifuged at 3000 rpm, 4° C. for 5 minutes, and serum was collected for blood biochemical detection, wherein liver functions include (A) alanine aminotransferase, (B) aspartate aminotransferase, (C) aspartate aminotransferase/alanine aminotransferase ratio, (D) total protein, (E) albumin, (F) alkaline phosphatase; renal function includes (G) urea, (H) creatinine; and blood lipids includes (I) total cholesterol, (J) triglyceride; myocardial enzyme spectrum (K) creatine kinase; Blood glucose (L) glucose. n (WT+Vehicle)=10, n (5×FAD+Vehicle)=8, and n (5×FAD+AZ1)=8. The data were statistically analyzed by Kruskal-Wallis test. ns, no significant difference, $P>0.05$.

After 4 weeks of continuous administration, a learning-related behavioral test was performed. After the test, AZ1 was administered for another week. Then the mice were anesthetized with 5% chloral hydrate, the eyeball was removed and the blood was collected, kept at 4° C. for more than 30 minutes, and centrifuged at 3000 rpm and 4° C. for 5 minutes, so that the serum was collected. And then the serum was passed through an automatic biochemical analyzer (Minray Company, BS-240vet) for blood biochemical testing. Liver function indicators include ALT (alanine aminotransferase), AST (aspartate aminotransferase), ALP (alkaline phosphatase), TP (total protein), ALB (albumin); renal function indicators include Urea (urea), CREA-S (creatinine); and blood lipids includes TC (total cholesterol), TG (triglyceride), myocardial enzyme spectrum CK (creatine kinase), blood glucose Glu-G. As shown in FIG. 7, after the administration of AZ1, mice did not show obvious abnormality in liver function, renal function, myocardial function, blood glucose and blood lipids, suggesting that AZ1 has no significant toxicological effects on mice.

Example 46. Administration of AZ1 Inhibits Brain Neuroinflammation in AD Mice 5-month-old WT and 5×FAD male mice were intraperitoneally injected with AZ1 or control solvent (5% DMSO+

95% corn oil) at a dose of 20 mg/kg, wherein WT+Vehicle was the littermate control wild-type mice injected with the control solvent, 5×FAD+Vehicle was 5×FAD mice intraperitoneally injected with the control solvent, and 5×FAD+AZ1 was 5×FAD mice experimental group intraperitoneally injected with AZ1.

Figure 8:
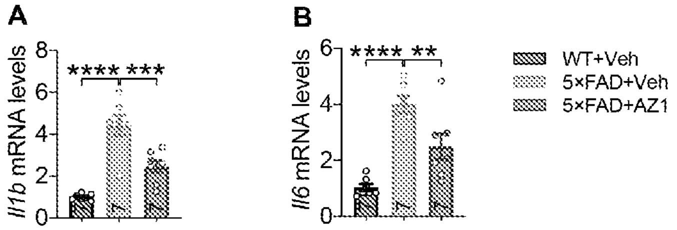
FIG. 8 shows the experiment that the administration of AZ1 inhibits the inflammatory response in AD mouse brain; wherein 7-month-old WT and 5×FAD male mice were intraperitoneally injected with AZ1 or control solvent (5% DMSO+95% corn oil) at a dose of 20 mg/kg, respectively, WT+Vehicle was the littermate control wild-type mice intraperitoneally injected with the control solvent, 5×FAD+Vehicle was 5×FAD mice intraperitoneally injected with the control solvent, and 5×FAD+AZ1 was 5×FAD mice experimental group intraperitoneally injected with AZ1. Behavioral tests related to learning and memory were performed after continuous administration for 4 weeks. After the test, the mice were administered for another 1 week, then the mice were anesthetized with 5% chloral hydrate, and perfused with phosphate buffer. The hippocampus was separated from the brain tissue. RNAs were extracted by TRIzol, and after reverse transcription, real-time fluorescence quantitative PCR was used to detect the transcription level of inflammation-related genes. Figure (A) shows the transcription level of pro-inflammatory factor Il1b, and Figure (B) shows the transcription level of pro-inflammatory factor Il6. n (WT+Vehicle)=7, n (5×FAD+Vehicle)=7, and n (5×FAD+AZ1)=7. The data were statistically analyzed by One-way ANOVA. $P<0.01$; $**P<0.0001$.
Figure 9:
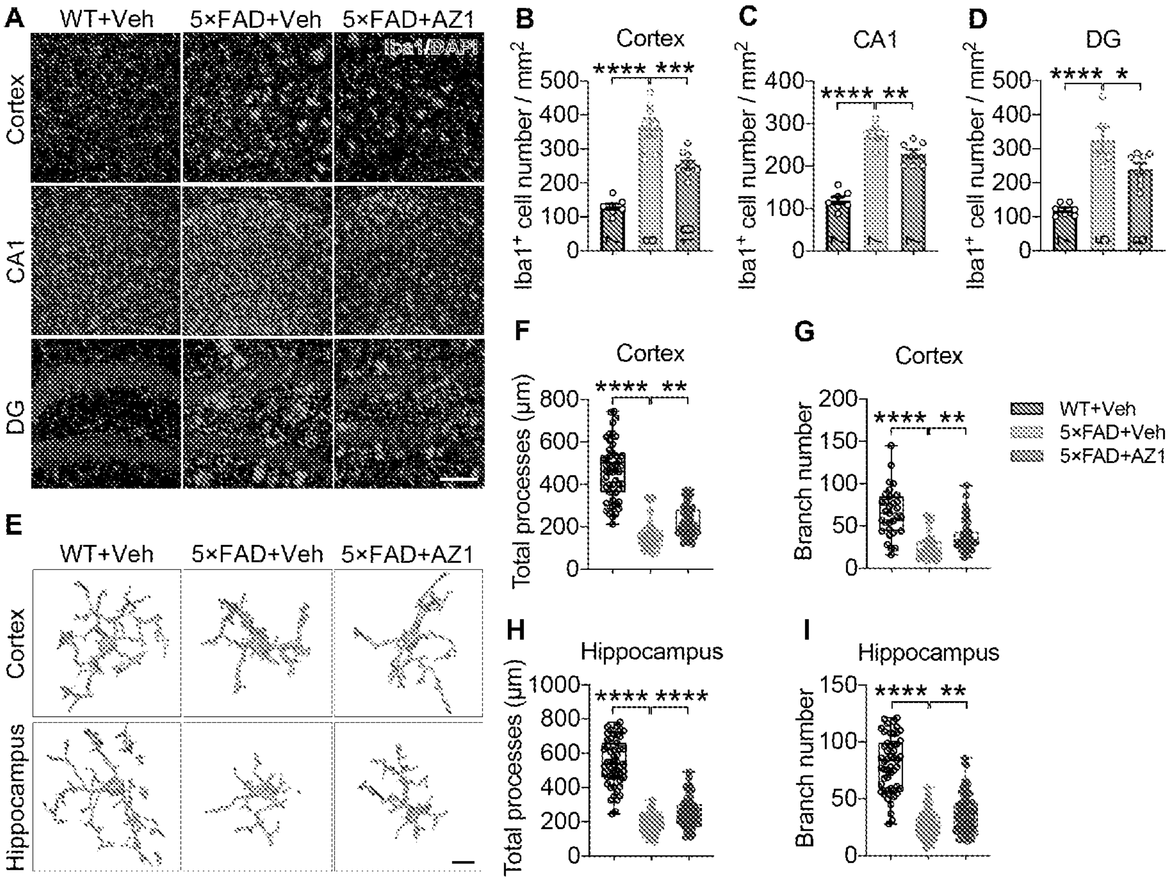
FIG. 9 shows the experiment that administration of AZ1 inhibits the proliferation and activation of microglia in the brain of AD mice; wherein 7-month-old WT and 5×FAD male mice were intraperitoneally injected with AZ1 or control solvent (5% DMSO+9% corn oil) at a dose of 20 mg/kg, respectively, WT+Vehicle was the littermate control wild-type mice intraperitoneally injected with the control solvent, 5×FAD+Vehicle was 5×FAD mice intraperitoneally injected with the control solvent, and 5×FAD+AZ1 was 5×FAD mice experimental group intraperitoneally injected with AZ1. Behavioral tests related to learning and memory were performed after continuous administration for 4 weeks. After the test, the mice were administered for another 1 week, then the mice were anesthetized with 5% chloral hydrate, and perfused with phosphate buffer. The brain tissue was taken, fixed in 4% paraformaldehyde overnight, dehydrated by 25% and 30% sucrose solution, embedded in brain tissue using OCT, sliced, and subjected to immunofluorescence staining to label microglia marker protein Iba1 and nuclear dye 4',6-diamidino-2-phenylindole (DAPI), and images were collected by confocal fluorescence microscopy. Figure (A) shows the result of immunohistochemical staining of $Iba1^+$ microglia in cerebral cortex, hippocampal CA1 area and DG area. Scale bar, 100 μm. Figures (B-D) show the results of statistical analysis of the cerebral cortex (B), hippocampal CA1 area (C) and DG area (D), respectively. n=7~10 mice per group. (E) shows representative images of $Iba1^+$ microglia in hippocampus 3D-reconstructed by Imaris software. Scale bar, 10 μm. (F-I) Statistical analysis results of microglial branch length (Total processes, F, H) and branch number (Branch number, G, I). n=5 mice per group, 31~76 microglia. Data in Figures (B, D, F, H) were statistically analyzed by one-way ANOVA, and data in Figures (G, I) were statistically analyzed by Kruskal-Wallis test. $*P<0.05$; $P<0.01$; $*P<0.001$; $****P<0.0001$.

After 4 weeks of continuous administration, a behavioral tests related to learning and memory was performed. After the test, AZ1 was administered for another week. Then the mice were anesthetized with 5% chloral hydrate, perfused with phosphate buffered saline, and the brain tissue was taken and snap-frozen in liquid nitrogen, and then stored in a −80° C. refrigerator. RNAs were extracted by TRIzol (Thermo Fisher Scientific), then reverse-transcribed using Rever Tra Ace qPCR RT Kit (TOYOBO), and real-time fluorescence quantification PCR was performed using FastStart Universal SYBR Green Master (Roche) to detect the transcription levels of inflammation-related genes Il1b and Il6. As shown in FIG. 8, compared with WT+Vehicle mice, the expression levels of pro-inflammatory factors Il1b and Il6 were significantly up-regulated in the brains of 5×FAD+Vehicle mice, while the administration of AZ1 significantly reduced the expression of Il1b and Il6 in the brains of 5×FAD mice, indicating that the administration of AZ1 can inhibit the inflammatory response in the brain of AD mouse.

Example 47. Administration of AZ1 Inhibits Microglial Proliferation and Activation in the Brain of AD Mouse 7-month-old WT and 5×FAD male mice were intraperitoneally injected with AZ1 or control solvent (5% DMSO+95% corn oil) at a dose of 20 mg/kg, wherein WT+Vehicle was the littermate control wild-type mice injected with the control solvent, 5×FAD+Vehicle was 5×FAD mice intraperitoneally injected with the control solvent, and 5×FAD+AZ1 was 5×FAD mice experimental group intraperitoneally injected with AZ1. After 4 weeks of continuous administration, a behavioral tests related to learning and memory was performed. After the test, AZ1 was administered for another week. The mice were anesthetized with 5% chloral hydrate, then perfused with phosphate buffered saline, and the brain tissue was collected. The brain tissue was fixed in 4% paraformaldehyde overnight at 4° C. and dehydrated sequentially with 25% and 30% sucrose solutions. The brain tissue was then embedded by OCT, sliced, subjected to antigen-repair with sodium citrate buffer, blocked with 3% BSA buffer containing 0.2% Triton X-100, and subjected to immunofluorescence staining to label microglia marker protein Iba1 (Wako) and the nuclear dye 4',6-diamidino-2-phenylindole (DAPI) (sigma), respectively, followed by image acquisition with laser confocal fluorescence microscopy. As shown in FIGS. 9A-D, compared with WT+Vehicle mice, the number of microglia in the cerebral cortex and hippocampal CA1 and DG regions of 5×FAD+Vehicle mice was significantly increased, while the administration of AZ1 significantly reduced the microglia hyperplasia in the brain of 5×FAD mice. The immunofluorescence staining images were 3D-reconstructed by Imaris software, and as shown in FIGS. 9E-I, the administration of AZ1 significantly increased the number and length of branch of microglia in the brain of 5×FAD mice, suggesting that microglial activation was inhibited. Summing up, it was shown that the administration of AZ1 significantly inhibited microglial proliferation and activation in AD mouse brain.

Example 48. Administration of AZ1 Inhibits Lipopolysaccharide-Induced Microglial Inflammatory Response Microglia were isolated from newborn C57BL/6 mice on postnatal day 0, and cultured in DMEM medium containing 25 ng/mL GM-CSF+10% fetal bovine serum for 10 days, and then shaken at 220 rpm for 15 minutes to separate microglia. The microglia were cultured for 1 day, were treated with 50 ng/mL lipopolysaccharide (LPS) and 10 μM AZ1 respectively, where Control was the control group, LPS+Vehicle was the experimental group treated with 50 ng/mL LPS, and LPS+AZ1 was the experimental group treated with 50 ng/mL LPS and 10 μM AZ1 simultaneously.

Figure 10:
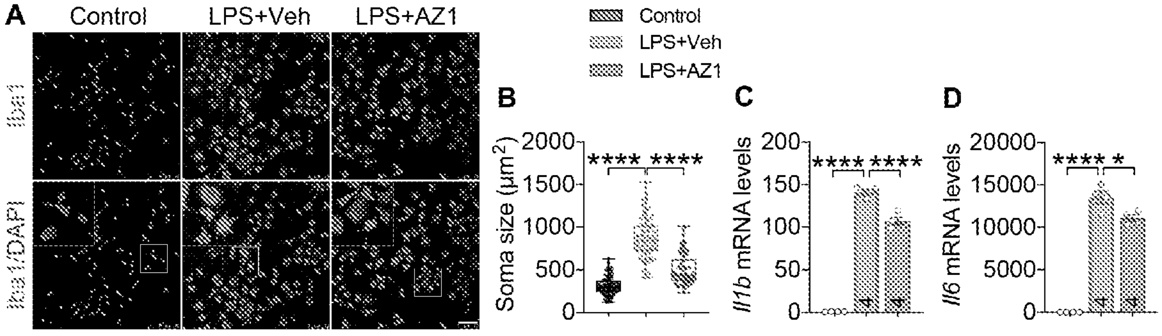
FIG. 10 shows the experiment of inhibiting lipopolysaccharide-induced inflammatory response of microglia cell by administration of AZ1; wherein the microglia of C57BL/6 mice on postnatal day 0 were isolated, cultured for 10 days, and treated with 50 ng/mL lipopolysaccharide (LPS) and 10 μM AZ1, respectively. In the figures, "Control" is the control group, "LPS+Vehicle" is the experimental group treated with 50 ng/mL LPS, and "LPS+AZ1" is the experimental group treated with 50 ng/mL LPS and 10 μM AZ1 at the same time. After 6 hours, immunofluorescence staining and RNA extraction were performed, respectively. Figure (A) is a schematic diagram of immunofluorescence staining of the microglia marker protein Iba1. Scale bar, 75 μm. Figure (B) shows the statistical result of the microglia cell body area (Soma size) in Figure (A). n (Control)=79 microglia, n (LPS+Vehicle)=80 microglia, n (LPS+AZ1)=74 microglia. Figures (C) and (D) show that the RNAs of the extracted microglia were reverse-transcribed, and the transcription levels of inflammation-related genes Il1b and Il6 were detected by real-time quantitative fluorescence PCR. n (Control)=4, n (LPS+Vehicle)=4, n (LPS+AZ1)=4. Data in Figure (B) were statistically analyzed by Kruskal-Wallis test, and data in Figures (C, D) were statistically analyzed by one-way ANOVA. P<0.01; **P<0.0001.

After treated for 6 hours, the cells were fixed in 4% paraformaldehyde, penetrated by 0.2% Triton X-100 solution, blocked by 3% BSA solution, and then immunofluorescence-labeled with the microglia marker protein Iba1 to analyze effects of AZ1 treatment on the activation of microglia under LPS stress. As shown in FIG. 10A and FIG. 10B, the cell body area of microglia was significantly increased after LPS treatment, suggesting that microglia were activated, while AZ1 treatment can reduce the area of microglia, thereby inhibiting the activation of microglia by LPS.

After the cells were treated for 6 hours, RNAs were extracted by TRIzol (Thermo Fisher Scientific), and then reverse-transcribed using Rever Tra Ace qPCR RT Kit (TOYOBO), and real-time fluorescence quantification PCR was performed using FastStart Universal SYBR Green Master (Roche) to detect the transcription levels of inflammation-related genes Il1b and Il6. As shown in FIG. 10C and FIG. 10D, LPS treatment significantly increased the expressions of pro-inflammatory factors Il1b and Il6, while AZ1 treatment can reduce LPS-induced Il1b and Il6 expressions, thereby inhibiting LPS-induced inflammatory responses.

Summing up, it is shown that AZ1 can inhibit LPS-induced microglial activation and inflammatory responses.

Example 49. Administration of AZ2 Inhibits Neuroinflammation in the Brain of AD Mice 6-month-old WT and 5×FAD male mice were administered with AZ2 or control solvent (an aqueous solution containing 1% Tween-80 and 0.5% CMC-Na, pH 3~4) at a dose of 20 mg/kg by gavage, wherein WT+Vehicle was the littermate control wild-type mice administered with the control solvent by gavage, 5×FAD+Vehicle was 5×FAD mice administered with the control solvent by gavage, and 5×FAD+AZ2 was 5×FAD mice experimental group administered with AZ2 by gavage.

After 4 weeks of continuous administration, the mice was anesthetized with 5% chloral hydrate, then perfused with phosphate buffered saline, and the brain tissue was collected, snap-frozen in liquid nitrogen, and stored in a −80° C. refrigerator. RNAs were extracted by TRIzol (Thermo Fisher Scientific), then reverse-transcribed using Rever Tra Ace qPCR RT Kit (TOYOBO), and real-time fluorescence quantification PCR was performed using FastStart Universal SYBR Green Master (Roche) to detect the transcription levels of inflammation-related genes Il1b and Il6. As shown in FIG. 11, compared with WT+Vehicle mice, the expression levels of pro-inflammatory factors Il1b and Il6 were significantly up-regulated in the brains of 5×FAD+Vehicle mice, while the administration of AZ2 significantly reduced the expression of Il1b in the brains of 5×FAD mice, however, the administration of AZ2 exhibited no significant effects on the expression of Il6. Summing up, it was shown that the administration of AZ2 can inhibit the inflammatory response in the brain of AD mouse.

Figure 12:
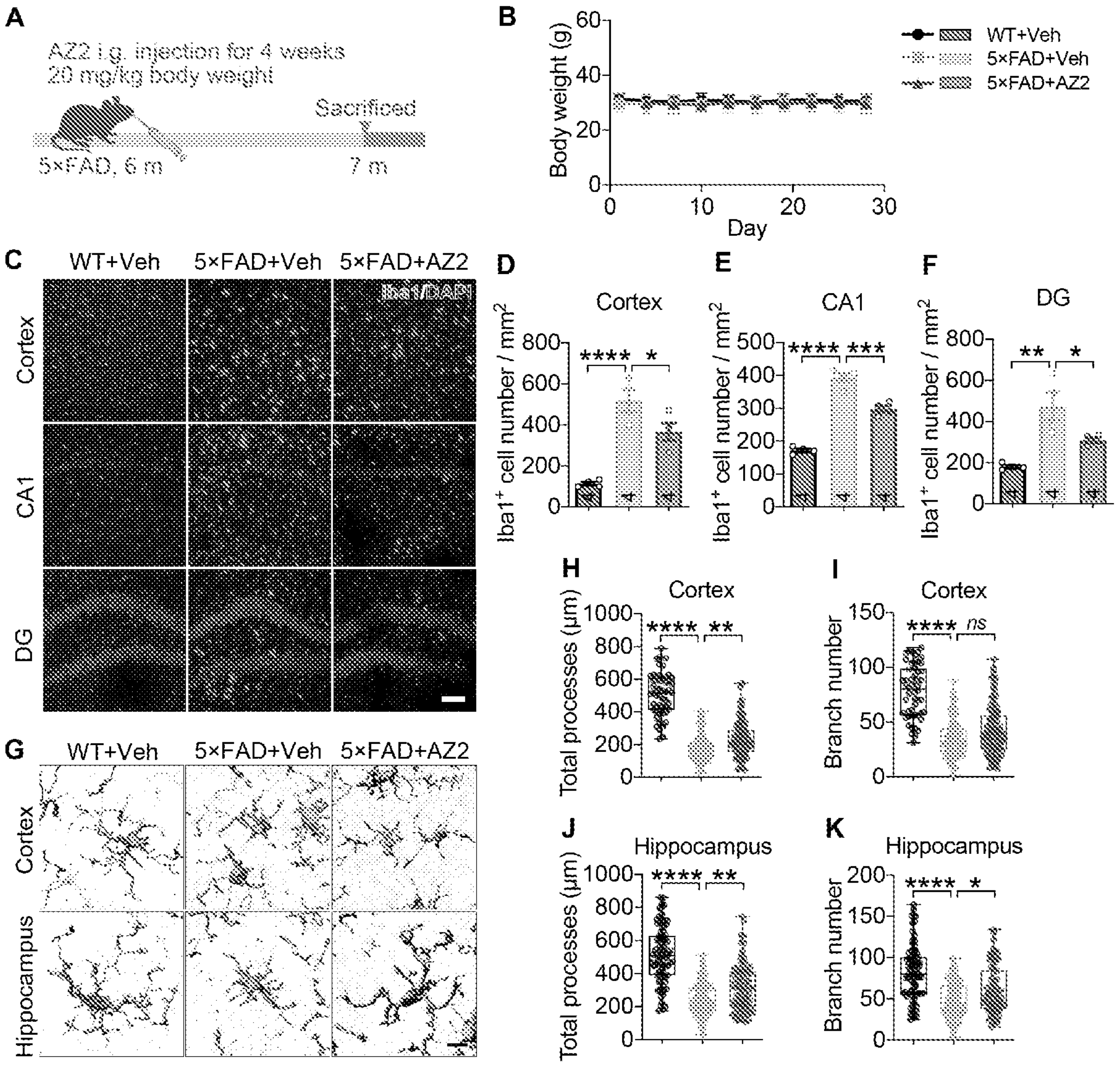
FIG. 12 shows the experiment that administration of AZ1 inhibits the proliferation and activation of microglia in the brain of AD mice; wherein (A) 6-month-old WT and 5×FAD male mice were administered with AZ2 or a control solvent (containing 1% Tween-80 and 0.5% CMC-Na aqueous solution, pH 3~4) by gavage at a dose of 20 mg/kg, respectively, WT+Vehicle was the littermate control wild-type mice administered with the control solvent by gavage, 5×FAD+Vehicle was 5×FAD mice administered with the control solvent by gavage, and 5×FAD+AZ2 was 5×FAD mice experimental group administered with AZ2 by gavage. (B) Changes in the body weight of mice before and after administration of AZ2. n (WT+Vehicle)=16, n (5×FAD+Vehicle)=9, and n (5×FAD+AZ2)=10. After continuous administration for 4 weeks, the mice were anesthetized with 5% chloral hydrate, and perfused with phosphate buffer. The brain tissue was taken, fixed in 4% paraformaldehyde overnight, dehydrated by 25% and 30% sucrose solution, embedded in brain tissue using OCT, sliced, and subjected to immunofluorescence staining to label microglia marker protein Iba1 and nuclear dye 4',6-diamidino-2-phenylindole (DAPI), and images were collected by confocal fluorescence microscopy. Figure (C) shows the result of immunohistochemical staining of $Iba1^+$ microglia in cerebral cortex, hippocampal CA1 area and DG area. Scale bar, 100 μm. Figures (D-F) show the results of statistical analysis of the cerebral cortex (D), hippocampal CA1 area (E) and DG area (F), respectively. n=4 mice per group. (G) shows representative images of $Iba1^+$ microglia in hippocampus tissue 3D-reconstructed by Imaris software. Scale bar, 10 μm. (H-K) Statistical analysis results of microglial branch length (Total processes, H, J) and branch number (Branch number, I, K). n=4 mice per group, 52123 microglia. Data in Figure (B) were statistically analyzed by repeated-measures ANOVA, data in Figures (D-F) were statistically analyzed by One-way ANOVA, and data in Figures (H-K) were statistically analyzed by Kruskal-Wallis test. *P<0.05; P<0.01; *P<0.001; ****P<0.0001.

Example 50. Administration of AZ2 Inhibits Microglial Proliferation and Activation in the Brain of AD Mouse 6-month-old WT and 5×FAD male mice were administered with AZ2 or control solvent (an aqueous solution containing 1% Tween-80 and 0.5% CMC-Na, pH 3~4) at a dose of 20 mg/kg by gavage, wherein WT+Vehicle was the littermate control wild-type mice administered with the control solvent by gavage, 5×FAD+Vehicle was 5×FAD mice administered with the control solvent by gavage, and 5×FAD+AZ2 was 5×FAD mice experimental group administered with AZ2 by gavage (FIG. 12A). As shown in FIG. 12B, the administration of AZ2 did not affect the body weight of mice.

After 4 weeks of continuous administration, the mice were anesthetized with 5% chloral hydrate, then perfused with phosphate buffered saline, and the brain tissue was collected. The brain tissue was fixed in 4% paraformaldehyde overnight at 4° C. and dehydrated sequentially with 25% and 30% sucrose solutions. The brain tissue was then embedded by OCT, sliced, subjected to antigen-repair with sodium citrate buffer, blocked with 3% BSA buffer containing 0.2% Triton X-100, and subjected to immunofluorescence staining to label microglia marker protein Iba1 (Wako) and the nuclear dye 4',6-diamidino-2-phenylindole (DAPI) (sigma), respectively, followed by image acquisition with laser confocal fluorescence microscopy. As shown in FIGS. 12C-F, compared with WT+Vehicle mice, the number of microglia in the cerebral cortex and hippocampal CA1 and DG regions of 5×FAD+Vehicle mice was significantly increased, while the administration of AZ2 significantly reduced the microglia hyperplasia in the brain of 5×FAD mice. The immunofluorescence staining images were 3D-reconstructed by Imaris software, and as shown in FIGS. 12G-K, the administration of AZ2 significantly increased the number and length of branch of microglia in the cerebral cortex and hippocampal CA1 and DG regions of 5×FAD mice, suggesting that microglial activation was inhibited. Summing up, it was shown that the administration of AZ2 significantly inhibited microglial proliferation and activation in AD mouse brain.

Example 51. Administration of AZ2 Inhibits Lipopolysaccharide-Induced Microglial Inflammatory Response Microglia were isolated from newborn C57BL/6 mice on postnatal day 0, and cultured in DMEM medium containing 25 ng/mL GM-CSF+10% fetal bovine serum for 10 days, and then shaken at 220 rpm for 15 minutes to separate microglia. The microglia were cultured for 1 day, were treated with 50 ng/mL lipopolysaccharide (LPS) and 10 μM AZ2 respectively, where Control was the control group, AZ2 was the control group treated with 10 μM AZ2, LPS+Vehicle was the experimental group treated with 50 ng/mL LPS, and LPS+AZ2 was the experimental group treated with 50 ng/mL LPS and 10 μM AZ2 simultaneously.

Figure 13:
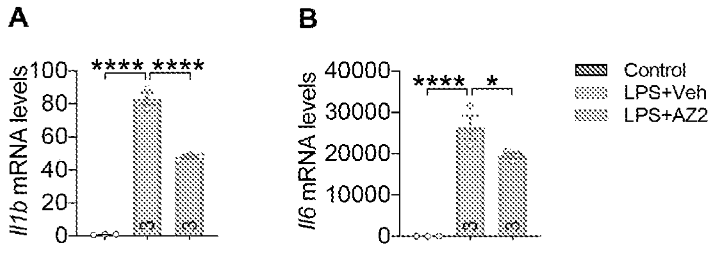
FIG. 13 shows the experiment of inhibiting lipopolysaccharide-induced inflammatory response of microglia cell by administration of AZ2; wherein the microglia of C57BL/6 mice on postnatal day 0 were isolated, cultured for 10 days, and treated with 50 ng/mL lipopolysaccharide (LPS) and 10 μM AZ2, respectively. In the figures, "Control" was the control group, "LPS+Vehicle" was the experimental group treated with 50 ng/mL LPS, and "LPS+AZ2" was the experimental group treated with 50 ng/mL LPS and 10 μM AZ2 at the same time. After 6 hours, the RNAs were extracted and reverse-transcribed, and the transcription levels of inflammation-related genes Il1b (A) and Il6 (B) were detected by real-time quantitative fluorescence PCR. n(Control)=3, n (LPS+Vehicle)=3, and n (LPS+AZ2)=3. Data were statistically analyzed by one-way ANOVA. *P<0.05; ****P<0.0001.

After the cells were treated for 6 hours, RNAs were extracted by TRIzol (Thermo Fisher Scientific), and then reverse-transcribed using Rever Tra Ace qPCR RT Kit (TOYOBO), and real-time fluorescence quantification PCR was performed using FastStart Universal SYBR Green Master (Roche) to detect the transcription levels of inflammation-related genes Il1b and Il6. As shown in FIG. 13, LPS treatment significantly increased the expressions of pro-inflammatory factors Il1b and Il6, while AZ2 treatment can reduce LPS-induced Il1b and Il6 expressions, thereby inhibiting LPS-induced inflammatory responses.

Example 52. Screening of USP25 Inhibitors

Figure 14:
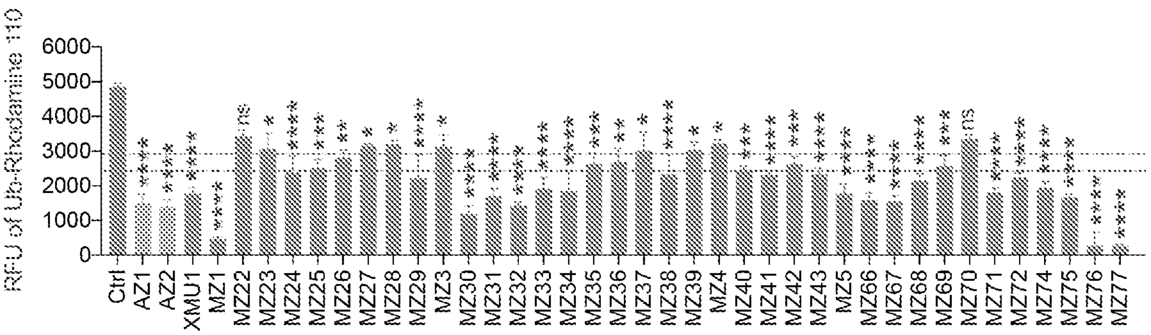
FIG. 14 shows an experiment for screening USP25 inhibitor; wherein His-$USP25^{a.a.157\text{-}706}$ recombinant protein ($USP25^{a.a.157\text{-}706}$ is USP25 deubiquitinase catalytic domain) expressed by *E. coli* BL21 (DE3) was purified by using Ni-NTA Agarose (Qiagen, Cat. No. 1018244); USP25 inhibitors were screened based on Ubiquitin-Rhodamine 110 (R&D Systems, Cat. No. U-555-050) conjugated to the fluorescent dye Rhodamine 110 at the C-terminus; 10 μM (final concentration) compound, 33.3 nM (final concentration) His-$USP25^{157\text{-}706}$ recombinant protein and 133.3 nM (final concentration) Ubiquitin-Rhodamine 110 were incubated, and 25 mM (final concentration) citric acid was added to quench the reaction. And then, the fluorescence intensity of Ubiquitin-Rhodamine 110 was detected by a Tecan Spark multifunctional microplate reader (Tecan, Switzerland). In the figure, Ctrl was the control solution treatment group, and His-$USP25^{a.a.157\text{-}706}$ was recombinant protein+control solvent+Ubiquitin-Rhodamine 110. n=3. Data were statistically analyzed by one-way ANOVA. ns, no significant difference, P>0.05; *P<0.05; P<0.01; *P<0.001; ****P<0.001.

His-USP25$^{a.a.157\text{-}706}$ recombinant protein (USP25$^{a.a.157\text{-}706}$ is USP25 deubiquitinase catalytic domain) expressed by *E. coli* BL21 (DE3) was purified by using Ni-NTA Agarose (Qiagen, Cat. No. 1018244); USP25 inhibitors were screened based on Ubiquitin-Rhodamine 110 (R&D Systems, Cat. No. U-555-050) conjugated to the fluorescent dye Rhodamine 110 at the C-terminus; and the working buffer was 50 mM HEPES (pH 7.4), 0.5 mM EDTA, 1 mM tris-(2-Carboxyethyl) phosphine (TCEP), 1 mg/ml bovine serum albumin (BSA). In a 384-well plate (Corning Company, Cat. No. 3570), 6.25 μl of 33.3 μM compound (18.75 μl system with a final concentration of 10 μM, DMSO final concentration of 0.1%) and 6.25 μl of 100 nM His-USP25$^{157\text{-}706}$ recombinant protein (18.75 μl of the system with a final concentration of 33.3 nM), briefly centrifuged at 150 g for 30 seconds, and incubated at room temperature for 20 minutes; then 6.25 μl of 400 nM Ubiquitin-Rhodamine 110 (18.75 μl system with a final concentration of 133.3 nM), briefly centrifuged at 150 g for 30 seconds, and incubated at room temperature for 30 minutes; and finally, 6.25 μl of 100 mM citric acid was added to quench the reaction (25 μl system with a final concentration of 25 mM), and briefly centrifuged at 150 g for 30 seconds. Ubiquitin-Rhodamine 110 fluorescence intensity was detected on Tecan Spark multi-plate reader (Tecan, Switzerland) with the excitation wavelength of 485 nm and the emission wavelength of 520 nm. (Buffer+Ubiquitin-Rhodamine 110+citric acid) was the negative control group, Ctrl was the control solution treatment group (His-USP25$^{a.a.157\text{-}706}$ recombinant protein+control solvent+Ubiquitin-Rhodamine 110+citric acid), and the fluorescence intensity values of all experimental groups and Ctrl group were deducted from those of the negative control group. As shown in FIG. 14, MZ77, MZ76, MZ1, MZ30, AZ2, MZ32, AZ1, MZ67, MZ66, MZ75, MZ31, MZ5, XMU1, MZ71, MZ34, MZ33, MZ74, MZ68, MZ29, MZ72, MZ41, MZ43, MZ38, MZ24, MZ40, MZ25, MZ69, MZ42, MZ35, MZ36, MZ26, MZ37, MZ39, MZ23, MZ3, MZ27, MZ28, MZ4 can significantly inhibit the deubiquitinase activity of USP25.

Example 53. Administration of XMU1 Inhibits Lipopolysaccharide-Induced Microglial Inflammatory Response Microglia were isolated from newborn C57BL/6 mice on postnatal day 0, and cultured in DMEM medium containing 25 ng/mL GM-CSF+10% fetal bovine serum for 10 days, and then shaken at 220 rpm for 15 minutes to separate microglia. The microglia were cultured for 1 day, were treated with 50 ng/mL lipopolysaccharide (LPS) and 10 μM XMU1 respectively, where Control was the control group, XMU1 was the control group treated with 10 μM XMU1, LPS+Vehicle was the experimental group treated with 50 ng/mL LPS, and LPS+XMU1 was the experimental group treated with 50 ng/mL LPS and 10 μM XMU1 simultaneously.

Figure 15:
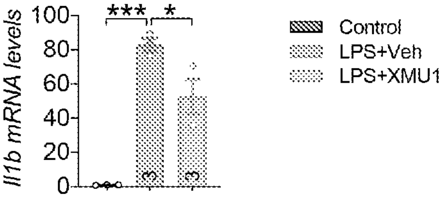
FIG. 15 shows the experiment of inhibiting lipopolysaccharide-induced inflammatory response of microglia cell line BV2 by administration of XMU1 (a derivative of AZ1); wherein the mice microglia cell line BV2 were treated with 50 ng/mL lipopolysaccharide (LPS) and 10 μM XMU1, respectively. In the figure, "Control" was the control group, "XMU1" was the control group treated with 10 μM XMU150, "LPS+Vehicle" was the experimental group treated with 50 ng/mL LPS, and "LPS+XMU1" was the experimental group treated with 50 ng/mL LPS and 10 μM XMU1 at the same time. After 6 hours, the RNAs were extracted and reverse-transcribed, and the transcription levels of inflammation-related gene Il1b was detected by real-time quantitative fluorescence PCR.

After the cells were treated for 6 hours, RNAs were extracted by TRIzol (Thermo Fisher Scientific), and then reverse-transcribed using Rever Tra Ace qPCR RT Kit (TOYOBO), and real-time fluorescence quantification PCR was performed using FastStart Universal SYBR Green Master (Roche) to detect the transcription levels of inflammation-related gene Il1b. As shown in FIG. 15, LPS treatment significantly increased the expressions of pro-inflammatory factor Il1b, while XMU1 treatment can significantly reduce LPS-induced Il1b expression, indicating that the administration of XMU1 can inhibit LPS-induced inflammatory responses.

Example 54. Administration of MZ3 (a AZ1 Derivative) Inhibits Lipopolysaccharide-Induced Inflammatory Response in Microglia Cell Line BV2

Mouse microglial cell line BV2 was treated with 25 ng/mL lipopolysaccharide (LPS) and 10 μM MZ3, respectively. Control was the control group, LPS+Vehicle was the experimental group treated with 25 ng/mL LPS, and LPS+MZ3 was the experimental group treated with 25 ng/mL LPS and 10 μM MZ3 simultaneously.

Figure 16:
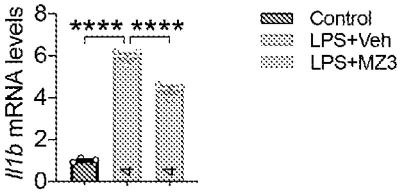
FIG. 16 shows the experiment of inhibiting lipopolysaccharide-induced inflammatory response of microglia cell line BV2 by administration of MZ3 (a derivative of AZ1); wherein the mice microglia cell line BV2 were treated with 25 ng/mL lipopolysaccharide (LPS) and 10 μM MZ3, respectively. In the figure, "Control" was the control group, "LPS+Vehicle" was the experimental group treated with 25 ng/mL LPS, and "LPS+MZ3" was the experimental group treated with 25 ng/mL LPS and 10 μM MZ3 at the same time. After 24 hours, the RNAs were extracted and reverse-transcribed, and the transcription levels of inflammation-related gene Il1b was detected by real-time quantitative fluorescence PCR. n (Control)=4, n (LPS+Vehicle)=4, n (LPS+MZ2)=4, and n (LPS+MZ3)=4. Data were statistically analyzed by one-way ANOVA. *P<0.001; **P<0.0001.

After the cells were treated for 24 hours, RNAs were extracted by TRIzol (Thermo Fisher Scientific), and then reverse-transcribed using Rever Tra Ace qPCR RT Kit (TOYOBO), and real-time fluorescence quantification PCR was performed using FastStart Universal SYBR Green Master (Roche) to detect the transcription levels of inflammation-related gene Il1b. As shown in FIG. 16, LPS treatment significantly increased the expressions of pro-inflammatory factor Il1b, while MZ3 treatment can significantly reduce LPS-induced Il1b expression, thereby inhibiting LPS-induced inflammatory responses.

Example 55. Administration of MZ23 and MZ34 (AZ1 Derivatives) Inhibits Lipopolysaccharide-Induced Inflammatory Response in Microglia Cell Line BV2

Mouse microglial cell line BV2 was treated with 50 ng/mL lipopolysaccharide (LPS) and 10 μM MZ23 or MZ34, respectively. Control was the control group, LPS+Vehicle was the experimental group treated with 50 ng/mL LPS, LPS+MZ23 was the experimental group treated with 50 ng/mL LPS and 10 μM MZ23 simultaneously, and LPS+MZ34 was the experimental group treated with 50 ng/mL LPS and 10 μM MZ34 simultaneously.

Figure 17:
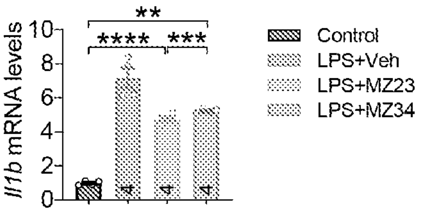
FIG. 17 shows the experiment of inhibiting lipopolysaccharide-induced inflammatory response of microglia cell line BV2 by administration of MZ23 and MZ34 (derivatives of AZ1); wherein the mice microglia cell line BV2 were treated with 50 ng/mL lipopolysaccharide (LPS) and 10 μM MZ23 or MZ34, respectively. In the figure, "Control" was the control group, "LPS+Vehicle" was the experimental group treated with 50 ng/mL LPS, "LPS+MZ23" was the experimental group treated with 50 ng/mL LPS and 10 μM MZ23 at the same time, and "LPS+MZ34" was the experimental group treated with 50 ng/mL LPS and 10 μM MZ34 at the same time. After 12 hours, the RNAs were extracted and reverse-transcribed, and the transcription levels of inflammation-related gene Il1b was detected by real-time quantitative fluorescence PCR. n (Control)=4, n (LPS+Vehicle)=4, n (LPS+MZ23)=4, and n (LPS+MZ34)=4. Data were statistically analyzed by one-way ANOVA. P<0.01; *P<0.001; ****P<0.0001.

After the cells were treated for 12 hours, RNAs were extracted by TRIzol (Thermo Fisher Scientific), and then reverse-transcribed using Rever Tra Ace qPCR RT Kit (TOYOBO), and real-time fluorescence quantification PCR was performed using FastStart Universal SYBR Green Master (Roche) to detect the transcription levels of inflammation-related gene Il1b. As shown in FIG. 17, LPS treatment significantly increased the expressions of pro-inflammatory factor Il1b, while MZ23 and MZ34 treatment can significantly reduce LPS-induced Il1b expression, thereby inhibiting LPS-induced inflammatory responses.

Example 56. Administration of MZ24, MZ25, MZ26, MZ28, MZ29 and MZ31 (AZ1 Derivatives) Inhibits Lipopolysaccharide-Induced Inflammatory Response in Microglia Cell Line BV2

Mouse microglial cell line BV2 was treated with 100 ng/mL lipopolysaccharide (LPS) and 10 μM MZ24, MZ25, MZ26, MZ28, MZ29 and MZ31, respectively. Control was the control group, LPS+Vehicle was the experimental group treated with 100 ng/mL LPS, LPS+MZ24 was the experimental group treated with 100 ng/mL LPS and 10 μM MZ24 simultaneously, LPS+MZ25 was the experimental group treated with 100 ng/mL LPS and 10 μM MZ25 simultaneously; LPS+MZ25 was the experimental group treated with 100 ng/mL LPS and 10 μM MZ25 simultaneously; LPS+MZ26 was the experimental group treated with 100 ng/mL LPS and 10 μM MZ26 simultaneously; LPS+MZ28 was the experimental group treated with 100 ng/mL LPS and 10 μM MZ28 simultaneously; LPS+MZ29 was the experimental group treated with 100 ng/mL LPS and 10 μM MZ29 simultaneously; and LPS+MZ31 was the experimental group treated with 100 ng/mL LPS and 10 μM MZ31 simultaneously.

Figure 18:
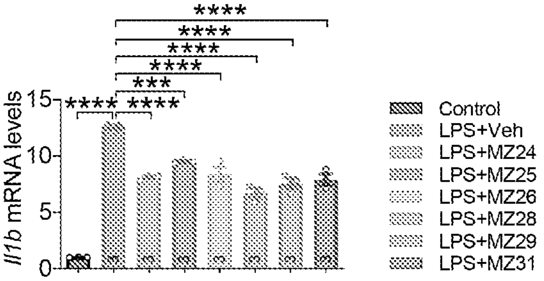
FIG. 18 shows the experiment of inhibiting lipopolysaccharide-induced inflammatory response of microglia cell line BV2 by administration of MZ24, MZ25, MZ26, MZ28, MZ29 and MZ31 (derivatives of AZ1); wherein the mice microglia cell line BV2 were treated with 100 ng/mL lipopolysaccharide (LPS) and 10 μM MZ24, MZ25, MZ26, MZ28, MZ29 and MZ31, respectively. In the figure, "Control" was the control group, "LPS+Vehicle" was the experimental group treated with 100 ng/mL LPS, "LPS+MZ24" was the experimental group treated with 100 ng/mL LPS and 10 μM MZ24 at the same time, "LPS+MZ25" was the experimental group treated with 100 ng/mL LPS and 10 μM MZ25 at the same time, "LPS+MZ26" was the experimental group treated with 100 ng/mL LPS and 10 μM MZ26 at the same time, "LPS+MZ28" was the experimental group treated with 100 ng/mL LPS and 10 μM MZ28 at the same time, "LPS+MZ29" was the experimental group treated with 100 ng/mL LPS and 10 μM MZ29 at the same time, and "LPS+MZ31" was the experimental group treated with 100 ng/mL LPS and 10 μM MZ31 at the same time. After 12 hours, the RNAs were extracted and reverse-transcribed, and the transcription levels of inflammation-related gene Il1b was detected by real-time quantitative fluorescence PCR. n=3 per group. Data were statistically analyzed by one-way ANOVA. ****P<0.0001.

After the cells were treated for 12 hours, RNAs were extracted by TRIzol (Thermo Fisher Scientific), and then reverse-transcribed using Rever Tra Ace qPCR RT Kit (TOYOBO), and real-time fluorescence quantification PCR was performed using FastStart Universal SYBR Green Master (Roche) to detect the transcription levels of inflammation-related gene Il1b. As shown in FIG. 18, LPS treatment significantly increased the expressions of pro-inflammatory factor Il1b, while MZ24, MZ25, MZ26, MZ28, MZ29 and MZ31 treatment can significantly reduce LPS-induced Il1b expression, thereby inhibiting LPS-induced inflammatory responses.

Example 57. Administration of MZ75, MZ76 and MZ77 Inhibits Lipopolysaccharide-Induced Microglial Inflammatory Response Microglia were isolated from newborn C57BL/6 mice on postnatal day 0, and cultured in DMEM medium containing 25 ng/mL GM-CSF+10% fetal bovine serum for 10 days, and then shaken at 220 rpm for 15 minutes to separate microglia. The microglia were cultured for 1 day, were treated with 50 ng/mL lipopolysaccharide (LPS) and 10 μM AZ1, MZ75, MZ76 and MZ77 respectively, where Control was the control group, LPS+Vehicle was the experimental group treated with 50 ng/mL LPS, LPS+AZ1 or LPS+MZ75 or LPS+MZ76 or LPS+MZ77 was the experimental group treated with 50 ng/mL LPS and 10 μM AZ1 or MZ75 or MZ76 or MZ77, simultaneously.

Figure 19:
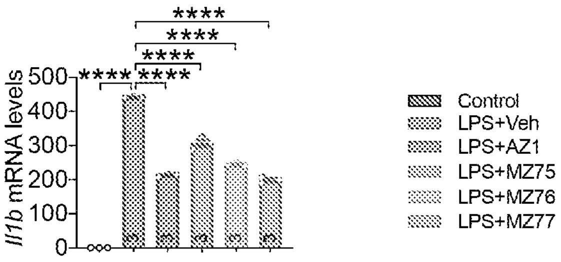
FIG. 19 shows the experiment of inhibiting lipopolysaccharide-induced inflammatory response of microglia cell by administration of MZ75, MZ76 and MZ77 (derivatives of AZ1); wherein the microglia of C57BL/6 mice on postnatal day 0 were isolated, cultured for 10 days, and treated with 50 ng/mL lipopolysaccharide (LPS) and 10 μM AZ1, MZ75, MZ76 and MZ77, respectively. In the figure, "Control" was the control group, "LPS+Vehicle" was the experimental group treated with 50 ng/mL LPS, and "LPS+AZ1" or "LPS+MZ75" or "LPS+MZ76" or "LPS+MZ77" were the experimental groups treated with 50 ng/mL LPS and 10 μM AZ1 or MZ75 or MZ76 or MZ77 at the same time. After 6 hours, the RNAs were extracted and reverse-transcribed, and the transcription levels of inflammation-related genes Il1b were detected by real-time quantitative fluorescence PCR. n=3 per group. Data were statistically analyzed by one-way ANOVA. ****P<0.0001.

After the cells were treated for 6 hours, RNAs were extracted by TRIzol (Thermo Fisher Scientific), and then reverse-transcribed using Rever Tra Ace qPCR RT Kit (TOYOBO), and real-time fluorescence quantification PCR was performed using FastStart Universal SYBR Green Master (Roche) to detect the transcription levels of inflammation-related gene Il1b. As shown in FIG. 19, LPS treatment significantly increased the expressions of pro-inflammatory factor Il1b, while AZ1, MZ75, MZ76 and MZ77 treatment can significantly reduce LPS-induced Il1b expression, thereby inhibiting LPS-induced inflammatory responses.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method of improving cognitive function in Alzheimer's disease or Down's syndrome, or slowing the progression of Alzheimer's disease or Down's syndrome, comprising administering an effective amount of a compound of formula I or a pharmaceutically acceptable salt thereof:

I

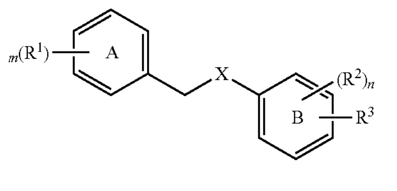

wherein,

X is independently selected from O or NH;

each A ring and B ring is independently a benzene ring;

$R^1$ is independently selected from a hydrogen, deuterium, halogen, cyano, $(C_1-C_6)$alkyl, $(C_1-C_6)$alkyl substituted with one or more substituents selected from halogen, nitro, amino, or hydroxy, $(C_1-C_6)$alkoxy, or $(C_1-C_6)$ alkoxy substituted with one or more substituents selected from halogen, nitro, amino, or hydroxy;

m is 0, 1, 2, 3, 4 or 5;

$R^2$ is independently selected from a hydrogen, halogen, $(C_1-C_6)$alkyl, $(C_1-C_6)$alkyl substituted with one or more substituents selected from halogen, nitro, amino, or hydroxy, $(C_2-C_6)$alkenyl, $(C_2-C_6)$alkenyl substituted with one or more substituents selected from halogen, nitro, amino, or hydroxy, $(C_2-C_6)$alkynyl, $(C_2-C_6)$alkynyl substituted with one or more substituents selected from halogen, nitro, amino, or hydroxy, $(C_1-C_6)$alkoxy, or $(C_1-C_6)$alkoxy substituted with one or more substituents selected from halogen, nitro, amino, or hydroxy;

n is 1 or 2;

$R^3$ is a formyl (—CHO) group, alkanoyl (R—C(O)—) group,

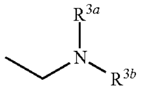

or

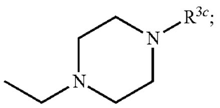

wherein each $R^{3a}$, $R^{3b}$, $R^{3c}$ is independently selected from a hydrogen, $(C_1-C_6)$alkyl, $(C_1-C_6)$alkyl substituted with one or more substituents selected from halogen, nitro, amino, or hydroxy, $(C_2-C_6)$alkenyl, $(C_2-C_6)$alkenyl substituted with one or more substituents selected from halogen, nitro, amino, or hydroxy, $(C_2-C_6)$alkynyl, $(C_2-C_6)$alkynyl substituted with one or more substituents selected from halogen, nitro, amino, or hydroxy, or

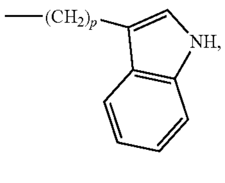

and p is an integer of 1-3.

2. The method of claim 1, wherein the substitution position of $R^3$ on the benzene ring is the ortho position or the meta position.

3. The method of claim 2, wherein $R^1$ is independently selected from a hydrogen, fluorine, chlorine, bromine, $(C_1-C_3)$alkyl, halo$(C_1-C_3)$alkyl, or halo$(C_1-C_3)$alkoxy;

m is 0, 1, 2, or 3;

$R^2$ is independently selected from a hydrogen, or halogen;

n is 1 or 2;

$R^3$ is

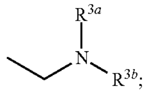

wherein each $R^{3a}$, $R^{3b}$ is independently selected from a hydrogen, hydroxyl-substituted $(C_1-C_4)$alkyl, or

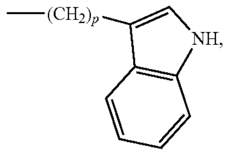

and p is an integer of 1-3.

4. The method of claim 1, wherein the compound of formula I is selected from the following compounds:

AZ1

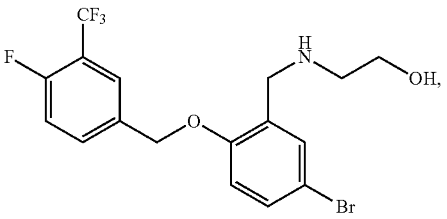

AZ2

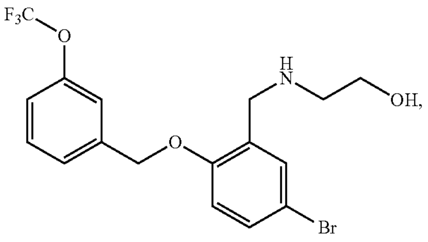

XMU1

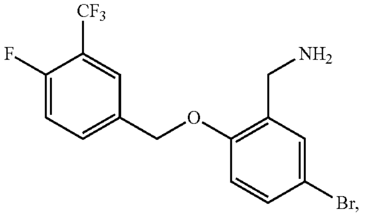

MZ39

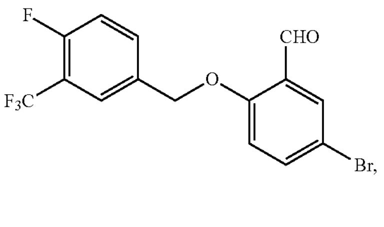

-continued
(1) MZ3
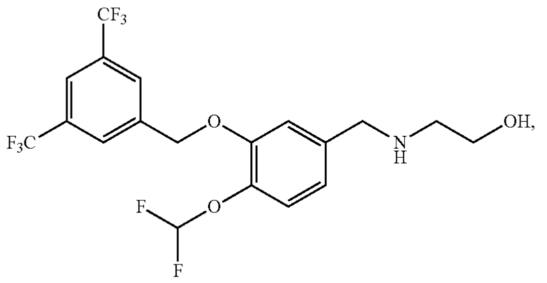
(2) MZ23
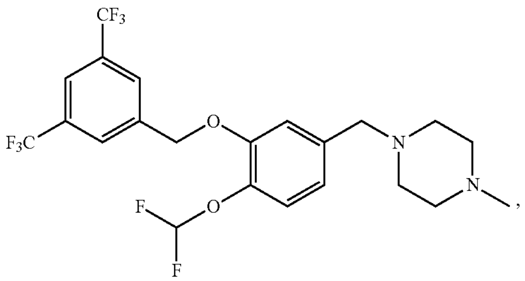
(3) MZ25
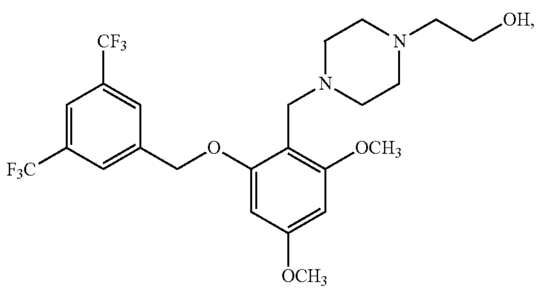
(4) MZ28
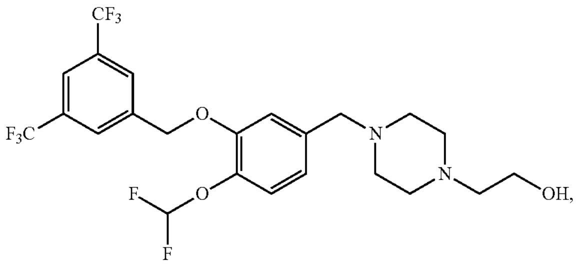
(5) MZ29
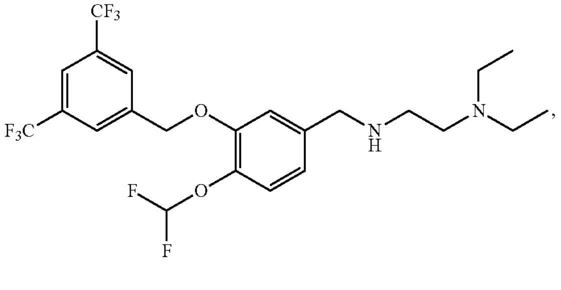
-continued
(6) MX24
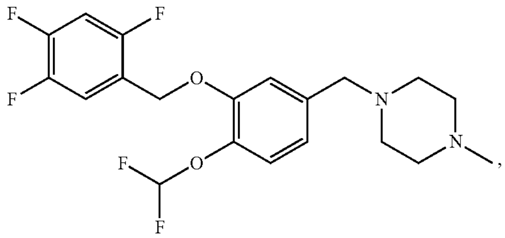
(7) MZ26
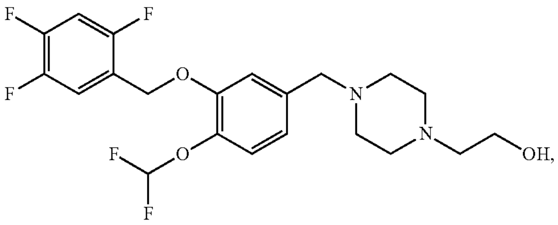
(8) MZ34
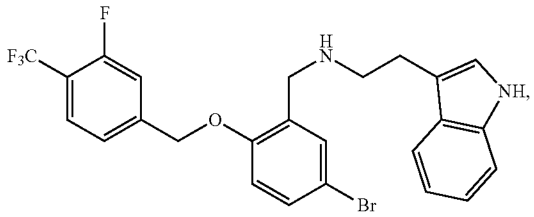
(9) MZ31
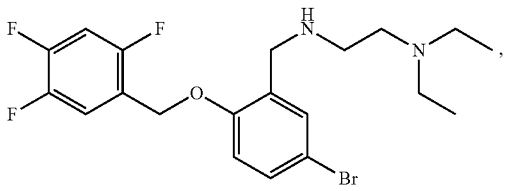
(10) MZ75
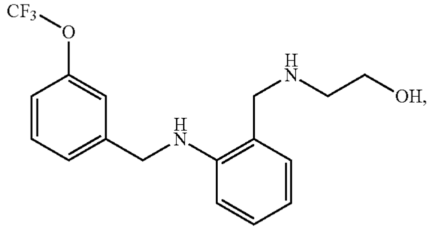
(11) MZ76
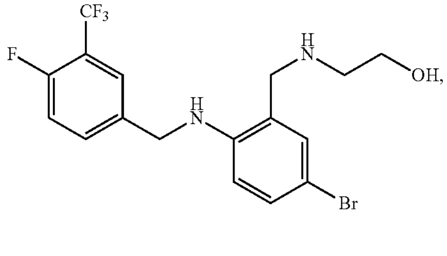

-continued
(12) MZ77
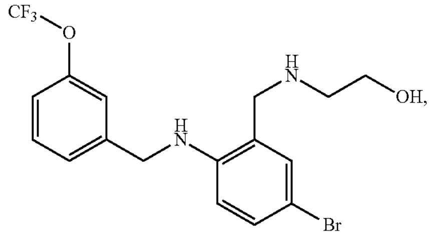
(13) MZ1
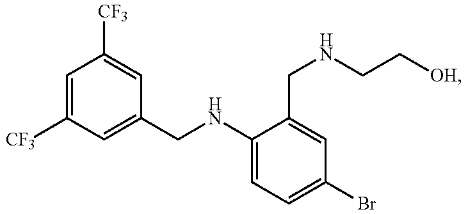
(14) MZ30
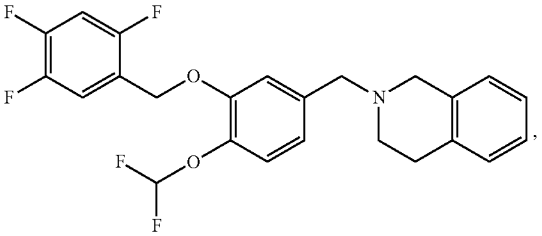
(15) MZ32
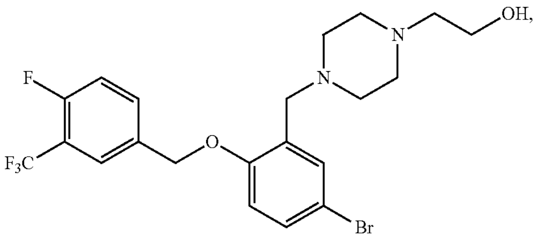
(16) MZ67
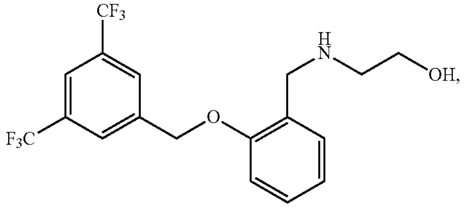
(17) MZ66
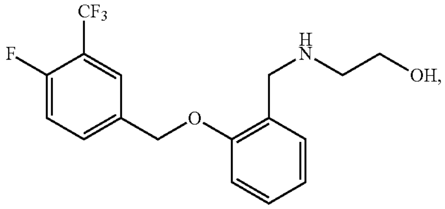
-continued
(18) MZ5
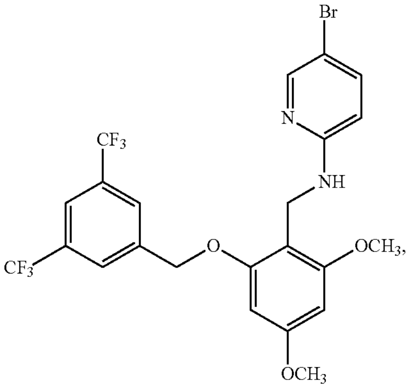
(19) MZ71
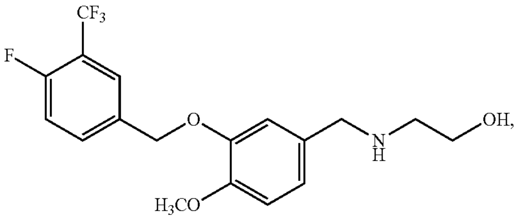
(20) MZ33
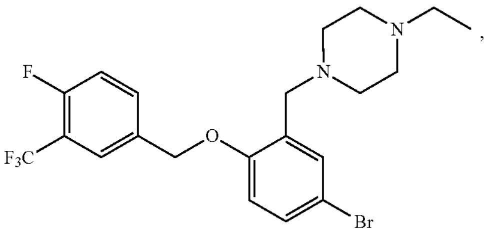
(21) MZ74
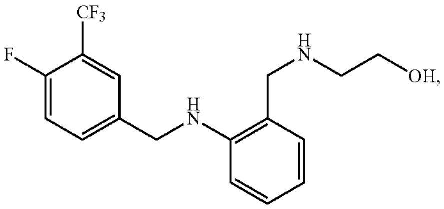
(22) MZ68
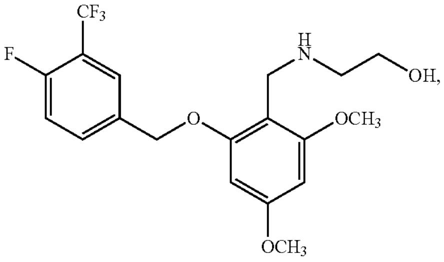

-continued
(23) MZ72
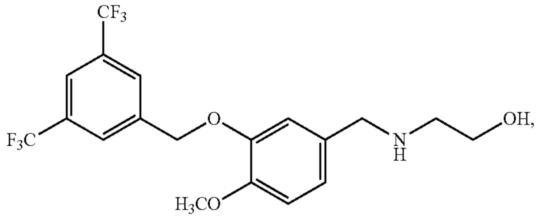
(24) MZ41
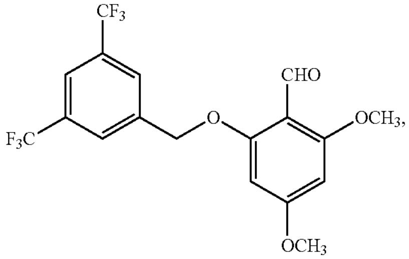
(25) MZ43
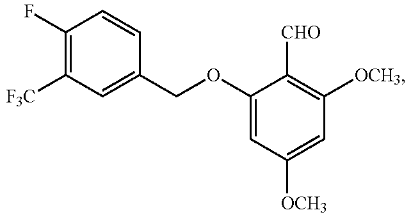
(26) MZ38
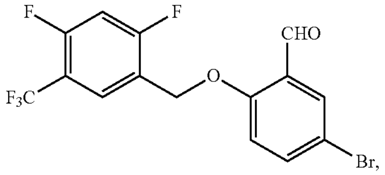
(27) MZ40
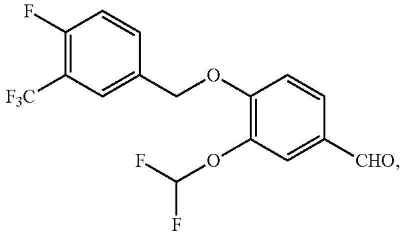
(28) MZ69
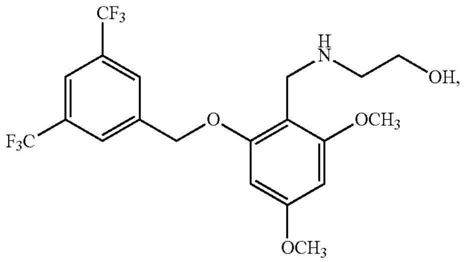
-continued
(29) MZ42
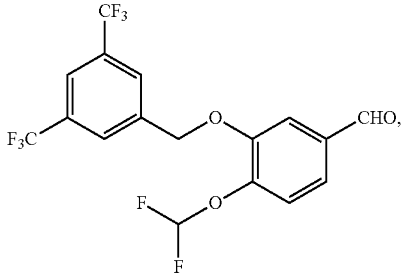
(30) MZ35
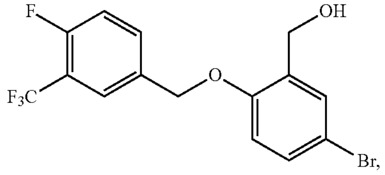
(31) MZ36
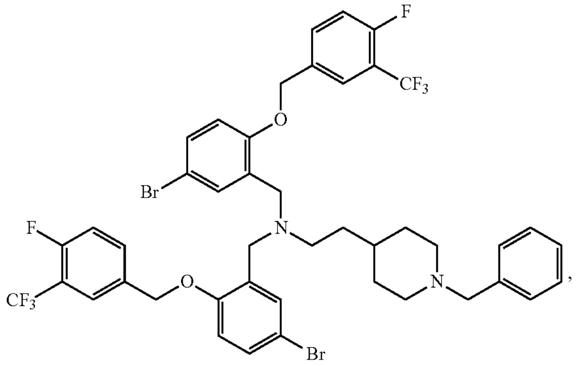
(32) MZ37
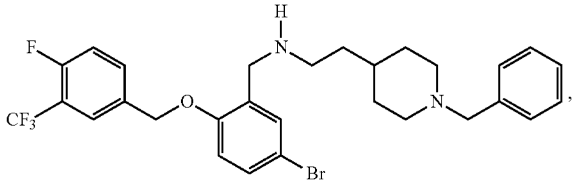
(33) MZ27
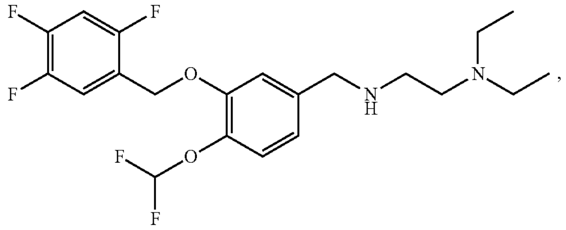

-continued
(34) MZ4
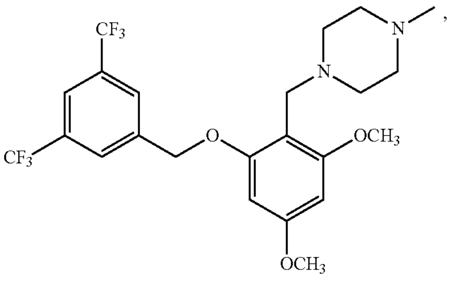
(35) MZ70
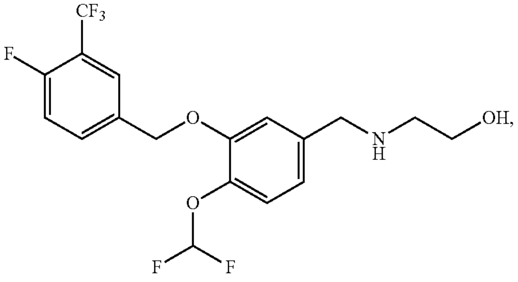
-continued
(36) MZ22
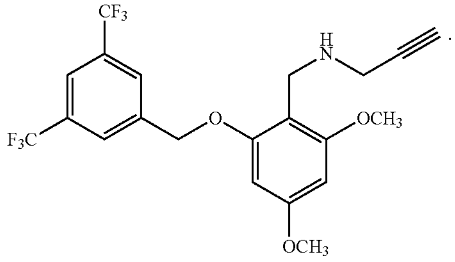
5. The method of claim 4, wherein the compound of formula I is AZ1, AZ2, MZ77, MZ76, MZ1, MZ30, MZ32, MZ67, MZ66, MZ75, MZ31, MZ34, MZ74, MZ68, MZ29, MZ72, MZ38 or MZ24.
6. The method of claim 1, wherein p is 2.
7. The method of claim 2, wherein the benzene ring is the ortho position.
8. The method of claim 3, wherein p is 2.
* * * * *